United States Patent
Lama et al.

(10) Patent No.: US 11,414,422 B2
(45) Date of Patent: Aug. 16, 2022

(54) SUBSTITUTED PYRIDO[4,3-B]INDOLES AND AZEPINO[4,5-B]INDOLES AS INHIBITORS OF CGAS

(71) Applicants: The Rockefeller University, New York, NY (US); Memorial Sloan-Kettering Cancer Center, New York, NY (US)

(72) Inventors: Lodoe Lama, New York, NY (US); Thomas Tuschl, New York, NY (US); Daisuke Tomita, Harrison, NY (US); Dinshaw Patel, New York, NY (US); J. Fraser Glickman, New York, NY (US); Taku Kamei, Kamakura (JP); Michael Miller, Scotch Plains, NY (US); Yasutomi Asano, Chigasaki (JP); Rei Okamoto, Yokohama (JP); Shogo Hashizume, Yokohama (JP); Jumpei Aida, Yokohama (JP); Toshihiro Imaeda, Fujisawa (JP); Mayako Michino, New York, NY (US); Takanobu Kuroita, New York, NY (US)

(73) Assignee: The Rockefeller University, New York, NY (US)

( * ) Notice: Subject to any disclaimer, the term of this patent is extended or adjusted under 35 U.S.C. 154(b) by 204 days.

(21) Appl. No.: 16/967,656

(22) PCT Filed: Feb. 5, 2019

(86) PCT No.: PCT/US2019/016673
§ 371 (c)(1),
(2) Date: Aug. 5, 2020

(87) PCT Pub. No.: WO2019/153002
PCT Pub. Date: Aug. 8, 2019

(65) Prior Publication Data
US 2021/0155625 A1    May 27, 2021

Related U.S. Application Data

(60) Provisional application No. 62/626,466, filed on Feb. 5, 2018.

(51) Int. Cl.
*A61K 31/407* (2006.01)
*C07D 487/04* (2006.01)
*C07D 471/04* (2006.01)

(52) U.S. Cl.
CPC ......... *C07D 487/04* (2013.01); *C07D 471/04* (2013.01)

(58) Field of Classification Search
CPC .................. A81K 31/407; C07D 487/04
USPC ............................... 514/411; 548/429
See application file for complete search history.

(56) References Cited

U.S. PATENT DOCUMENTS
2013/0190331 A1    7/2013  Jain et al.

FOREIGN PATENT DOCUMENTS

| CN | 101857594 A | 10/2010 | |
|---|---|---|---|
| WO | 2009055828 A1 | 4/2009 | |
| WO | 2017176812 A1 | 10/2017 | |
| WO | 2019153002 A1 | 12/2017 | |
| WO | WO-2019153002 A1 * | 8/2019 | ............... A61P 35/00 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
European Search Report in European Application No. 19746977.8, dated Jul. 29, 2021.
Pubchem CID 40129081, May 30, 2009, p. 2.
Vincent et al. "Small molecule inhibition of cGAS reduces interferon expression in primary macrophages from autoimmune mice" Nature Communications, Sep. 29, 2017, vol. 8, pp. 1-13.
Pubchem CID 42534918, May 30, 2009, p. 2.
International Search Report and Written Opinion in International Application No. PCT/US2019/016673 dated Jun. 11, 2019.

* cited by examiner

*Primary Examiner* — Douglas M Willis
(74) *Attorney, Agent, or Firm* — Heslin Rothenberg Farley & Mesiti P.C.

(57) ABSTRACT

1-(3,4-Dihydro-1H-pyrido[4, 3-b]indol-2(5H)-yl)-2-hydroxyethanones

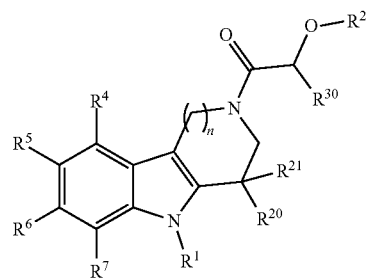

are disclosed. The compounds are inhibitors of human cGAS in interferon-producing cell types. They are thus useful as therapeutic agents for treating cGAS-related autoimmune diseases in humans.

19 Claims, No Drawings

SUBSTITUTED PYRIDO[4,3-B]INDOLES AND AZEPINO[4,5-B]INDOLES AS INHIBITORS OF CGAS

CROSS REFERENCE TO RELATED APPLICATIONS

This application is a 371 National Phase of International Application No. PCT/US2019/016673 filed Feb. 5, 2019 which claims priority from U.S. provisional application 62/626,466, filed Feb. 5, 2018, which is incorporated herein by reference in its entirety.

FIELD OF THE INVENTION

The invention relates to 2, 3, 4, 5-tetrahydro-H-pyrido[4,3-b]indole derivatives, and in particular, 1-(3, 4-dihydro-1H-pyrido[4, 3-b]indol-2(5H)-yl)-2-hydroxyethanones, that are inhibitors of human cGAS in major interferon-producing cell types. They are thus useful as therapeutic agents for treating cGAS-related autoimmune diseases in humans.

BACKGROUND OF THE INVENTION

Innate immunity is considered a first line cellular stress response defending the host cell against invading pathogens and initiating signaling to the adaptive immunity system. These processes are triggered by conserved pathogen-associated molecular patterns (PAMPs) through sensing by diverse pattern recognition receptors (PRRs) and subsequent activation of cytokine and type I interferon gene expression. The major antigen-presenting cells, such as monocytes, macrophages, and dendritic cells produce interferons and are critical for eliciting adaptive T- and B-cell immune system responses. The major PRRs detect aberrant, i.e. mislocalized, immature, or unmodified nucleic acids on either the cell surface, the inside of lysosomal membranes, or the cytosol.

Cyclic GMP-AMP synthase (cGAS/MB21D1) is the predominant sensor for cytosolic dsDNA originating from pathogens or mislocalization of nuclear or mitochondrial self-dsDNA. Binding of dsDNA to cGAS activates the synthesis of c[G(2',5')pA(3',5')p], a diffusible cyclic dinucleotide referred to as cGAMP, which travels to and activates the endoplasmic reticulum membrane-anchored adaptor protein, Stimulator of interferon genes (STING/TMEM173). Activated STING recruits and activates TANK binding kinase 1 (TBK1), which in turn phosphorylates the transcription factor family of interferon regulatory factors (IRFs) inducing cytokine and type I interferon mRNA expression. Type I interferons are expressed from over ten IFNA genes and one IFNB1 gene.

The critical role of cGAS in dsDNA sensing has been established in different pathogenic bacteria, viruses, and retroviruses. Additionally, cGAS is essential in various other biological processes such as cellular senescence and recognition of ruptured micronuclei in the surveillance of potential cancer cells.

While the cGAS pathway is important for host defense against invading pathogens, cellular stress and genetic factors may also cause accumulation of self-dsDNA in the cytosol, e.g. from nuclear or mitochondrial leakage. This can trigger autoinflammatory responses. Aicardi-Goutières syndrome (AGS), a lupus-like severe autoinflammatory immune-mediated disorder, arises from loss-of-function mutation in TREX1, a primary DNA exonuclease responsible for degrading aberrant DNA in cytosol. Knockout of cGAS in TREX1-deficient mice prevented otherwise lethal autoimmune responses, supporting cGAS as a drug target and driver of interferonopathies. Likewise, embryonic lethality caused by deficiency of DNase II, an endonuclease responsible for degradation of excessive DNA in lysosomes during endocytosis, is completely rescued by additional knockout of STING or cGAS. Inhibition of cGAS, therefore, constitutes an important therapeutic strategy for preventing autoinflammatory diseases whose etiology involves anti-dsDNA antibodies. Systemic lupus erythematosus (SLE) may be one such disease [Pisetsky, Nat Rev Rheumatol 12, 102-110 (2016)].

Consequently, cGAS and STING have attracted the interest of structural biologists and medicinal chemists for identification of inhibitors and/or activators. An in silico screening effort using murine cGAS-DNA crystal structure led to the identification of a well-characterized small-molecule anti-malarial drug, quinacrine, as a potential cGAS inhibitor [An et al., J. Immunol. 194, 4089-4093 (2015)]. However, quinacrine, a known DNA intercalator, was found to indirectly affect the cGAS activity through disruption of dsDNA conformation failing to activate the enzyme instead of directly binding and inhibiting the enzyme. Additionally, considerable off-target effect was observed through its interference with RIG-I pathway.

Small molecule inhibitors that are specific for cGAS would be of great value in treating diseases that arise from inappropriate cGAS activity and the resulting undesired type I interferon activity. Examples of such autoimmune diseases include Aicardi-Goutières syndrome (AGS) and systemic lupus erythematosus (SLE), a complex chronic systemic autoimmune disease that afflicts over 1.5 million Americans. Current treatments for SLE involve immuno-suppressive regimens associated with debilitating adverse side effects. Other possible utilities related to the suppression of undesired type I interferon activity would include treating inflammatory bowel disease (IBD). Furthermore, suppressing of the non-canonical cGAS-pathway-dependent NF-kB signaling may interfere with the process of cancer metastasis [Bakhoum et al., Nature 553, 467-472 (2018)].

SUMMARY OF THE INVENTION

It has now been found that 1-(3,4-dihydro-H-pyrido[4,3-b]indol-2(5H)-yl)-2-hydroxyethanone derivatives are potent and specific inhibitors for human cGAS, and are active in interferon-producing cell types including primary human macrophages.

In one aspect, the invention relates to compounds of Formula I

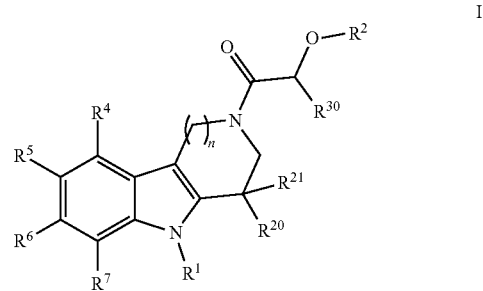

wherein

R[1] is hydrogen, $(C_1-C_3)$alkyl, $CH_2CH_2$—OR[3], or fluoro $(C_1-C_3)$alkyl;

R[2] is hydrogen, $(C_1-C_3)$alkyl, or $CH_2CH_2$—OR[3], or, taken together along with the atoms to which they are attached, R[2] and R[30] may form a 4- to 6-membered aliphatic ring;

R[3] is hydrogen or $(C_1-C_3)$alkyl;

R[4] is chosen from hydrogen, halogen, $(C_1-C_3)$alkoxy, optionally substituted monocyclic heterocyclyl, cyano, optionally substituted phenyl, optionally substituted bicyclic heterocyclyl, amino$(C_1-C_3)$alkyl, $(C_1-C_3)$alkylamino$(C_1-C_3)$alkyl, $(C_1-C_3)$dialkylamino$(C_1-C_3)$alkyl, $(C_1-C_3)$alkoxy$(C_1-C_3)$alkyl, $(C_1-C_6)$hydrocarbyl, heterocyclyl$(C_1-C_3)$alkyl, benzyl, heterocyclyl-substituted benzyl, $(C_1-C_3)$alkylaminocarbonyl, $(C_1-C_3)$acylamino;

wherein:
said optionally substituted monocyclic heterocyclyl may be substituted with one or more substituents chosen from: $(C_1-C_3)$alkyl, amino, cyano, $(C_1-C_3)$alkylamino, $(C_1-C_3)$alkoxy, oxo, fluoro$(C_1-C_3)$alkyl, halogen, hydroxy, and hydroxy$(C_1-C_3)$alkyl;

said optionally substituted phenyl may be substituted with one or more substituents chosen from: amino, $(C_1-C_3)$alkylamino, meta-$(C_1-C_3)$dialkylamino, $(C_1-C_3)$alkoxy, hydroxy, halogen, ortho-cyano, meta-cyano, aminocarbonyl, methylenedioxy, ethylenedioxy, $(C_1-C_3)$acylamino, fluoro$(C_1-C_3)$acylamino, and hydroxy$(C_1-C_3)$alkylaminosulfonyl; and said optionally substituted bicyclic heterocyclyl may be substituted with one or more substituents chosen from: $(C_1-C_3)$alkyl, hydroxy, and oxo;

R[5] is chosen from hydrogen, halogen, $(C_1-C_3)$alkyl, $(C_1-C_3)$alkoxy, fluoro$(C_1-C_3)$alkyl, fluoro$(C_1-C_3)$alkoxy, cyano, and;

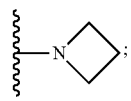

R[6] is chosen from hydrogen, halogen, cyano, —C≡CH, —CH=CH$_2$, methyl, and trifluoromethyl;

R[7] is chosen from hydrogen, halogen, $(C_1-C_3)$alkoxy, fluoro$(C_1-C_3)$alkoxy, cyano, $(C_1-C_3)$alkyl, and fluoro$(C_1-C_3)$alkyl;

R[20] is hydrogen or $(C_1-C_3)$alkyl, or, taken together with the carbon to which they are attached, R[20] and R[21] may form a 3- to 5-membered aliphatic carbocyclic ring;

R[21] is hydrogen or $(C_1-C_3)$alkyl, or, taken together with the carbon to which they are attached, R[21] and R[20] may form a 3- to 5-membered aliphatic carbocyclic ring;

R[30] is hydrogen, or, taken together along with the atoms to which they are attached, R[30] and R[2] may form a 4- to 6-membered aliphatic ring; and n is 1 or 2;

with the provisos that:
(1) when R[2] is $(C_1-C_3)$alkyl, not all of R[4], R[5], R[6], and R[7] can be hydrogen;
(2) when R[1] is hydrogen, R[2] is methyl and R[5] is halogen, R[7] cannot be H or chloro; and
(3) when R[2] is $(C_1-C_3)$alkyl, and R[5] is methoxy or carboxy, R[7] cannot be H.

In one aspect, the invention relates to a method of inhibiting an inflammatory response in a patient comprising administering a compound of formula (II):

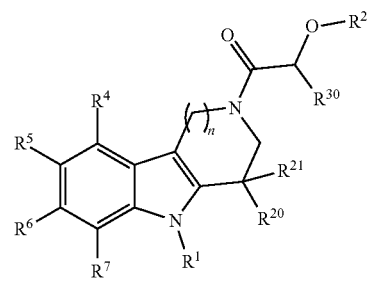

wherein:

R[1] is hydrogen, $(C_1-C_3)$alkyl, $CH_2CH_2$—OR[3], or fluoro $(C_1-C_3)$alkyl;

R[2] is hydrogen or $(C_1-C_3)$alkyl, $CH_2CH_2$—OR[3], or, taken together along with the atoms to which they are attached, R[2] and R[31] may form a 4- to 6-membered aliphatic ring;

R[3] is hydrogen or $(C_1-C_3)$alkyl;

R[4] is chosen from hydrogen, halogen, $(C_1-C_3)$alkoxy, optionally substituted monocyclic heterocyclyl, cyano, optionally substituted phenyl, optionally substituted bicyclic heterocyclyl, amino$(C_1-C_3)$alkyl, $(C_1-C_3)$alkylamino$(C_1-C_3)$alkyl, $(C_1-C_3)$dialkylamino$(C_1-C_3)$alkyl, $(C_1-C_3)$alkoxy$(C_1-C_3)$alkyl, $(C_1-C_6)$hydrocarbyl, heterocyclyl$(C_1-C_3)$alkyl, benzyl, heterocyclyl-substituted benzyl, $(C_1-C_3)$alkylaminocarbonyl, $(C_1-C_3)$acylamino;

wherein:
said optionally substituted monocyclic heterocyclyl may be substituted with one or more substituents chosen from: $(C_1-C_3)$alkyl, amino, cyano, $(C_1-C_3)$alkylamino, $(C_1-C_3)$alkoxy, oxo, fluoro$(C_1-C_3)$alkyl, halogen, hydroxy, and hydroxy$(C_1-C_3)$alkyl;

said optionally substituted phenyl may be substituted with one or more substituents chosen from: amino, $(C_1-C_3)$alkylamino, meta-$(C_1-C_3)$dialkylamino, $(C_1-C_3)$alkoxy, hydroxy, halogen, ortho-cyano, meta-cyano, aminocarbonyl, methylenedioxy, ethylenedioxy, $(C_1-C_3)$acylamino, fluoro$(C_1-C_3)$acylamino, and hydroxy$(C_1-C_3)$alkylaminosulfonyl; and said optionally substituted bicyclic heterocyclyl may be substituted with one or more substituents chosen from: $(C_1-C_3)$alkyl, hydroxy, and oxo;

R[5] is chosen from hydrogen, halogen, $(C_1-C_3)$alkyl, $(C_1-C_3)$alkoxy, fluoro$(C_1-C_3)$alkyl, fluoro$(C_1-C_3)$alkoxy, cyano, and

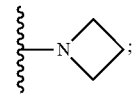

R[6] is chosen from hydrogen, halogen, cyano, —C≡CH, —CH=CH$_2$, methyl, and trifluoromethyl;

R[7] is chosen from hydrogen, halogen, $(C_1-C_3)$alkoxy, fluoro$(C_1-C_3)$alkoxy, cyano, $(C_1-C_3)$alkyl, and fluoro$(C_1-C_3)$alkyl;

R[20] is hydrogen or $(C_1-C_3)$alkyl, or, taken together with the carbon to which they are attached, R[20] and R[21] may form a 3- to 5-membered aliphatic carbocyclic ring;

R[21] is hydrogen or $(C_1-C_3)$alkyl, or, taken together with the carbon to which they are attached, R[21] and R[20] may form a 3- to 5-membered aliphatic carbocyclic ring;

$R^{30}$ is hydrogen, or, taken together along with the atoms to which they are attached, $R^{30}$ and $R^2$ may form a 4- to 6-membered aliphatic ring; and n is 1 or 2.

In another aspect, the invention relates to a method for inhibiting dsDNA-triggered interferon expression in a patient with a compound as described herein.

In another aspect, the invention relates to a method for treating cancer metastasis in a patient with a compound as described herein.

In another aspect, the invention relates to pharmaceutical compositions comprising a pharmaceutically acceptable carrier and a compound as described herein.

DETAILED DESCRIPTION OF THE INVENTION

In a composition aspect, the invention relates to compounds of formula I

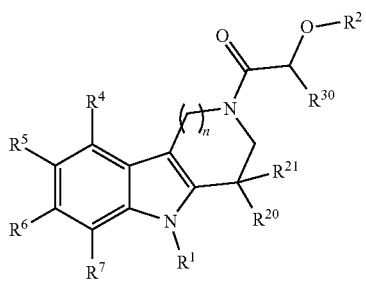

I as described above.

In some embodiments, $R^1$ is hydrogen. In other embodiments, $R^1$ is a $(C_1-C_3)$alkyl group, in particular, methyl. In yet other embodiments, $R^1$ is $CH_2CH_2$—$OR^3$, wherein $R^3$ is chosen from hydrogen and $(C_1-C_3)$alkyl. In still other embodiments, $R^1$ is a fluoro$(C_1-C_3)$alkyl group.

In some embodiments, $R^2$ is hydrogen. In other embodiments, $R^2$ is a $(C_1-C_3)$alkyl group, in particular, methyl. In yet other embodiments, $R^2$ is $CH_2CH_2$—$OR^3$, wherein $R^3$ is again chosen from hydrogen and $(C_1-C_3)$alkyl. In still other embodiments, $R^2$ and $R^{30}$ form a 4- to 6-membered aliphatic ring.

In some embodiments, $R^4$ is hydrogen. In other embodiments, $R^4$ is a halogen. In yet other embodiments, $R^4$ is $(C_1-C_3)$alkoxy. In still other embodiments, $R^4$ is cyano.

In some embodiments, $R^4$ is an optionally substituted monocyclic heterocyclyl ring. In other embodiments, $R^4$ is an optionally substituted phenyl ring. In yet other embodiments, $R^4$ is an optionally substituted bicyclic heterocyclyl ring. In still other embodiments, $R^4$ is an amino$(C_1-C_3)$alkyl group.

For some embodiments where $R^4$ is an optionally substituted monocyclic heterocyclyl ring, said optional substituents are chosen from one or more of a $(C_1-C_3)$alkyl, amino group, a cyano substituent, a $(C_1-C_3)$alkylamino group, a $(C_1-C_3)$alkoxy group, an oxo substituent, a fluoro$(C_1-C_3)$ alkyl group, a halogen substituent, a hydroxy substituent, and a hydroxy$(C_1-C_3)$alkyl group.

For some embodiments where $R^4$ is an optionally substituted monocyclic heterocyclyl ring, said monocyclic heterocyclyl ring is an optionally substituted monocyclic heteroaryl ring. In some of these embodiments, said optional substituents are chosen from one or more of: an amino substituent, a halogen substituent, a methyl group, a difluoromethyl group, a methoxy group, and a cyano substituent.

For some embodiments where $R^4$ is an optionally substituted monocyclic heteroaryl ring, the monocyclic heteroaryl ring is chosen from furan, thiophene, pyrrole, pyrazole, oxazole, oxadiazole, thiazole, isoxazole, isothiazole, imidazole, triazole, pyridine, pyrimidine, pyrazine, and pyridazine.

In some embodiments where $R^4$ is an optionally substituted monocyclic heteroaryl ring, the substituted monocyclic heteroaryl ring is

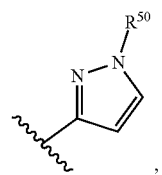

, wherein $R_{50}$ is $(C_1-C_3)$alkyl or fluoro$(C_1-C_3)$alkyl. In some of these embodiments, $R^4$ is

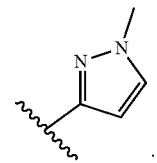

.

For the embodiments where $R^4$ is an optionally substituted phenyl ring, said optional substituents are chosen from one or more of: an amino substituent (in particular, para-amino), a $(C_1-C_3)$alkylamino group, a meta-$(C_1-C_3)$dialkylamino group, a $(C_1-C_3)$alkoxy group (in particular, methoxy), a hydroxy substituent (in particular, ortho- or meta-hydroxy), a halogen substituent (in particular, fluoro), an ortho-cyano substituent, a meta-cyano substituent, an aminocarbonyl group (in particular, meta-aminocarbonyl), a 1,2-methylenedioxy ring, a 1,2-ethylenedioxy ring, a $(C_1-C_3)$acylamino group, a fluoro$(C_1-C_3)$acylamino group, and a hydroxy$(C_1-C_3)$alkylaminosulfonyl group.

For the embodiments where $R^4$ is an optionally substituted bicyclic heterocyclyl ring, said optional substituents are chosen from one or more of: a $(C_1-C_3)$alkyl group, a hydroxy substituent, and an oxo substituent.

For some embodiments where $R^4$ is an optionally substituted bicyclic heterocyclyl ring, the bicyclic heterocyclyl ring is chosen from: indole, isoindole, benzimidazole, benzofuran, benzothiophene, benzooxadiazole, benzothiazole, pyrazolopyridine, quinoline, isoquinoline, quinazoline, quinoxaline, benzodioxole, dihydrobenzooxazine, and purine.

In some embodiments, $R^4$ is a $(C_1-C_3)$alkylamino$(C_1-C_3)$alkyl group. In other embodiments, $R^4$ is a $(C_1-C_3)$dialkylamino$(C_1-C_3)$alkyl group. In yet other embodiments, $R^4$ is a $(C_1-C_3)$alkoxy$(C_1-C_3)$alkyl group. In still other embodiments, $R^4$ is $(C_1-C_6)$hydrocarbyl group.

In some embodiments, $R^4$ is a heterocyclyl$(C_1-C_3)$alkyl group. In other embodiments, $R^4$ is a benzyl group. In yet other embodiments, $R^4$ is a heterocyclyl-substituted benzyl group. In still other embodiments, $R^4$ is a $(C_1-C_3)$alkylaminocarbonyl or a $(C_1-C_3)$acylamino group.

In some embodiments, $R^5$ is hydrogen. In other embodiments, $R^5$ is a halogen substituent. In yet other embodiments, $R^5$ is a $(C_1-C_3)$alkyl group. In still other embodiments, $R^5$ is a $(C_1-C_3)$alkoxy group.

In some embodiments, $R^5$ is a fluoro$(C_1-C_3)$alkyl group, in particular, trifluoromethyl. In other embodiments, $R^5$ is a fluoro$(C_1-C_3)$alkoxy group, In yet other embodiments, $R^5$ is a cyano substituent. In still other embodiments, $R^5$ is

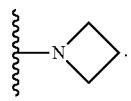

In some embodiments, $R^6$ is hydrogen. In other embodiments, $R^6$ is a halogen substituent, in particular, bromo, chloro or fluoro. In yet other embodiments, $R^6$ is a cyano substituent, preferably when $R^7$ is not a cyano substituent as well. In still other embodiments, $R^6$ is chosen from a —C≡CH, —CH=CH$_2$, methyl, and trifluoromethyl group.

In some embodiments, $R^7$ is hydrogen. In other embodiments, $R^7$ is a halogen substituent, in particular chloro or fluoro. In yet other embodiments, $R^7$ is a cyano substituent, preferably when $R^6$ is not a cyano substituent as well. In still other embodiments, $R^7$ is a $(C_1-C_3)$alkoxy group, in particular methoxy.

In some embodiments, $R^7$ is a fluoro$(C_1-C_3)$alkoxy group. In other embodiments, $R^7$ is a $(C_1-C_3)$alkyl group. In yet other embodiments, $R^7$ is a fluoro$(C_1-C_3)$alkyl group, in particular trifluoromethyl.

In some embodiments, $R^{20}$ is hydrogen. In other embodiments, $R^{20}$ is a $(C_1-C_3)$alkyl group, in particular methyl. In some embodiments, $R^{21}$ is hydrogen. In other embodiments, $R^{21}$ is a $(C_1-C_3)$alkyl group, in particular methyl. In some embodiments, $R^{20}$ and $R^{21}$, together with the carbon to which they are attached form a 3- to 5-membered aliphatic carbocyclic ring.

In some embodiments, $R^{30}$ is hydrogen. In other embodiments, $R^{30}$ and $R^2$ form a 4- to 6-membered aliphatic ring.

In some embodiments, n is 1. In other embodiments, n is 2.

In summary, the invention relates to:

[1] A compound of formula I or II.

[2] A compound according to [1] above wherein $R^1$ is hydrogen.

[3] A compound according to [1] above wherein $R^1$ is $(C_1-C_3)$alkyl.

[4] A compound according to [1] above wherein $R^1$ is CH$_2$CH$_2$—OR$^3$ and $R^3$ is chosen from hydrogen and $(C_1-C_3)$alkyl.

[5] A compound according to [1] above wherein $R^1$ is a fluoro$(C_1-C_3)$alkyl group.

[6] A compound according to any of [1] through [5] above wherein $R^2$ is hydrogen.

[7] A compound according to any of [1] through [5] above wherein $R^2$ is $(C_1-C_3)$alkyl.

[8] A compound according to any of [1] through [5] above wherein $R^2$ is CH$_2$CH$_2$—OR$^3$ and $R^3$ is chosen from hydrogen and $(C_1-C_3)$alkyl.

[9] A compound according to any of [1] through [8] above wherein $R^4$ is hydrogen.

[10] A compound according to any of [1] through [8] above wherein $R^4$ is halogen.

[11] A compound according to any of [1] through [8] above wherein $R^4$ is $(C_1-C_3)$alkoxy.

[12] A compound according to any of [1] through [8] above wherein $R^4$ is cyano.

[13] A compound according to any of [1] through [8] above wherein $R^4$ is an optionally substituted monocyclic heterocyclyl ring, said optional substituents are chosen from one or more of: a $(C_1-C_3)$alkyl, amino group, a cyano substituent, a $(C_1-C_3)$alkylamino group, a $(C_1-C_3)$alkoxy group, an oxo substituent, a fluoro$(C_1-C_3)$alkyl group, a halogen substituent, a hydroxy substituent, and a hydroxy $(C_1-C_3)$alkyl group.

[14] A compound according to any of [1] through [8] above wherein $R^4$ is an optionally substituted phenyl ring, said optional substituents are chosen from one or more of: an amino substituent (in particular para-amino), a $(C_1-C_3)$alkylamino group, a meta-$(C_1-C_3)$dialkylamino group, a $(C_1-C_3)$alkoxy group (in particular methoxy), a hydroxy substituent (in particular ortho- or meta-hydroxy), a halogen substituent (in particular fluoro), an ortho-cyano substituent, a meta-cyano substituent, an aminocarbonyl group (in particular meta-aminocarbonyl), a 1,2-methylenedioxy ring, a 1,2-ethylenedioxy ring, a $(C_1-C_3)$acylamino group, a fluoro$(C_1-C_3)$acylamino group, and a hydroxy$(C_1-C_3)$alkylaminosulfonyl group.

[15] A compound according to any of [1] through [8] above wherein $R^4$ is an optionally substituted bicyclic heterocyclyl ring, said optional substituents are chosen from one or more of: a $(C_1-C_3)$alkyl group, a hydroxy substituent, and an oxo substituent.

[16] A compound according to any of [1] through [8] above wherein $R^4$ is an amino$(C_1-C_3)$alkyl group.

[17] A compound according to any of [1] through [8] above wherein $R^4$ is an optionally substituted monocyclic heteroaryl ring, said optional substituents are chosen from one or more of: an amino substituent, a halogen substituent, a methyl group, a difluoromethyl group, a methoxy group, and a cyano substituent.

[18] A compound according to any of [1] through [8], [13], and [17] above wherein $R^4$ is an optionally substituted monocyclic heteroaryl ring chosen from furan, thiophene, pyrrole, pyrazole, oxazole, oxadiazole, thiazole, isoxazole, isothiazole, imidazole, triazole, pyridine, pyrimidine, pyrazine, and pyridazine.

[19] A compound according to any of [1] through [8], [13], and [17]-[18] above wherein $R^4$ is

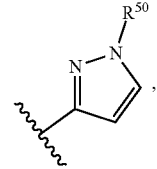

wherein $R_{50}$ is $(C_1-C_3)$alkyl or fluoro$(C_1-C_3)$alkyl.

[20] A compound according to any of [1] through [8], [13], and [17]-[18] above wherein $R^4$ is

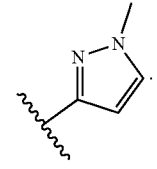 [SMILES: *c1ccn(C)n1]

[21] A compound according to any of [1] through [8] above wherein $R^4$ is a $(C_1-C_3)$alkylamino$(C_1-C_3)$alkyl group.

[22] A compound according to any of [1] through [8] above wherein $R^4$ is a $(C_1-C_3)$dialkylamino$(C_1-C_3)$alkyl group.

[23] A compound according to any of [1] through [8] above wherein $R^4$ is a $(C_1-C_3)$alkoxy$(C_1-C_3)$alkyl group.

[24] A compound according to any of [1] through [23] above wherein $R^5$ is hydrogen.

[25] A compound according to any of [1] through [23] above wherein $R^5$ is a halogen substituent.

[26] A compound according to any of [1] through [23] above wherein $R^5$ is a $(C_1-C_3)$alkyl group.

[27] A compound according to any of [1] through [23] above wherein $R^5$ is a $(C_1-C_3)$alkoxy group.

[28] A compound according to any of [1] through [23] above wherein $R^5$ is a fluoro$(C_1-C_3)$alkyl group.

[29] A compound according to any of [1] through [23] above wherein $R^5$ is a fluoro$(C_1-C_3)$alkoxy group.

[30] A compound according to any of [1] through [23] above wherein $R^5$ is a cyano substituent.

[31] A compound according to any of [1] through [30] above wherein $R^6$ is hydrogen.

[32] A compound according to any of [1] through [30] above wherein $R^6$ is bromo, fluoro or chloro.

[33] A compound according to any of [1] through [30] above wherein $R^6$ is a cyano substituent.

[34] A compound according to any of [1] through [33] above wherein $R^7$ is hydrogen.

[35] A compound according to any of [1] through [33] above wherein $R^7$ is fluoro or chloro.

[36] A compound according to any of [1] through [33] above wherein $R^7$ is a cyano substituent.

[37] A compound according to any of [1] through [36] above wherein $R^{20}$ is a hydrogen.

[38] A compound according to any of [1] through [36] above wherein $R^{20}$ is a methyl group.

[39] A compound according to any of [1] through [36] above wherein $R^{21}$ is a hydrogen.

[40] A compound according to any of [1] through [36] above wherein $R^{21}$ is a methyl group.

[41] A compound according to any of [1] through [36] above wherein $R^{20}$ and $R^{21}$, together with the carbon to which they are attached, form a 3- to 5-membered aliphatic carbocyclic ring.

Throughout this specification the terms and substituents retain their definitions. The description provided herein uses certain terms known in the chemical arts. Unless otherwise specified throughout the description herein, terms retain their meaning as understood by one having ordinary skill in the art.

As used herein, the terms "comprising" and "including" or grammatical variants thereof are to be taken as specifying the stated features, integers, steps or components, but do not preclude the addition of one or more additional features, integers, steps, components or groups thereof. This term encompasses the terms "consisting of" and "consisting essentially of". The phrase "consisting essentially of" or grammatical variants thereof, when used herein, is to be taken as specifying the stated features, integers, steps or components, but does not preclude the addition of one or more additional features, integers, steps, components or groups thereof, but only if the additional features, integers, steps, components or groups thereof do not materially alter the basic and novel characteristics of the claimed composition or method.

As used herein, the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method that "comprises", "has", "includes" or "contains" one or more steps or elements possesses those one or more steps or elements, but is not limited to possessing only those one or more steps or elements.

"Hydrocarbon" (or "hydrocarbyl" when it is a residue) includes alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Hydrocarbyl refers to any substituent comprised of hydrogen and carbon as the only elemental constituents. A prefix such as "$C_x-C_y$" or "$(C_x-C_y)$" indicates that the group following the prefix has from x toy carbon atoms. For example, a "$C_1$ to $C_{20}$ hydrocarbon" indicates a hydrocarbon having 1 to 20 carbon atoms. Aliphatic hydrocarbons are hydrocarbons that are not aromatic; they may be saturated or unsaturated, cyclic, linear or branched. Examples of aliphatic hydrocarbons include isopropyl, 2-butenyl, 2-butynyl, cyclopentyl, norbornyl, etc. Aromatic hydrocarbons include benzene (phenyl), naphthalene (naphthyl), anthracene, etc.

Unless otherwise specified, alkyl (or alkylene when divalent) is intended to include linear or branched saturated hydrocarbon structures and combinations thereof. Unless otherwise defined, "alkyl" refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include cyclopropyl, cyclobutyl, cyclopentyl, norbornyl and the like.

Unless otherwise specified, the term "carbocycle" is intended to include ring systems in which the ring atoms are all carbon but of any oxidation state. Thus $(C_3-C_{10})$ carbocycle refers to both non-aromatic and aromatic systems, including such systems as cyclopropane, benzene and cyclohexene; $(C_8-C_{12})$ carbopolycycle refers to such systems as norbornane, decalin, indane and naphthalene. Carbocycle, if not otherwise limited, refers to monocycles, bicycles and polycycles.

Heterocycle means an aliphatic or aromatic carbocycle residue in which from one to four carbons has been replaced by a heteroatom selected from the group consisting of N, O, and S. Unless otherwise specified, a heterocycle may be non-aromatic (heteroaliphatic) or aromatic (heteroaryl). Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, benzoxazolyl, tetrahydrofuryl, tetrahydropyranyl, thienyl (also historically called thiophenyl), benzothienyl, thiamorpholinyl, oxadiazolyl, triazolyl and tetrahydroquinolinyl.

Monocyclic heterocyclyl or monocyclic heterocycle means an aromatic or non-aromatic heterocycle composed of a single ring. Examples of monocyclic heterocycles include furan, thiophene, pyrrole, pyrazole, oxazole, oxadiazole, thiazole, isoxazole, isothiazole, imidazole, triazole, pyridine, pyrimidine, pyrazine, and pyridazine. Bicyclic heterocyclyl means an aromatic or non-aromatic heterocycle composed of two fused rings wherein one or both of the rings contain a heteroatom. Thus, bicyclic heterocyclyl includes fused bicyclic structures that have no heteroatom in one ring but contain one or more heteroatoms in the other ring. Neither ring need be aromatic but one or both rings may be aromatic. However, if at least one ring is aromatic, then the bicyclic heterocyclyl is considered aromatic. Examples of bicyclic heterocycles include indole, isoindole, benzimidazole, benzofuran, benzothiophene, benzooxadiazole, benzothiazole, pyrazolopyridine, quinoline, isoquinoline, quinazoline, quinoxaline, benzodioxole, dihydrobenzooxazine, and purine.

Hydrocarbyloxy refers to groups of from 1 to 20 carbon atoms, preferably 1 to 10 carbon atoms, more preferably 1 to 6 carbon atoms attached to the parent structure through an oxygen. Alkoxy is a subset of hydrocarbyloxy and includes groups of a straight or branched configuration. Examples include methoxy, ethoxy, propoxy, isopropoxy and the like. Lower-alkoxy refers to groups containing one to four carbons. The term "halogen" means fluorine, chlorine, bromine or iodine atoms.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Lower-acyl refers to groups containing one to four carbons.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxy lower alkyl, carbonyl, phenyl, heteroaryl, benzenesulfonyl, hydroxy, lower alkoxy, haloalkoxy, oxaalkyl, carboxy, alkoxycarbonyl [—C(=O)O-alkyl], alkoxycarbonylamino [HNC(=O)O-alkyl], aminocarbonyl (also known as carboxamido) [—C(=O)NH$_2$], oxo [=O]alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine.

Substituents R" are generally defined when introduced and retain that definition throughout the specification and in all independent claims.

Preparation of compounds can involve the protection and deprotection of various chemical groups. The need for protection and deprotection, and the selection of appropriate protecting groups, can be readily determined by one skilled in the art. Suitable groups for that purpose are discussed in standard textbooks in the field of chemistry, such as Protective Groups in Organic Synthesis by T. W. Greene and P. G. M. Wuts [John Wiley & Sons, New York, 1999], in *Protecting Group Chemistry*, 1$^{st}$ Ed., Oxford University Press, 2000; and in *March's Advanced Organic chemistry: Reactions, Mechanisms, and Structure*, 5$^{th}$ Ed., Wiley-Interscience Publication, 2001.

One or more compounds described herein contain up to two asymmetric centers and may thus give rise to enantiomers, diastereomers, and other stereoisomeric forms which may be defined in terms of absolute stereochemistry as (R)- or (S)-. The present invention is meant to include all such possible isomers as racemates, optically pure forms and intermediate mixtures. Optically active isomers may be prepared using homo-chiral synthons or homo-chiral reagents, or optically resolved using conventional techniques such as chiral chromatography. All tautomeric forms are intended to be included. The graphic representations of racemic, ambiscalemic and scalemic or enantiomerically pure compounds used herein are taken from Maehr *J. Chem. Ed.* 62, 114-120 (1985): simple, single bond lines convey connectivity only and no stereochemical implication; solid and broken wedges are used to denote the absolute configuration of a chiral element; wavy lines indicate explicit disavowal of any stereochemical implication which the bond it represents could generate; solid and broken bold lines are geometric descriptors indicating the relative configuration shown but do not denote absolute configurations; and wedge outlines and dotted or broken lines denote enantiomerically pure compounds of indeterminate absolute configuration. Enantiomerically pure means greater than 80 e.e., and preferably greater than 90 e.e.

For example, a generic structure depicting exemplary compounds of the invention is depicted as follows when R$^2$ is hydrogen:

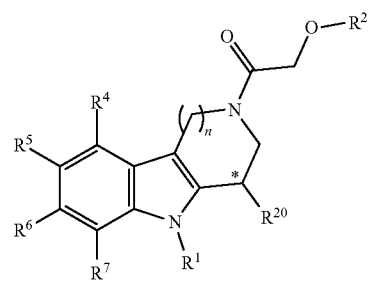

This structure contains a single asymmetric center (labeled with an asterisk). In one embodiment, this structure can be represented as:

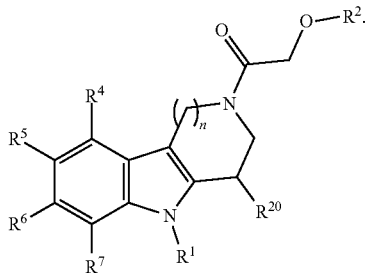

This depiction only indicates connectivity regarding the atoms bonded to the chiral center. The compound represented in this case may be any mixture of R and S enantiomers, from 100% R to 100% S, and any ratio between.

Individual enantiomers are drawn as follows:

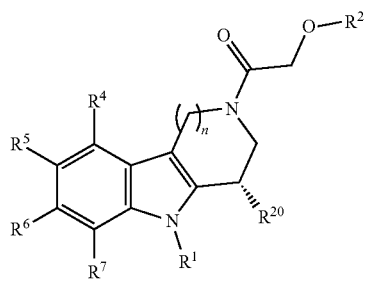

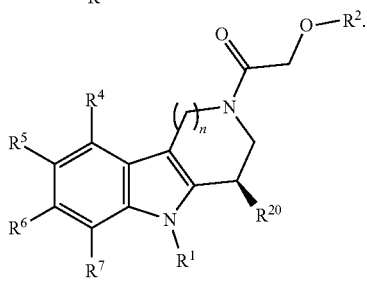

When $R^{20}$ is $(C_1-C_3)$alkyl, the structure on the left indicates that the compound is enantiomerically enriched with the S enantiomer (greater than 90:10 S:R or >80% e.e. S) and the structure on the right indicates that the compound is enantiomerically enriched with the R enantiomer (greater than 90:10 R:S or >80% e.e. R). For structures depicted using this convention, the absolute configuration is known to be as shown.

When the absolute stereochemistry is not known, but the compounds are known to be enantiomerically enriched (>80% e.e.), the structures are drawn as follows:

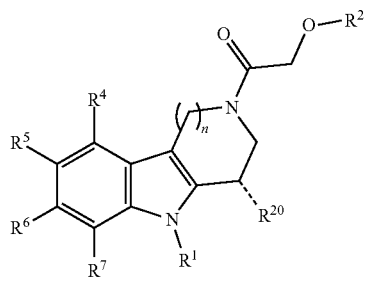

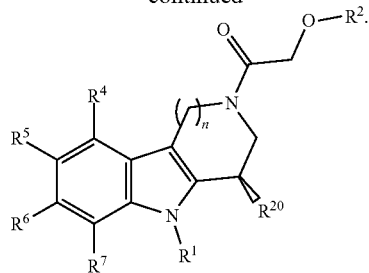

For these structures using this convention, the compounds are enantiomerically enriched (>80% e.e.), but the absolute stereochemistry is unknown. All that is known is that the major isomers are mirror images of each other at the specified e.e. This situation is typically the result of exposure to a chiral environment that leads to enantiomeric enrichment.

As used herein, the terms "treatment" or "treating," or "palliating" or "ameliorating" refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological systems associated with the underlying disorder such that an improvement is observed in the patient, notwithstanding that the patient may still be afflicted with the underlying disorder. In particular, in the case of treating SLE, one considers family predispositions. Thus, if there is a family with three children, two of whom have SLE and anti dsDNA antibodies, if the 3rd child displays dsDNA antibodies but hasn't yet disease symptoms, clinicians would treat the asymptomatic child because of the genetic background.

As used herein, and as would be understood by the person of skill in the art, the recitation of "a compound"—unless expressly further limited—is intended to include salts of that compound. In a particular embodiment, the term "compound of formula" refers to the compound or a pharmaceutically acceptable salt thereof.

The term "pharmaceutically acceptable salt" refers to salts prepared from pharmaceutically acceptable non-toxic acids or bases including inorganic acids and bases and organic acids and bases. When the compounds of the present invention are basic—as they are in most cases—salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic functionality (e.g. —$SO_3H$), suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

Also provided herein is a pharmaceutical composition comprising a compound disclosed above, or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula I or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

EXPERIMENTAL SECTION

Some compounds x of the invention, wherein $R^4$ is aryl or heteroaryl, can be prepared as described below in Synthetic Routes A1 or A2. Synthetic Route A2 is preferred for multi-gram synthesis.

Synthetic Route A1

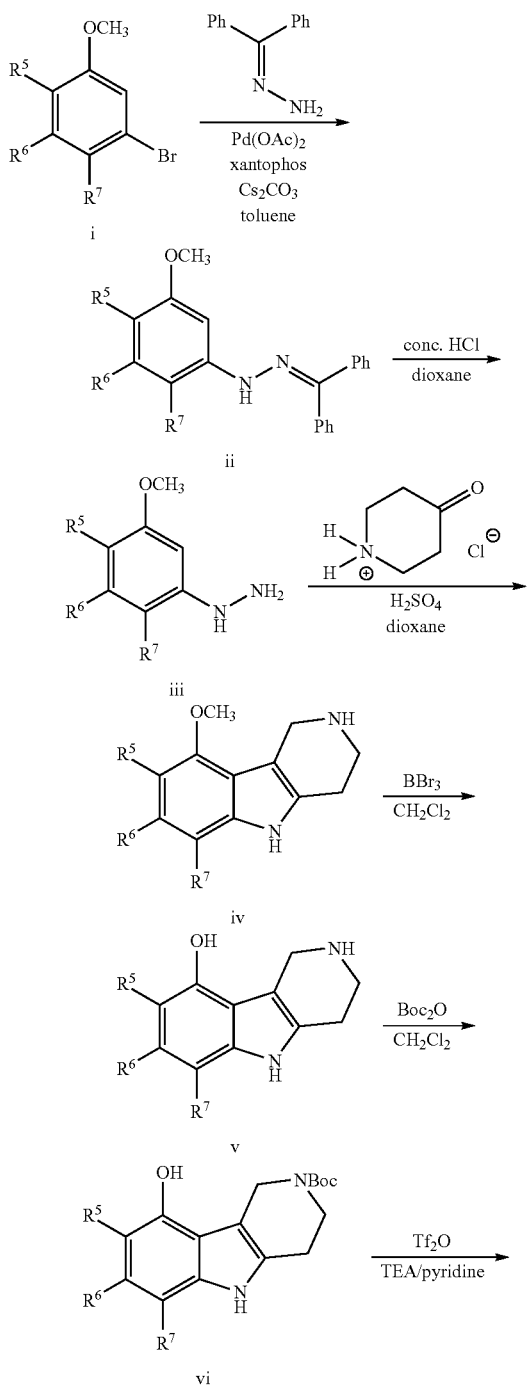

-continued

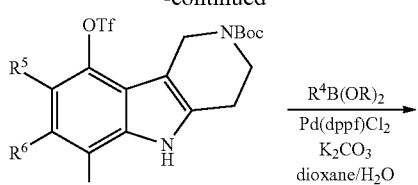

vii

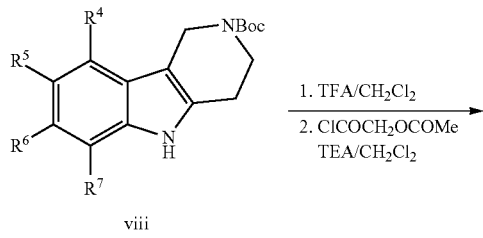

viii

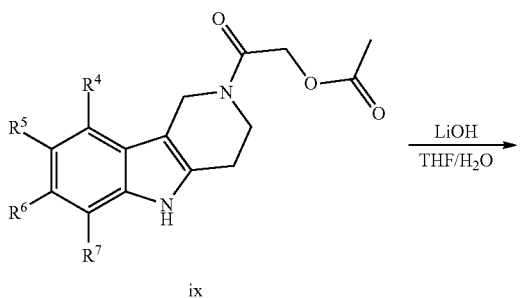

ix

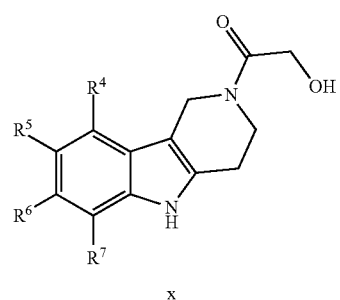

x

Palladium-catalyzed coupling of i with benzophenone hydrazone provides ii, which is hydrolyzed to hydrazine iii. Hydrazine iii is cyclized with piperidinone to provide tetrahydropyrido[4,3-b]indole iv. The tetrahydropyrido[4,3-b]indole iv is demethylated to 4-hydroxy v, N-protected with Boc (vi), and activated with triflic anhydride to provide vii. The triflate vii is coupled with a pinacol boronate reagent via Suzuki-Miyaura coupling to incorporate $R^4$ into viii. The Boc group is cleaved and replaced by the protected hydroxyacetyl side chain via its acid chloride to provide the acetyl-protected product ix. The acetyl is cleaved from the acetyl-protected product ix by treatment with aqueous lithium hydroxide to provide the 1-(3,4-dihydro-1H-pyrido[4,3-b]indol-2(5H)-yl)-2-hydroxyethanone x.

An example synthesis is provided for illustration:

1-(6,7-Dichloro-9-(1H-pyrazol-4-yl)-1,3,4,5-tetrahydro-2H-pyrido[4,3-b]indol-2-yl)-2-hydroxyethan-1-one

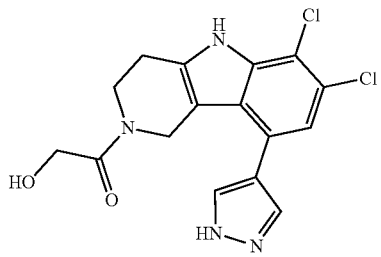 [SMILES: O=C(CO)N1CCc2[nH]c3c(Cl)c(Cl)cc(-c4cn[nH]c4)c3c2C1]

To a solution of 1-bromo-3-chloro-5-methoxybenzene (20 g, 90.3 mmol) in dimethyl formamide (100 mL) was added trichloroisocyanuric acid (7.56 g, 32.5 mmol) at 25° C. The mixture was stirred for 12 h at 50° C. The mixture was poured into water (200 mL). The aqueous phase was extracted with ethyl acetate (2×100 mL). The combined organic layers were washed with brine (3×100 mL), dried over anhydrous sodium sulfate, and filtered. The filtrate was concentrated under vacuum. The residue was triturated with petroleum ether (20 mL) at 0° C. The solid was collected by filtration to obtain 1-bromo-2, 3-dichloro-5-methoxybenzene. $^1$H NMR: (CDCl$_3$, 400 MHz) δ 7.12 (d, J=2.8 Hz, 1H), 7.00 (d, J=2.8 Hz, 1H), 3.79 (s, 3H).

To a mixture of 1-bromo-2, 3-dichloro-5-methoxybenzene (20 g, 78.1 mmol), benzophenone hydrazone (18.4 g, 93.8 mmol), Xantphos (7.45 g, 12.9 mmol) and cesium carbonate (63.7 g, 196 mmol) in toluene (200 mL) was added palladium acetate (1.75 g, 7.79 mmol) at 25° C. under nitrogen. The mixture was stirred for 10 h at 100° C. under nitrogen. The mixture was cooled to 30° C. and filtered. The filtrate was concentrated. The residue was purified by column chromatography (SiO$_2$, petroleum ether=1) to obtain 1-(2, 3-dichloro-5-methoxyphenyl)-2-(diphenylmethylene) hydrazine. $^1$H NMR: (CDCl$_3$, 400 MHz) δ 8.12 (brs, 1H), 7.65-7.55 (m, 5H), 7.39-7.34 (m, 5H), 7.25 (d, J=4.0 Hz, 1H), 6.53 (d, J=4.0 Hz, 1H), 3.86 (s, 3H). LCMS: m/z 371.0, 373.0 [M+H]$^+$ A solution of 1-(2, 3-dichloro-5-methoxyphenyl)-2-(diphenylmethylene)hydrazine (7.0 g, 18.9 mmol) in dioxane (60 mL) and conc. hydrochloric acid (12 M, 15 mL) was stirred for 1 h at 100° C. The mixture was cooled to 0° C., and the pH was adjusted to 8 by the addition of a saturated sodium bicarbonate solution. The aqueous phase was extracted with ethyl acetate (3×150 mL). The combined organic layers were washed with brine (200 mL), dried over anhydrous sodium sulfate, and filtered. The filtrate was concentrated under vacuum. The residue was purified by silica gel chromatography (petroleum ether:ethyl acetate=20:15:1) to give 1-(2, 3-dichloro-5-methoxyphenyl) hydrazine. $^1$H NMR: (DMSO-d$_6$, 400 MHz) δ 6.83 (brs, 1H), 6.72 (d, J=4.0 Hz, 1H), 6.41 (d, J=3.2 Hz, 1H), 4.21 (brs, 2H), 3.73 (s, 3H). LCMS: m/z 207.0, 208.9 [M+H]$^+$ To a solution of 1-(2, 3-dichloro-5-methoxyphenyl)hydrazine (6.5 g, 31.4 mmol) and 4-piperidone (5.11 g, 37.7 mmol, HCl salt) in dioxane (70 mL) was added concentrated sulfuric acid (9.02 g, 92.0 mmol, 4.9 mL) at 0° C. The mixture was stirred for 12 h at 80° C. The mixture was concentrated under vacuum. The residue was diluted with water (20 mL), and the pH was adjusted to 9 by the addition of an aqueous sodium hydroxide solution (2 M) at 0° C. The formed precipitate was collected by filtration. The precipitate was triturated with ethyl acetate (15 mL) to give 6, 7-dichloro-2, 3, 4, 5-tetrahydro-9-methoxy-1H-pyrido[4, 3-b]indole. $^1$H NMR: (DMSO-$d_6$, 400 MHz) δ 11.64 (br.s, 1H), 6.73 (s, 1H), 4.30 (s, 2H), 3.86 (s, 3H), 3.56 (s, 2H), 2.96 (s, 2H). LCMS: m/z 271.0, 273.0 [M+H]$^+$ To a solution of 6, 7-dichloro-2, 3, 4, 5-tetrahydro-9-methoxy-1H-pyrido[4, 3-b]indole (2.0 g, 7.38 mmol) in dichloromethane (50 mL) was added boron tribromide (5.30 g, 21.2 mmol) at 0° C. The mixture was stirred at 25° C. for 12 h. The mixture was concentrated under reduced pressure. The residue was poured into a saturated aqueous sodium bicarbonate solution (30 mL). The mixture was extracted with ethyl acetate (3×30 mL). The combined organic layers were washed with brine (10 mL), dried over anhydrous sodium sulfate, and filtered. The filtrate was concentrated under vacuum to obtain 6, 7-dichloro-2, 3, 4, 5-tetrahydro-1H-pyrido[4, 3-b]indol-9-ol. $^1$H NMR: (DMSO-$d_6$, 400 MHz) δ 11.48 (brs, 1H), 6.61 (s, 1H), 4.33 (s, 2H), 3.39-3.35 (m, 2H), 3.00-3.97 (m, 2H).

To a solution of 6, 7-dichloro-2, 3, 4, 5-tetrahydro-1H-pyrido[4, 3-b]indol-9-ol (1 g, 3.89 mmol) and triethylamine (1.18 g, 11.7 mmol, 1.62 mL) in tetrahydrofuran (20 mL) was added Boc$_2$O (679 mg, 3.11 mmol, 715 μL) at 25° C. The mixture was stirred for 1 h at 25° C. The mixture was poured into ice-water (40 mL). The mixture was extracted with ethyl acetate (3×20 mL). The combined organic layers were washed with brine (2×20 mL), dried over anhydrous sodium sulfate, and filtered. The filtrate was concentrated under vacuum. The residue was purified by column chromatography (SiO$_2$, petroleum ether: ethyl acetate=10:1 to 3:1) to give tert-butyl 6, 7-dichloro-3, 4-dihydro-9-hydroxy-1H-pyrido[4, 3-b]indole-2(5H)-carboxylate. $^1$H NMR: (CDCl$_3$, 400 MHz) δ 8.16 (brs, 1H), 7.90 (brs, 1H), 6.48 (s, 1H), 4.83 (s, 2H), 3.81 (t, J=6.0 Hz, 2H), 2.85-2.81 (m, 2H), 1.59 (s, 9H). LCMS: m/z 379.0 [M+Na]$^+$ To a solution of tert-butyl 6, 7-dichloro-3, 4-dihydro-9-hydroxy-1H-pyrido[4, 3-b]indole-2(5H)-carboxylate (700 mg, 1.96 mmol) in pyridine (5 mL) and dichloromethane (10 mL) was added Tf$_2$O (1.11 g, 3.93 mmol, 647 μL) at 0° C. The mixture was stirred for 1 h at 25° C. The mixture was poured into ice-water (30 mL). The mixture was extracted with ethyl acetate (2×20 mL). The combined organic layers were washed with aqueous hydrochloric acid (1 M, 20 mL) and brine (2×10 mL). The organic layer was dried over anhydrous sodium sulfate, filtered, and concentrated under vacuum to obtain tert-butyl 6, 7-dichloro-9-(((trifluoromethyl)sulfonyl)oxy)-1, 3, 4, 5-tetrahydro-2H-pyrido[4, 3-b]indole-2-carboxylate. $^1$H NMR: (CDCl$_3$, 400 MHz) δ 8.43 (brs, 1H), 7.16 (s, 1H), 4.76 (s, 2H), 3.83 (t, J=5.6 Hz, 2H), 2.89-2.87 (m, 2H), 1.51 (s, 9H). LCMS: m/z 432.9, 434.9 [MS-55]$^+$ To a mixture of tert-butyl 6, 7-dichloro-9-(((trifluoromethyl)sulfonyl)oxy)-1, 3, 4, 5-tetrahydro-2H-pyrido[4, 3-b]indole-2-carboxylate (200 mg, 409 μmol), 4-(4, 4, 5, 5-tetramethyl-1, 3, 2-dioxaborolan-2-yl)-1H-pyrazole (119 mg, 613 μmol) and potassium carbonate (169 mg, 1.22 mmol) in dioxane (10 mL) and water (3 mL) was added Pd(dppf)Cl$_2$·CH$_2$Cl$_2$ (33 mg, 40 μmol) at 25° C. under nitrogen. The mixture was stirred for 10 h at 80° C. The mixture was filtered, and the filtrate was poured into water (20 mL). The mixture was extracted with ethyl acetate (3×15 mL). The combined organic layers were washed with brine (10 mL), dried over anhydrous sodium sulfate, and filtered. The filtrate was concentrated under vacuum. The residue was purified by preparative thin layer chromatography (SiO$_2$, petroleum ether: ethyl acetate=2:1) to obtain tert-butyl 6, 7-dichloro-3, 4-dihydro-9-(1H-pyrazol-4-yl)-1H-pyrido[4, 3-b]indole-2(5H)-carboxylate. $^1$H NMR: (CD$_3$OD, 400 MHz) δ 7.75 (s, 1H), 7.60 (s, 1H), 7.00 (s, 1H), 4.24 (s, 2H), 3.75 (s, 2H), 2.85 (t, J=5.6 Hz, 2H), 1.20 (s, 9H). LCMS: m/z 429.0, 431.0 [M+Na]$^+$ A mixture of tert-butyl 6, 7-dichloro-3, 4-dihydro-9-(1H-pyrazol-4-yl)-1H-pyrido[4, 3-b]indole-2(5H)-carboxylate (150 mg, 368 μmol) in trifluoroacetic acid (3 mL) and dichloromethane (10 mL) was stirred for 10 h at 25° C. The solution was concentrated under vacuum to obtain 6, 7-dichloro-2, 3, 4, 5-tetrahydro-9-(1H-pyrazol-4-yl)-1H-pyrido[4, 3-b]indole-TFA. The material was used in the next step without further purification. $^1$H NMR: (CD$_3$OD, 400 MHz) δ 11.48 (brs, 1H), 8.01 (brs, 1H), 7.99 (s, 1H), 7.81 (s, 2H), 7.10 (s, 1H), 4.06 (s, 2H), 3.58 (t, J=6.4 Hz, 2H), 3.18 (t, J=6.0 Hz, 2H).

To a solution of 6, 7-dichloro-2, 3, 4, 5-tetrahydro-9-(1H-pyrazol-4-yl)-1H-pyrido[4, 3-b]indole-TFA (120 mg, 297 μmol) and triethylamine (119 mg, 1.18 mmol, 163 μL) in dichloromethane (2 mL) was added (chlorocarbonyl)methyl acetate (80 mg, 586 μmol, 63 μL) at 0° C. The mixture was stirred for 0.5 h at 25° C. The residue was poured into a saturated aqueous sodium bicarbonate solution (20 mL) and the mixture stirred for 15 mins. The aqueous phase was extracted with ethyl acetate (3×15 mL). The combined organic layers were washed with brine (10 mL), dried over anhydrous sodium sulfate, and filtered. The filtrate was concentrated under vacuum to give 2-(6, 7-dichloro-3, 4-dihydro-9-(1H-pyrazol-4-yl)-1H-pyrido[4,3-b]indol-2(5H)-yl)-2-oxoethyl acetate which was used in the next step without further purification.

To a solution of 2-(6, 7-dichloro-3, 4-dihydro-9-(1H-pyrazol-4-yl)-1H-pyrido[4, 3-b]indol-2(5H)-yl)-2-oxoethyl acetate (150 mg, 368 μmol) in tetrahydrofuran (3 mL) and water (1 mL) was added lithium hydroxide monohydrate (46 mg, 1.10 mmol) at 25° C. The mixture was stirred for 1 h at 25° C. The mixture was poured into ice-water (20 mL), and the pH was adjusted to 7 by the addition of aqueous hydrochloric acid (1 M). The mixture was extracted with ethyl acetate (3×15 mL). The combined organic layers were washed with brine (2×10 mL), dried over anhydrous sodium sulfate, and filtered. The filtrate was concentrated under vacuum. The residue was purified by preparative thin layer chromatography (ethyl acetate:methanol, 20:1) to obtain 1-(6, 7-dichloro-9-(1H-pyrazol-4-yl)-1, 3, 4, 5-tetrahydro-2H-pyrido[4, 3-b]indol-2-yl)-2-hydroxyethan-1-one. $^1$H NMR: (CD$_3$OD, 400 MHz) δ 7.84 (brs, 1H), 7.73 (brs, 1H), 7.02 (s, 1H), 4.46 (s, 1H), 4.31 (s, 1H), 4.19 (s, 1H), 4.06 (s, 1H), 3.94 (t, J=5.6 Hz, 1H), 3.74 (t, J=5.6 Hz, 1H), 2.89 (t, J=5.6 Hz, 1H), 2.95 (t, J=5.6 Hz, 1H). LCMS: m/z 365.0 [M+H]$^+$ Synthetic Route A2

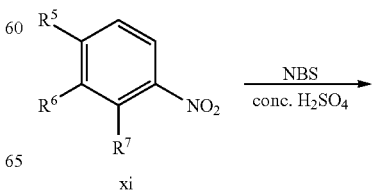

xi

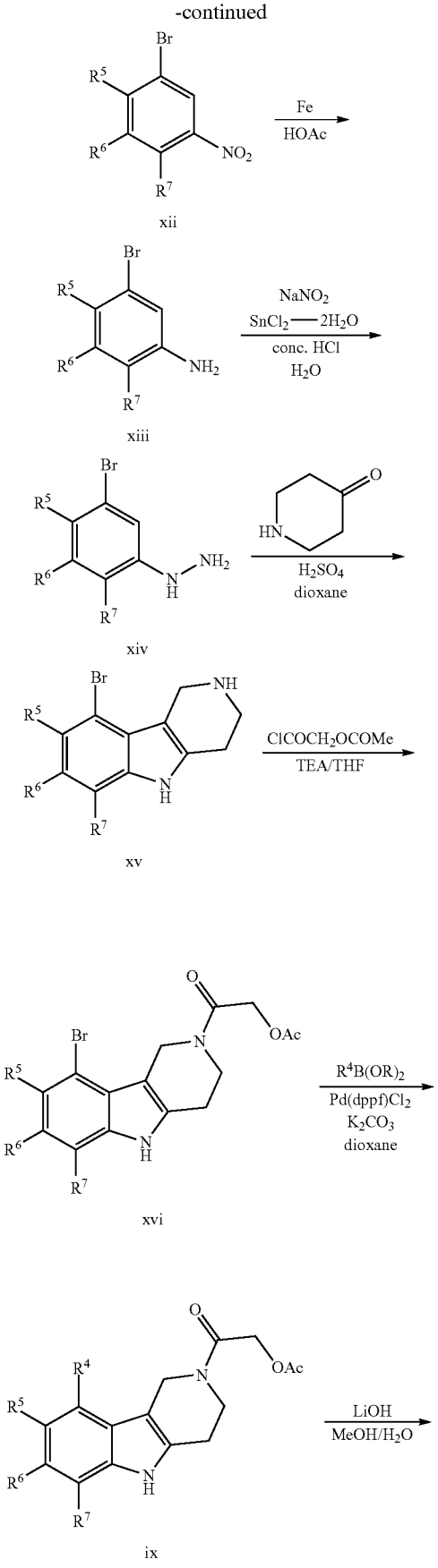

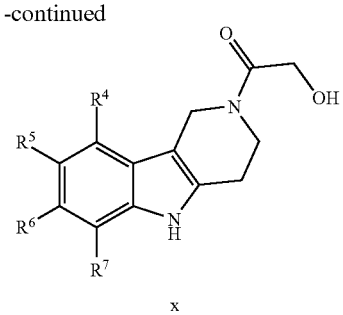

Bromination of optionally substituted-nitrobenzene derivatives xi provide meta-bromo substitution products xii. Reduction with iron provides anilines xiii, which are then converted to hydrazines xiv with sodium nitrite and stannous chloride. Hydrazines xiv undergo Fischer indole synthesis with piperidinone to provide tetrahydropyrido[4, 3-b]indoles xv, which are subsequently capped to provide amides xvi. Suzuki-Miyaura coupling followed by hydrolysis of the acetate protecting group provides compounds x.

An example synthesis is provided for illustration:

1-(7-Chloro-6-fluoro-9-(1-methyl-1H-pyrazol-3-yl)-1,3,4,5-tetrahydro-2H-pyrido[4,3-b]indol-2-yl)-2-hydroxyethan-1-one

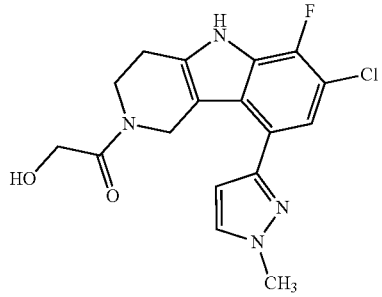 [SMILES: Cn1ccc(-c2cc(Cl)c(F)c3[nH]c4c(c23)CN(C(=O)CO)CC4)n1]

To a solution of 1-chloro-2-fluoro-3-nitrobenzene (120 g, 684 mmol) in $H_2SO_4$ (650 mL) was added NBS (146 g, 820 mmol) at 25° C. Then the reaction mixture was stirred at 65° C. for 4 h. The mixture was cooled to 25° C. The mixture was poured into ice water (2.00 L) and extracted with ethyl acetate (3×500 mL). The combined organic layers were washed with brine (500 mL), dried over anhydrous sodium sulfate, and filtered. The filtrate was concentrated to give 5-bromo-1-chloro-2-fluoro-3-nitrobenzene. $^1H$ NMR: (DMSO-$d_6$, 400 MHz) δ 8.39-8.37 (m, 1H), 8.34-3.33 (m, 1H).

To a solution of 5-bromo-1-chloro-2-fluoro-3-nitrobenzene (89.0 g, 350 mmol) in AcOH (500 mL) was added Fe (58.6 g, 1.05 mol) in portions at 0° C. The mixture was stirred at 25° C. for 16 h. The mixture was poured into water (1.50 L) and filtered. The filter cake was washed with ethyl acetate (5×200 mL). The filtrate was extracted with ethyl acetate (4×500 mL). The combined organic layers were washed with brine (500 mL), dried over anhydrous sodium sulfate, and filtered. The filtrate was concentrated to give a residue. The residue was purified by column chromatography ($SiO_2$, petroleum ether: ethyl acetate=50:1 to 1:1) to give 5-bromo-3-chloro-2-fluoroaniline. $^1H$ NMR: ($CDCl_3$, 400 MHz) δ 6.89-6.87 (m, 1H), 6.82-6.80 (m, 1H), 3.61-3.59 (m, 2H). LC-MS: m/z 225.9 [M+H]+

To a solution of 5-bromo-3-chloro-2-fluoroaniline (50.0 g, 223 mmol) in HCl (12.0 M, 825 mL) was added NaNO₂ (18.9 g, 274 mmol) in water (100 mL) drop-wise at −5° C. under nitrogen. After stirring the reaction mixture at −5~0° C. for 1 h, a solution of SnCl₂·2H₂O (126 g, 558 mmol) in HCl (12.0 M, 825 mL) was added drop-wise at 0° C. The mixture was stirred at 0° C. for 3 h. The reaction mixture was filtered, and the filter cake was washed with water (200 mL). The collected solid was dried to give (5-bromo-3-chloro-2-fluorophenyl)hydrazine-HCl. LC-MS: m/z 240.9 [M+H]+

To a solution of (5-bromo-3-chloro-2-fluorophenyl)hydrazine (85.0 g, 308 mmol, HCl salt) and piperidin-4-one (62.7 g, 462 mmol, HCl salt) in dioxane (1.97 L) was added H₂SO₄ (18 M, 347 mmol). The mixture was stirred at 90° C. for 12 h. The reaction mixture was concentrated to give a residue. The residue was basified (pH=8) with aqueous NaOH along with adequate cooling. The mixture was filtered, and the filter cake was washed with water (100 mL). The collected solid was dried to give 9-bromo-7-chloro-6-fluoro-2, 3, 4, 5-tetrahydro-1H-pyrido[4, 3-b]indole. ¹H NMR: (DMSO-d₆, 400 MHz) δ11.91 (s, 1H), 7.26 (d, J=4.8 Hz, 1H), 4.21 (m, 2H), 3.08 (m, 2H), 2.74 (m, 2H). LC-MS: m/z 304.9 [M+H]+

To a solution of 9-bromo-7-chloro-6-fluoro-2, 3, 4, 5-tetrahydro-1H-pyrido[4, 3-b]indole (40.0 g, 132 mmol) and TEA (40.0 g, 395 mmol, 17.0 mL) in TH (400 mL) was added (2-chloro-2-oxo-ethyl) acetate (21.6 g, 158 mmol, 17.0 mL) at 0° C. The mixture was stirred at 25° C. for 5 h. The reaction mixture was poured into water (200 mL). The mixture was extracted with ethyl acetate (3×300 mL). The combined organic layers were washed with brine (200 mL), dried over anhydrous sodium sulfate, and filtered. The filtrate was concentrated to give a crude residue. The residue was triturated with ethyl acetate (30.0 mL) at 25° C. for 12 h. The mixture was filtered, and the filter cake was dried to give a residue. The residue was purified by chromatography (SiO₂, petroleum ether: ethyl acetate=20:1 to 4:1) to afford 2-(9-bromo-7-chloro-6-fluoro-1, 3, 4, 5-tetrahydro-2H-pyrido[4,3-b]indol-2-yl)-2-oxoethyl acetate. ¹H NMR: (DMSO-d₆, 400 MHz) δ 12.09-12.06 (m, 1H), 7.30 (d, J=5.6 Hz, 1H), 4.92-4.86 (m, 4H), 3.84-3.70 (m, 2H), 2.90-2.77 (m, 2H), 2.09 (s, 3H). LC-MS: m/z 404.9 [M+H]+

To a solution of 2-(9-bromo-7-chloro-6-fluoro-1, 3, 4, 5-tetrahydro-2H-pyrido[4, 3-b]indol-2-yl)-2-oxoethyl acetate (11.0 g, 27.3 mmol), 1-methyl-3-(4,4,5,5-tetramethyl-1, 3, 2-dioxaborolan-2-yl)-1H-pyrazole (5.67 g, 27.2 mmol) and K₂CO₃ (7.53 g, 54.5 mmol) in dioxane (330 mL) was added Pd(dppf)Cl₂ (1.99 g, 2.72 mmol) at 25° C. The mixture was stirred at 100° C. for 12 h under a nitrogen atmosphere. The reaction mixture was filtered, and the filtrate was concentrated to give a residue. The residue was purified by reversed-phase HPLC (FA condition). The eluent was concentrated to remove acetonitrile. The pH of the resulting solution was adjusted to pH=7 with addition of an aqueous of NaHCO₃ solution. The aqueous layer was extracted with CH₂C₂ (3×100 mL), dried over anhydrous sodium sulfate, filtered and concentrated. The residue was triturated with ethyl acetate (20.0 mL) at 25° C. for 3 h (twice) to give 2-(7-chloro-6-fluoro-9-(1-methyl-1H-pyrazol-3-yl)-1, 3, 4, 5-tetrahydro-2H-pyrido[4, 3-b]indol-2-yl)-2-oxoethyl acetate. LC-MS: m/z 405.0 [M+H]+

To a solution of 2-(7-chloro-6-fluoro-9-(1-methyl-1H-pyrazol-3-yl)-1, 3, 4, 5-tetrahydro-2H-pyrido[4, 3-b]indol-2-yl)-2-oxoethyl acetate (4.50 g, 11.1 mmol) in MeOH (50.0 mL) and water (5.00 mL) was added LiOH H₂O (1.32 g, 31.5 mmol) at 25° C. The mixture was stirred at 25° C. for 0.17 h. The crude reaction mixture was concentrated to remove MeOH. The residue was poured into water (75 mL) and the pH was adjusted to 6 with the addition of aqueous HCl solution (1M). The mixture was filtered, and the filter cake was dried to afford 1-(7-chloro-6-fluoro-9-(1-methyl-1H-pyrazol-3-yl)-1, 3, 4, 5-tetrahydro-2H-pyrido[4, 3-b]indol-2-yl)-2-hydroxyethan-1-one. To remove residual Pd from the earlier coupling step, the material was further purified by reverse MPLC (neutral condition). The material was dissolved in EtOH (350 mL), and thiourea resin (6.20 g) was added. The mixture was heated at 80° C. and stirred at 80° C. for 16 h. The mixture was cooled to 25° C. and filtered. The filter cake was washed with EtOH (2×20 mL). To the filtrate was added thiourea resin (3.10 g), and the mixture was heated to 80° C. and stirred at 80° C. for 2 h. The mixture was cooled to 25° C. and filtered. The filter cake was washed with EtOH (2×20 mL). The filtrate was concentrated to afford 1-(7-chloro-6-fluoro-9-(1-methyl-1H-pyrazol-3-yl)-1, 3, 4, 5-tetrahydro-2H-pyrido[4, 3-b]indol-2-yl)-2-hydroxyethan-1-one. ¹H NMR: (DMSO-d₆, 400 MHz) δ 11.82-11.77 (m, 1H), 7.77 (s, 1H), 7.15-7.09 (m, 1H), 6.57-6.52 (m, 1H), 4.58-4.55 (m, 3H), 4.18-4.17 (m, 1H), 4.11-4.10 (m, 1H), 3.95-3.92 (m, 3H), 3.83-3.82 (m, 1H), 3.67-3.64 (m, 1H), 2.88-2.82 (m, 2H) LC-MS: m/z 363.0 [M+H]+

For some compounds of the invention, R⁴ is introduced via an Ullman-type reaction. An example is shown below:

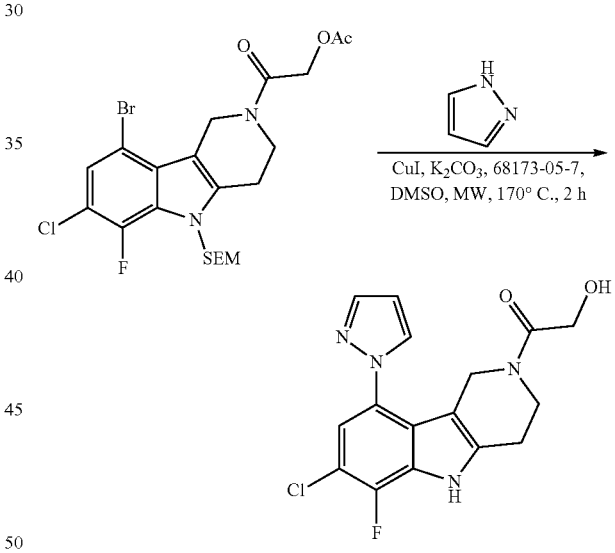

[2-[9-Bromo-7-chloro-6-fluoro-5-(2-trimethylsilylethoxymethyl)-3, 4-dihydro-1H-pyrido[4, 3-b]indol-2-yl]-2-oxoethyl] acetate (0.2 g, 375 μmol), 1H-pyrazole (51 mg, 749 μmol), CuI (71 mg, 375 μmol), K₂CO₃ (104 mg, 749 μmol), and (1S,2S)—N1,N2-dimethylcyclohexane-1,2-diamine (53 mg, 375 μmol) were taken up into a microwave tube in DMSO (3 mL). The sealed tube was heated at 170° C. for 120 min under microwave irradiation. The reaction mixture was partitioned between water (20 mL) and EtOAc (20 mL). The organic phase was separated, washed with EtOAc (3×30 mL), dried over anhydrous sodium sulfate, filtered and concentrated under reduced pressure to give a residue. The residue was purified by preparative-HPLC to afford 1-(7-chloro-6-fluoro-9-pyrazol-1-yl-1, 3, 4, 5-tetrahydropyrido[4, 3-b] indol-2-yl)-2-hydroxy-ethanone. ¹H NMR: (CD₃OD, 400 MHz) δ 8.02-7.95 (m, 1H), 7.83 (brd, J=15.7

Hz, 1H), 7.15 (dd, J=5.7, 13.3 Hz, 1H), 6.64-6.58 (m, 1H), 4.59 (s, 2H), 4.31 (brd, J=6.8 Hz, 2H), 4.07 (d, J=13.6 Hz, 2H), 3.95 (t, J=5.8 Hz, 1H), 3.74 (t, J=5.3 Hz, 1H), 3.50 (brs, 2H), 3.06-2.88 (m, 2H).

Some compounds of the invention, wherein a Suzuki-Miyaura or Ullman-type coupling is not required to introduce R⁴, can be prepared as described below in Synthetic Route B.

Synthetic Route B

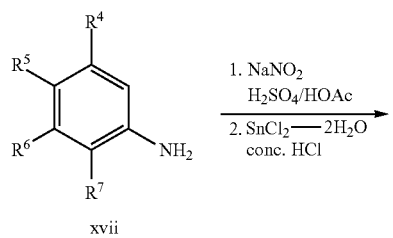

xvii

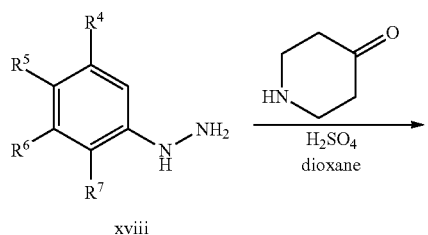

xviii

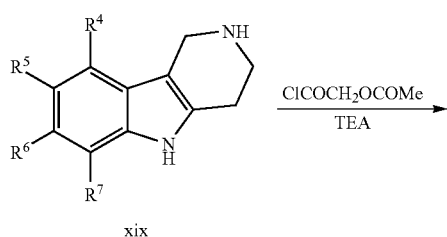

xix

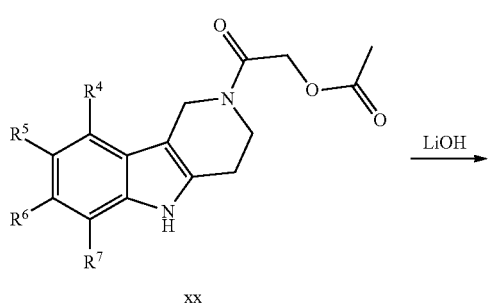

xx

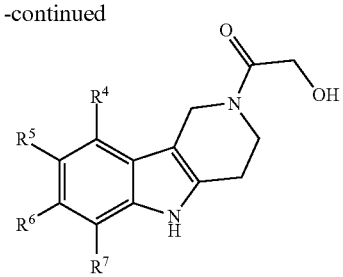

xxi

An example synthesis is provided for illustration:

1-(7-Bromo-6-fluoro-1, 3, 4, 5-tetrahydro-2H-pyrido[4, 3-b]indol-2-yl)-2-hydroxyethan-1-one

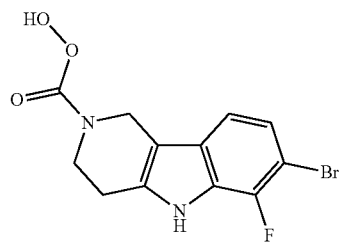

To a solution of 3-bromo-2-fluoroaniline (20.0 g, 105 mmol) in HCl (12.0 M, 100 mL, 11.4 eq) was added a solution of NaNO₂ (10.9 g, 158 mmol, 1.50 eq) in water (20.0 mL) drop-wise at 0° C. The mixture was stirred at 0° C. for 1 h. SnCl₂.2H₂O (71.3 g, 316 mmol, 3.00 eq) in H₂O (40.0 mL) was added to the mixture at 0° C. The mixture was stirred for 12 h at 20° C. The reaction mixture was filtered. The filter cake was washed with EtOAc (20.0 mL) and triturated with EtOAc (30.0 mL). The filter cake was dried to afford (3-bromo-2-fluorophenyl)hydrazine hydrochloride. LC-MS: m/z 205.1 [M+H]⁺

To a solution of (3-bromo-2-fluorophenyl)hydrazine hydrochloride (25.0 g, 104 mmol, HCl salt) and piperidin-4-one (16.8 g, 124 mmol, HCl salt) in dioxane (125 mL) was added H₂SO₄ (27.3 g, 278 mmol, 14.8 mL) at 0° C. The mixture was heated to 80° C. for 14 hrs. The mixture was poured into water (100 mL), and the pH was adjusted to 10 with the addition of aqueous NaOH solution (4M). The aqueous layer was extracted with ethyl acetate (3×100 mL). The combined organic layers were washed with brine (2×100 mL), dried over anhydrous sodium sulfate, filtered and concentrated. The residue was triturated with EtOAc (40.0 mL) and filtered to afford 7-bromo-6-fluoro-2, 3, 4, 5-tetrahydro-1H-pyrido[4, 3-b]indole. LC-MS: m/z 269.1 [M+H]⁺

To a solution of 7-bromo-6-fluoro-2, 3, 4, 5-tetrahydro-1H-pyrido[4, 3-b]indole (14.2 g, 52.8 mmol) and Et₃N (16.0 g, 158 mmol, 22.0 mL) in THF (70.0 mL) was added (2-chloro-2-oxo-ethyl) acetate (8.65 g, 63.3 mmol, 6.81 mL) at 0° C. The mixture was stirred at 25° C. for 3 h. The mixture was poured into water (300 mL). The mixture was extracted with EtOAc (3×100 mL). The combined organic layers were washed with brine (100 mL), dried over anhydrous sodium sulfate, and concentrated. The residue was triturated with EtOAc (60.0 mL) at 25° C. for 1 h. The mixture was filtered. The filter cake was dried to afford 2-(7-bromo-6-fluoro-1, 3, 4, 5-tetrahydro-2H-pyrido[4, 3-b]indol-2-yl)-2-oxoethyl acetate. ¹H NMR: (DMSO-d₆, 400 MHz) δ 11.69 (d, J=10.8 Hz, 1H), 7.25-7.15 (m, 2H), 4.91 (d, J=12.4 Hz, 2H), 4.62 (s, 2H), 3.85-3.71 (m, 2H), 2.89-2.77 (m, 2H), 2.09 (s, 3H).

To a solution of 2-(7-bromo-6-fluoro-1,3,4,5-tetrahydro-2H-pyrido[4,3-b]indol-2-yl)-2-oxoethyl acetate (12.0 g, 32.5 mmol) in MeOH (150 mL) and water (15.0 mL) was added LiOH H₂O (3.86 g, 92.0 mmol). The mixture was stirred at 25° C. for 2 h. The reaction mixture was concentrated. The solid was dissolved with water (100 mL) and the pH adjusted to 6 with addition of 1 M aqueous HCl solution. The mixture was filtered, and the filter cake was dried to afford a residue. The residue was triturated with EtOAc/acetonitrile (3/1, 40 mL) at 25° C. for 1 h. The mixture was filtered, the filter cake was dried to afford 1-(7-bromo-6-fluoro-1, 3, 4, 5-tetrahydro-2H-pyrido[4, 3-b]indol-2-yl)-2-hydroxyethan-1-one. ¹H NMR: (DMSO-d₆, 400 MHz) δ 11.66 & 11.64 (s, 1H), 7.26-7.14 (m, 2H), 4.65-4.55 (m, 3H), 4.23-4.19 (m, 2H), 3.87 (t, J=5.2 Hz, 1H), 3.69 (t, J=5.2 Hz, 1H), 2.86-2.77 (m, 2H). LC-MS: m/z 327.0 [M+H]⁺

Compounds in which R¹≠H may be made by alkylation of a suitably protected intermediate (Synthetic Route C):

Synthetic Route C

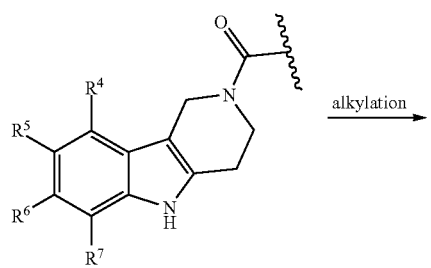

e.g., viii, xvi, ix, or xx

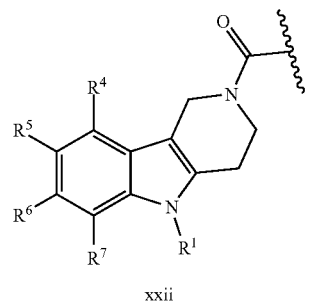

xxii

For some compounds where R¹≠H, the alkylating agent is R¹—X, wherein X is a suitable leaving group. Two examples are shown below:

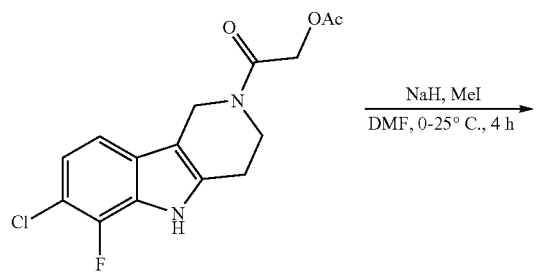

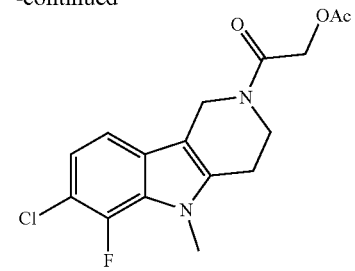

To a solution of 2-(7-chloro-6-fluoro-1, 3, 4, 5-tetrahydro-2H-pyrido[4, 3-b]indol-2-yl)-2-oxoethyl acetate (18.8 g, 57.9 mmol) in DMF (90.0 mL) was added NaH (2.35 g, 58.8 mmol, 60% in mineral oil) at 0° C. The mixture was stirred at 0° C. for 1 h. Methyl iodide (14.5 g, 102 mmol, 6.37 mL) was added at 0° C. The mixture was stirred at 25° C. for 2 h, and then more methyl iodide (8.22 g, 57.89 mmol, 3.60 mL) was added. The mixture was stirred at 25° C. for 1 h. The mixture was quenched with sat. aq. NH₄Cl (1.00 L), and the resulting solution was extracted with EtOAc (3×400 mL). The combined organic layers were concentrated. The residue was triturated with EtOAc (60.0 mL) at 25° C. for 1 h. The mixture was filtered, and the filter cake was dried to afford 2-(7-chloro-6-fluoro-5-methyl-1, 3, 4, 5-tetrahydro-2H-pyrido[4, 3-b]indol-2-yl)-2-oxoethyl acetate. ¹H NMR: (DMSO-d₆, 400 MHz) δ 7.31-7.27 (m, 1H), 7.10-7.05 (m, 1H), 4.92-4.89 (m, 2H), 4.61 (s, 2H), 3.86-3.74 (m, 5H), 2.90-2.79 (m, 2H), 2.09 (s, 3H).

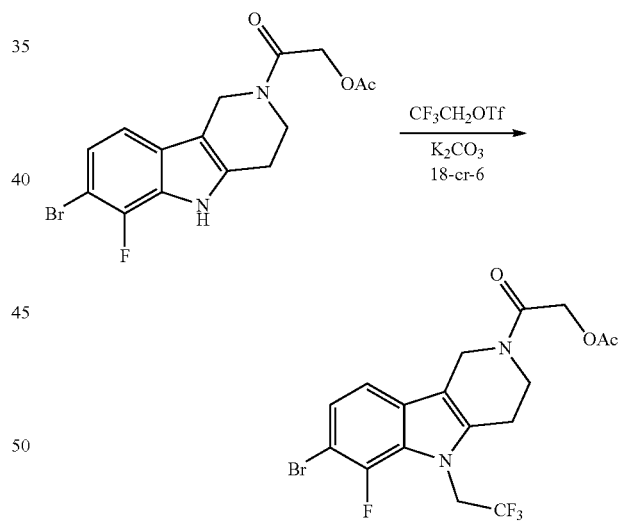

A mixture of [2-(7-bromo-6-fluoro-1, 3, 4, 5-tetrahydro-pyrido[4, 3-b]indol-2-yl)-2-oxo-ethyl]acetate (400 mg, 1.08 mmol), 2, 2, 2-trifluoroethyl trifluoromethanesulfonate (377 mg, 1.63 mmol, 80 μL), K₂CO₃ (299 mg, 2.17 mmol) and 1, 4, 7, 10, 13, 16-hexaoxacyclooctadecane (573 mg, 2.17 mmol) in anhydrous DMF (5 mL) was stirred under heating at 65° C. for 3 h. The reaction was cooled to 20° C., and additional reactants were added to the mixture [2, 2, 2-trifluoroethyl trifluoromethanesulfonate (377 mg, 1.63 mmol, 80 uL), K₂CO₃ (299 mg, 2.17 mmol), and 1, 4, 7, 10, 13, 16-hexaoxacyclooctadecane (286 mg, 1.08 mmol)]. The reaction was stirred at 65° C. for 3 h. The reaction mixture was concentrated. The residue was purified by preparative- HPLC (TFA condition) to afford [2-[7-bromo-6-fluoro-5-(2, 2, 2-trifluoroethyl)-3, 4-dihydro-1H-pyrido[4, 3-b]indol-2-yl]-2-oxo-ethyl] acetate. $^1$H NMR: (DMSO-$d_6$, 400 MHz) δ 7.35-7.26 (m, 2H), 5.18-5.11 (m, 2H), 4.92 (brd, J=12.6 Hz, 2H), 4.63 (s, 2H), 3.90-3.72 (m, 2H), 2.96-2.76 (m, 2H), 2.09 (s, 3H).

For compounds where $R^1$=CHF$_2$, the alkylating agent is BrF$_2$CCOOEt instead of $R^1$I and the mixture is heated at 60 C for ~2.5 h. An example is shown below:

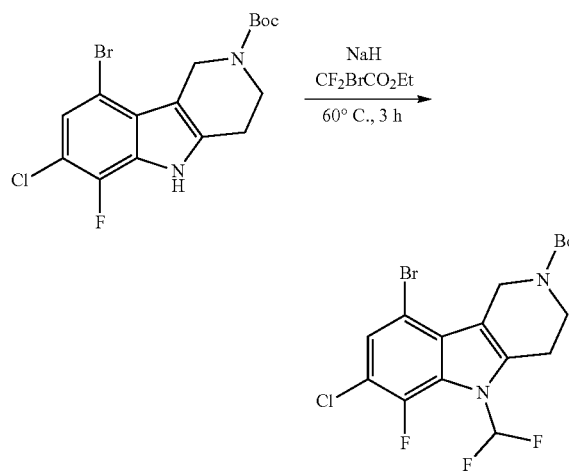

Sodium hydride (139 mg, 3.48 mmol, 60% in mineral oil) was added in portions into a stirred solution of tert-butyl 9-bromo-7-chloro-6-fluoro-1, 3, 4, 5-tetrahydropyrido[4, 3-b] indole-2-carboxylate (0.7 g, 1.73 mmol) in DMF (15 mL) at 15° C. After stirring at 15° C. for 0.5 h, ethyl 2-bromo-2, 2-difluoroacetate (422 mg, 2.08 mmol, 267 µL) was added to the mixture drop wise. The reaction mixture was stirred at 60° C. for 2.5 h. The reaction mixture was quenched by addition of a saturated aqueous NH$_4$Cl solution (50 mL). The mixture was extracted with EtOAc (3×20 mL). The combined organic layers were washed with brine (30 mL), dried over anhydrous sodium sulfate and filtered. The filtrate was concentrated under reduced pressure. The residue was purified by column chromatography (SiO$_2$, petroleum ether/ethyl acetate=15/1 to 10/1) to give tert-butyl 9-bromo-7-chloro-5-(difluoromethyl)-6-fluoro-3, 4-dihydro-1H-pyrido[4, 3-b]indole-2-carboxylate. $^1$H NMR: (DMSO-$d_6$, 400 MHz) δ 7.80-7.45 (m, 1H), 7.37-7.33 (m, 1H), 4.95 (brs, 2H), 3.74 (brs, 2H), 2.99 (brs, 2H), 1.52 (s, 9H).

For the above example, the Boc group is removed under standard conditions (HCl/EtOAc) and the α-hydroxy amide is formed as described above.

In general, compounds of the invention in which $R^2 \neq H$ were formed using a requisite ether acid chloride, i.e., ClC(=O)CHR$^{30}$OR$^2$, in place of the aforementioned acetate acid chloride (i.e., C$_1$C(=O)CH$_2$OC(=O)CH$_3$).

Some compounds xxxiii, xxxiv, and xxxv of the invention, wherein $R^{20}$ is (C$_1$-C$_3$)alkyl and $R^{21}$ is hydrogen, can be prepared as described below in Synthetic Route D. The bracket step is optional for when $R^4$ is aryl or heteroaryl and a Suzuki-Miyaura introduces the $R^4$ group. Compounds xxxiv and xxxv are substantially pure antipodes of each other (>80% e.e.), but their absolute configuration is undetermined.

Synthetic Route D

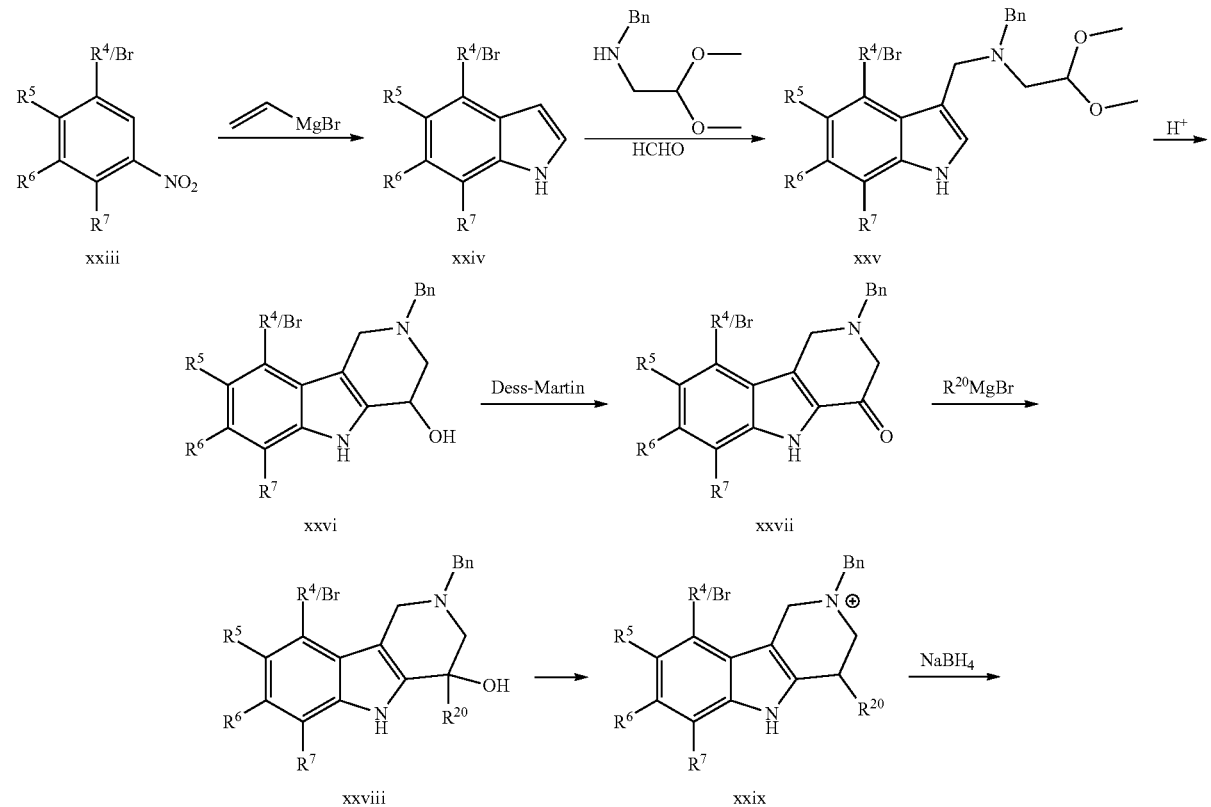

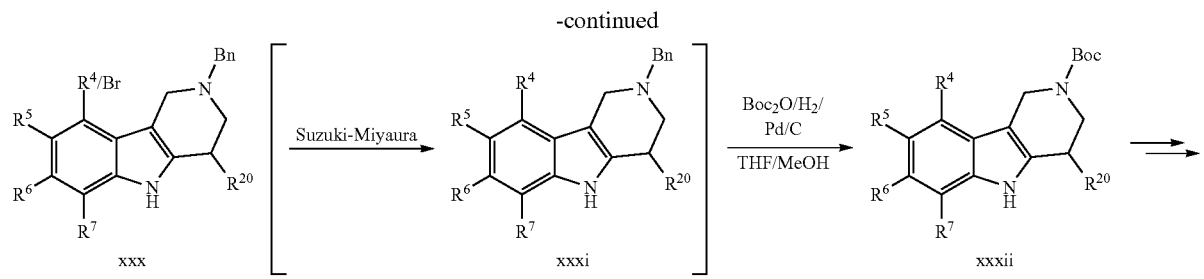

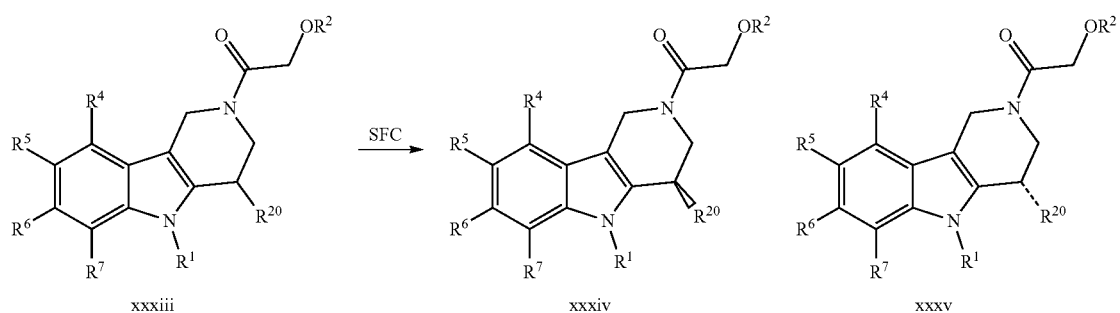

Reaction of optionally substituted-nitrobenzene derivatives xxiii provides indole products xxiv, which react with a tertiary imine formed in situ to provide intermediates xxv. Cyclocondensation of the acetals xxv provide alcohols xxvi, which are oxidized to ketones xxvii. The $(C_1-C_3)$alkyl $R^{20}$ group is introduced via a Grignard reagent to provide alcohols xxviii, which undergo dehydration/aromatization to form pyridinium ions xxix. Reduction of pyridinium ions xxix with sodium borohydride provide intermediates xxx. Aryl and heteroaryl $R^4$ groups may be introduced to intermediates xxx when said intermediates are aryl bromide intermediates. Subsequent protecting group exchange results in intermediate Boc-derivatives xxxii, which are converted via methods described supra to racemic substituted compounds xxxiii. Resolution can then be accomplished via chiral supercritical fluid chromatography to provide substantially pure enantiomers xxxiv and xxxv.

An example synthetic scheme is provided for illustration:

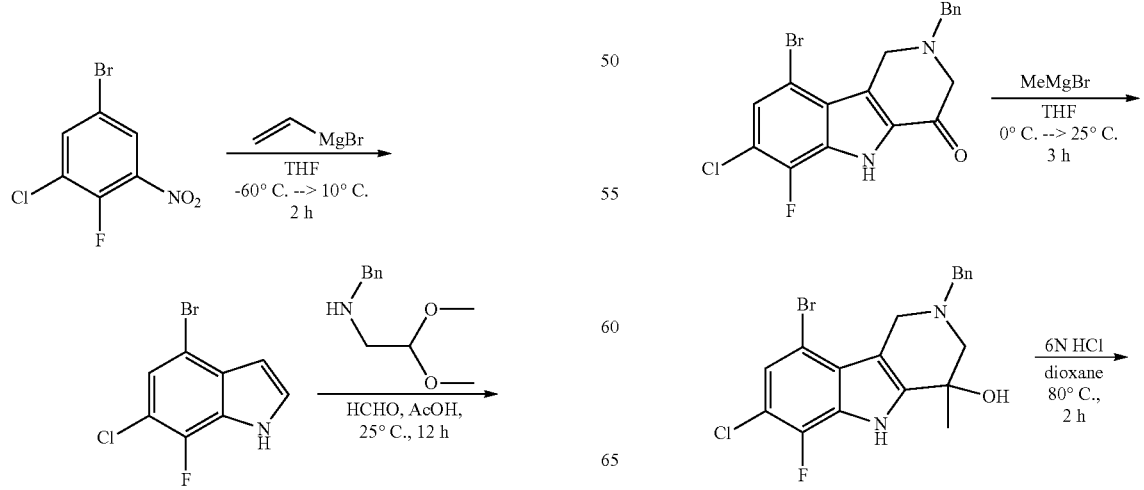

-continued

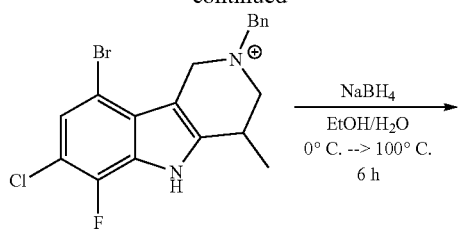

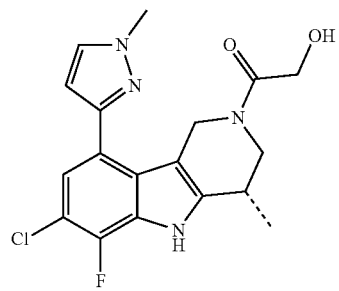 [SMILES: C[C@H]1CN(C(=O)CO)Cc2c1[nH]c1c(F)c(Cl)cc(-c3ccn(C)n3)c21]

Synthetic details and the resolution is described below:

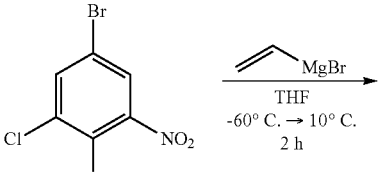

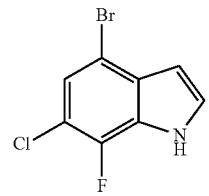

To a mixture of 5-bromo-1-chloro-2-fluoro-3-nitro-benzene (25.0 g, 98.3 mmol) in THF (250 mL) was added vinyl-magnesium bromide (1 M, 500 mL) at −60° C. under nitrogen dropwise. The mixture was allowed to warm to 10° C. and was stirred for 2 h. The reaction mixture was poured into sat. aq. NH$_4$Cl solution (1.0 L), and the pH was adjusted to 7 with the addition of an aqueous HCl solution (6 M). The solution was extracted with EtOAc (3×500 mL). The combined organic layers were washed with brine (1.0 L), dried over anhydrous sodium sulfate, and filtered. The filtrate was concentrated under reduced pressure. The residue was purified by column chromatography (SiO$_2$, Petroleum ether:Ethyl acetate=1:0 to 50:1). The material was further purified by column chromatography (SiO$_2$, Petroleum ether:Ethyl acetate=0:1 to 49:1) to give 4-bromo-6-chloro-7-fluoro-1H-indole. $^1$H NMR: (CDCl$_3$, 400 MHz) δ8.52 (brs, 1H), 7.29-7.28 (m, 2H), 6.61-6.59 (m, 1H).

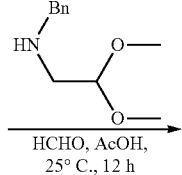

-continued

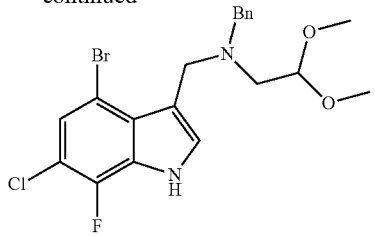

To a mixture of 4-bromo-6-chloro-7-fluoro-1H-indole (14.0 g, 56.3 mmol) in AcOH (140 mL) was added HCHO (5.03 g, 62.0 mmol, 4.61 mL, 37% solution in water) and N-benzyl-2, 2-dimethoxy-ethanamine (13.2 g, 67.6 mmol). The mixture was stirred at 25° C. for 12 h. The reaction mixture was diluted with water (300 mL), and the pH of the mixture was adjusted to 8 with a NaOH solution (1 M, aqueous). The solution was extracted with EtOAc (3×150 mL). The organic layer was washed with brine (200 mL), dried over anhydrous sodium sulfate, and filtered. The filtrate was concentrated under reduced pressure. The residue was purified by column chromatography (SiO$_2$, Petroleum ether:Ethyl acetate=97:3 to 9:1) to give N-benzyl-N-[(4-bromo-6-chloro-7-fluoro-1H-indol-3-yl)methyl]-2, 2-dimethoxy-ethanamine. $^1$H NMR: (CDCl$_3$, 400 MHz) δ7.33-7.31 (m, 2H), 7.26-7.17 (m, 5H), 4.49-4.41 (m, 1H), 4.08-4.07 (m, 2H), 3.75-3.72 (m, 2H), 3.22-3.20 (m, 6H), 2.72-2.69 (m, 2H).

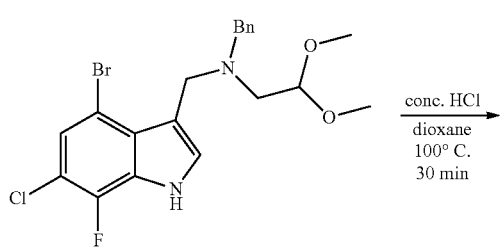

A mixture of N-benzyl-N-[(4-bromo-6-chloro-7-fluoro-1H-indol-3-yl)methyl]-2, 2-dimethoxy-ethanamine (8.0 g, 17.6 mmol) in dioxane (80 mL) and aqueous HCl (6 M, 80 mL) was stirred at 100° C. for 0.5 h. The reaction mixture was diluted with water (300 mL), and the pH was adjusted to 8 with sat. aq NaHCO$_3$ solution. The mixture was extracted with 2-methyltetrahydrofuran (3×150 mL). The combined organic layers were washed with brine (200 mL), dried over anhydrous sodium sulfate, and filtered. The filtrate was concentrated under reduced pressure. The residue was purified by column chromatography (SiO$_2$, Petroleum ether:Ethyl acetate=10:1 to 3:1). The material was further purified by column chromatography (SiO$_2$, Petroleum ether:Ethyl acetate=9:1 to 3:1) to give 2-benzyl-9-bromo-7-chloro-6-fluoro-1, 3, 4, 5-tetrahydropyrido[4, 3-b]indol-4-ol. $^1$H NMR: (DMSO-d$_6$, 400 MHz) δ 12.14 (s, 1H), 7.41-7.26 (m, 6H), 5.36 (d, J=7.46 Hz, 1H), 4.74-4.70 (m, 1H), 3.93-3.82 (m, 2H), 3.77 (s, 2H), 2.94-2.90 (m, 1H), 2.58-2.53 (m, 1H).

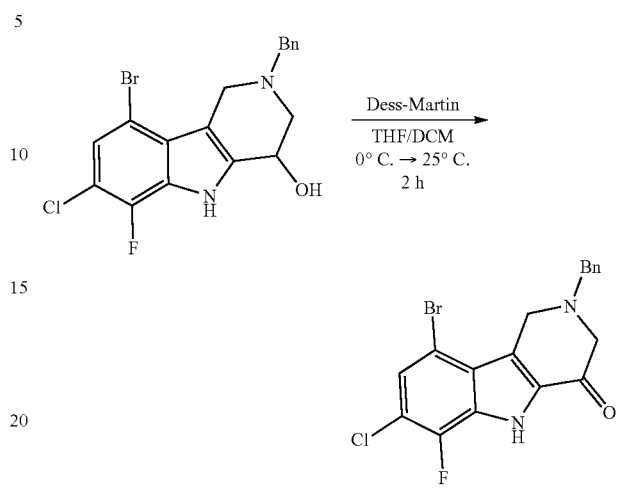

To a mixture of 2-benzyl-9-bromo-7-chloro-6-fluoro-1, 3, 4, 5-tetrahydropyrido[4, 3-b]indol-4-ol (480 mg, 1.17 mmol) in THF (15 mL) and DCM (5 mL) was added Dess-Martin periodinane (994 mg, 2.34 mmol, 725 µL) at 0° C. The mixture was stirred at 25° C. for 2 h. The reaction mixture was diluted with sat. aq. NaHCO$_3$ solution (300 mL), and the mixture was extracted with 2-methyltetrahydrofuran (3×150 mL). The combined organic layers were washed with brine (200 mL), dried over anhydrous sodium sulfate, and filtered. The filtrate was concentrated under reduced pressure. The residue was purified by column chromatography (SiO$_2$, Petroleum ether: 2-methyltetrahydrofuran=10:1 to 5:1) to give 2-benzyl-9-bromo-7-chloro-6-fluoro-3, 5-dihydro-1H-pyrido[4, 3-b]indol-4-one. $^1$H NMR: (DMSO-d$_6$, 400 MHz) δ 13.00 (brs, 1H), 7.48 (d, J=5.75 Hz, 1H), 7.39-7.34 (m, 4H), 7.33-7.27 (m, 1H), 4.24 (s, 2H), 3.84 (s, 2H), 3.38 (s, 2H).

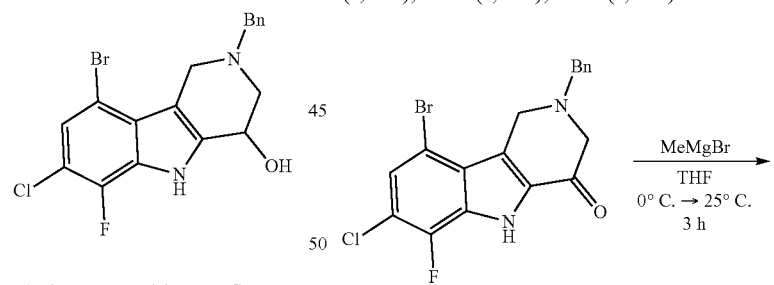

To a mixture of 2-benzyl-9-bromo-7-chloro-6-fluoro-3, 5-dihydro-1H-pyrido[4, 3-b]indol-4-one (1.0 g, 2.45 mmol) in THF (10 mL) was added bromo(methyl)magnesium (3 M in diethyl ether, 4.91 mL) at 0° C. The mixture was allowed to stir at 25° C. for 3 h. The reaction mixture was diluted with sat. aq NH$_4$Cl solution (50 mL). The solution was extracted with EtOAc (3×30 mL). The combined organic layers were washed with brine (40 mL), dried over anhydrous sodium sulfate, and filtered. The filtrate was concentrated under reduced pressure. The residue was purified by column chromatography (SiO$_2$, Petroleum ether:Ethyl acetate=19:1 to 4:1) to give 2-benzyl-9-bromo-7-chloro-6-fluoro-4-methyl-3, 5-dihydro-1H-pyrido[4, 3-b]indol-4-ol. $^1$H NMR: (DMSO-d$_6$, 400 MHz) δ 12.06 (s, 1H), 7.42-7.40 (m, 2H), 7.36-7.34 (m, 2H), 7.28-7.24 (m, 2H), 3.93-3.89 (m, 1H), 3.83-3.72 (m, 3H), 2.62-2.60 (m, 2H), 1.47 (s, 3H).

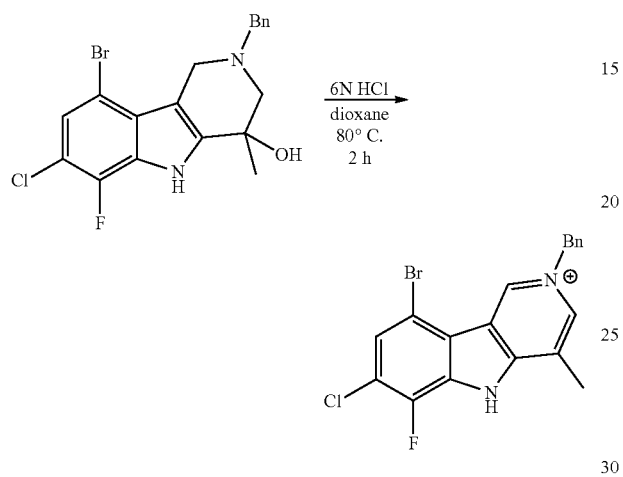

To a mixture of 2-benzyl-9-bromo-7-chloro-6-fluoro-4-methyl-3, 5-dihydro-1H-pyrido[4, 3-b]indol-4-ol (700 mg, 1.65 mmol) in dioxane (21 mL) was added conc. HCl (12 M, 21 mL). The mixture was stirred at 80° C. for 2 h. The reaction mixture was concentrated under reduced pressure to give 2-benzyl-9-bromo-7-chloro-6-fluoro-4-methyl-5H-pyrido[4, 3-b]indol-2-ium, which was used directly in next step.

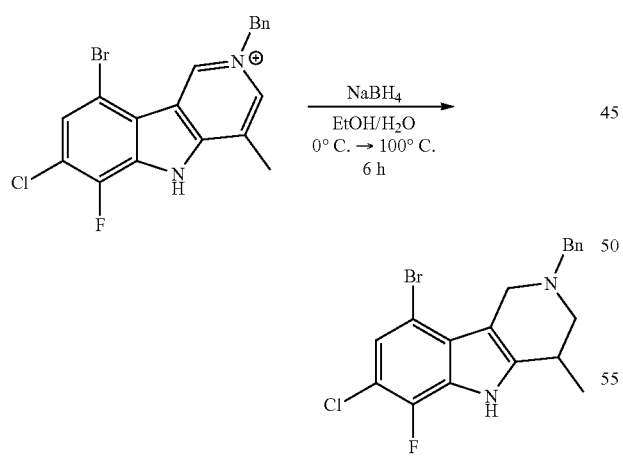

To a mixture of 2-benzyl-9-bromo-7-chloro-6-fluoro-4-methyl-5H-pyrido[4, 3-b]indol-2-ium (1.2 g, 2.73 mmol) in EtOH (15 mL) and water (15 mL) was added NaBH$_4$ (1.03 g, 27 mmol) at 0° C. The mixture was stirred at 100° C. for 6 h. The reaction mixture was poured into water (100 mL). The mixture was extracted with EtOAc (3×50 mL). The combined organic layers were washed with brine (100 mL), dried over anhydrous sodium sulfate, and filtered. The filtrate was concentrated under reduced pressure. The residue was purified by column chromatography (SiO$_2$, petroleum ether: ethyl acetate=1:0 to 17:3) to give 2-benzyl-9-bromo-7-chloro-6-fluoro-4-methyl-1, 3, 4, 5-tetrahydropyrido[4, 3-b]indole. LC-MS: m/z 409.1 [M+H]$^+$

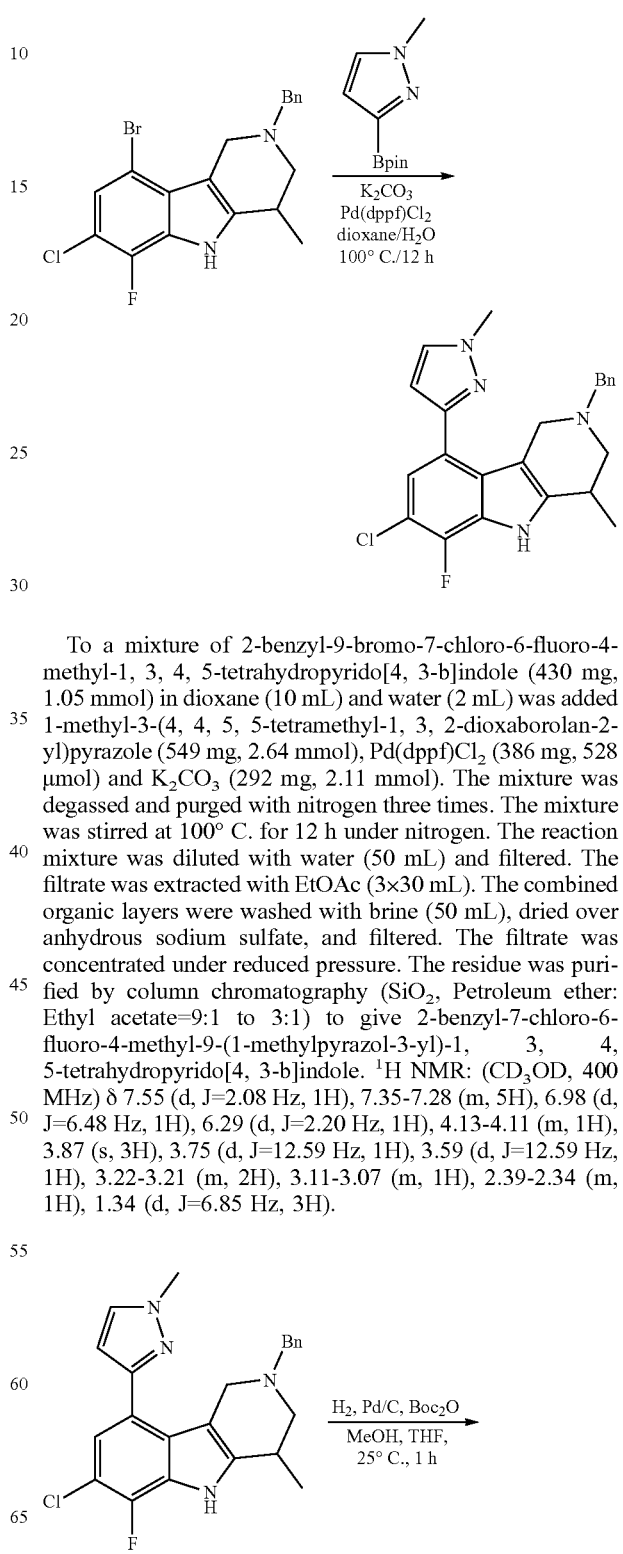

To a mixture of 2-benzyl-9-bromo-7-chloro-6-fluoro-4-methyl-1, 3, 4, 5-tetrahydropyrido[4, 3-b]indole (430 mg, 1.05 mmol) in dioxane (10 mL) and water (2 mL) was added 1-methyl-3-(4, 4, 5, 5-tetramethyl-1, 3, 2-dioxaborolan-2-yl)pyrazole (549 mg, 2.64 mmol), Pd(dppf)Cl$_2$ (386 mg, 528 μmol) and K$_2$CO$_3$ (292 mg, 2.11 mmol). The mixture was degassed and purged with nitrogen three times. The mixture was stirred at 100° C. for 12 h under nitrogen. The reaction mixture was diluted with water (50 mL) and filtered. The filtrate was extracted with EtOAc (3×30 mL). The combined organic layers were washed with brine (50 mL), dried over anhydrous sodium sulfate, and filtered. The filtrate was concentrated under reduced pressure. The residue was purified by column chromatography (SiO$_2$, Petroleum ether: Ethyl acetate=9:1 to 3:1) to give 2-benzyl-7-chloro-6-fluoro-4-methyl-9-(1-methylpyrazol-3-yl)-1, 3, 4, 5-tetrahydropyrido[4, 3-b]indole. $^1$H NMR: (CD$_3$OD, 400 MHz) δ 7.55 (d, J=2.08 Hz, 1H), 7.35-7.28 (m, 5H), 6.98 (d, J=6.48 Hz, 1H), 6.29 (d, J=2.20 Hz, 1H), 4.13-4.11 (m, 1H), 3.87 (s, 3H), 3.75 (d, J=12.59 Hz, 1H), 3.59 (d, J=12.59 Hz, 1H), 3.22-3.21 (m, 2H), 3.11-3.07 (m, 1H), 2.39-2.34 (m, 1H), 1.34 (d, J=6.85 Hz, 3H).

-continued

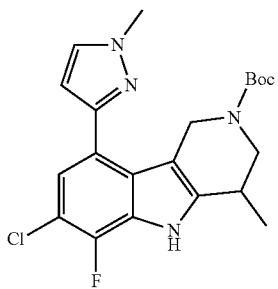

To a mixture of 2-benzyl-7-chloro-6-fluoro-4-methyl-9-(1-methylpyrazol-3-yl)-1, 3, 4, 5-tetrahydropyrido[4, 3-b]indole (300 mg, 734 µmol) and Boc$_2$O (178 mg, 816 µmol, 187.09 µL) in MeOH (3 mL) and THF (0.9 mL) was added Pd/C (20 mg, 10 wt %). The mixture was degassed and purged with H$_2$ three times. The mixture was stirred under H$_2$ (15 psi) at 25° C. for 1 h. The reaction mixture was filtered, and the filtrate was concentrated under reduced pressure. The residue was purified by column chromatography (SiO$_2$, petroleum ether: ethyl acetate=19:1 to 4:1) to give tert-butyl 7-chloro-6-fluoro-4-methyl-9-(1-methylpyrazol-3-yl)-1, 3, 4, 5-tetrahydropyrido[4, 3-b]indole-2-carboxylate. $^1$H NMR: (DMSO-d$_6$, 400 MHz) δ 11.71 (s, 1H), 7.76 (s, 1H), 7.06 (d, J=6.48 Hz, 1H), 6.49 (s, 1H), 4.46-4.39 (m, 2H), 3.91 (d, J=3.2 Hz, 3H), 3.69-3.65 (m, 1H), 3.47-3.35 (m, 1H), 3.04-3.01 (m, 1H), 1.38 (s, 9H), 1.27-1.25 (m, 3H).

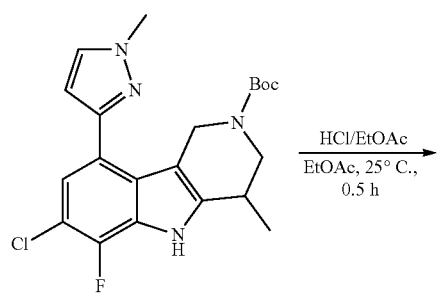

To a mixture of tert-butyl 7-chloro-6-fluoro-4-methyl-9-(1-methylpyrazol-3-yl)-1, 3, 4, 5-tetrahydropyrido[4, 3-b]indole-2-carboxylate (200 mg, 477 µmol) in EtOAc (2 mL) was added HCl/EtOAc (4 M, 10 mL). The mixture was stirred at 25° C. for 0.5 h. The reaction mixture was concentrated under reduced pressure to give 7-chloro-6-fluoro-4-methyl-9-(1-methylpyrazol-3-yl)-2, 3, 4, 5-tetrahydro-1H-pyrido[4, 3-b]indole-HCl. The HCl salt (190 mg) was dissolved in water (30 ml). The pH of the mixture was adjusted to 8 by the addition of a sat. aq NaHCO$_3$ solution. The mixture was extracted with EtOAc (3×20 mL). The combined organic layer were washed with brine (30 mL), dried over anhydrous sodium sulfate, and filtered. The filtrate was concentrated under reduced pressure to give the free base.

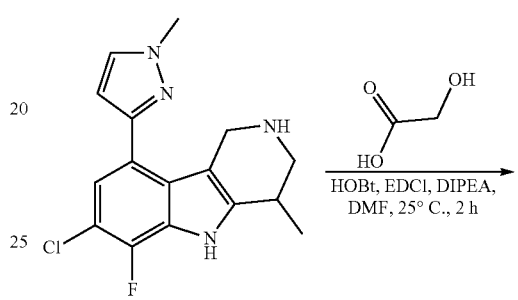

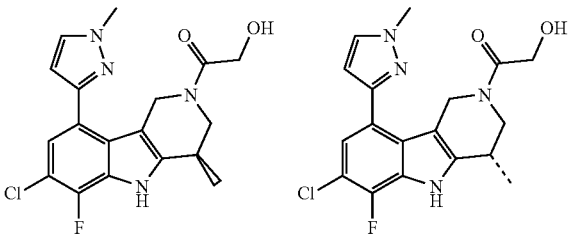

To a mixture of 7-chloro-6-fluoro-4-methyl-9-(1-methylpyrazol-3-yl)-2, 3, 4, 5-tetrahydro-1H-pyrido[4, 3-b]indole (110 mg, 345 mmol) in DMF (2 mL) was added HOBt (50 mg, 370 mmol), EDCI (71 mg, 370 mmol), DIPEA (120 mg, 928 mmol, 160 mL) and 2-hydroxyacetic acid (28 mg, 368 mmol, 23 mL). The mixture was stirred at 25° C. for 2 h. The reaction mixture was diluted with water (30 mL). The solution was extracted with EtOAc (3×20 mL). The organic layer was washed with brine (30 mL), dried over anhydrous sodium sulfate, and filtered. The filtrate was concentrated under reduced pressure. The residue was purified by preparative thin-layer chromatography (Petroleum ether:Ethyl acetate:Ethyl alcohol=4:3:1). The pure enantiomers were obtained via chromatographic resolution via SFC (column: DAICEL CHIRALPAK AD-H (250 mm×30 mm, 5 µm); mobile phase: [0.1% NH$_4$OH in MeOH]; B %: 50%, 3.8 min) in greater than 97% ee. $^1$H NMR (400 MHz, CD$_3$OD) δ 7.67-7.65 (m, 1H), 7.07-7.03 (m, 1H), 6.45-6.42 (m, 1H), 4.58-4.34 (m, 2H), 4.30 (s, 1H), 4.21-4.19 (m, 1H), 4.00-3.99 (d, 3H), 3.94-3.91 (m, 0.5H), 3.78-3.75 (m, 0.5H), 3.68-3.66 (m, 0.5H), 3.36-3.33 (m, 0.5H), 3.22-3.09 (m, 1H), 1.34 (q, 3H). LC-MS: m/z 377.0 [M+H]$^+$ Some representative compounds of the invention in which neither R[20] nor R[21] are hydrogen (e.g., both R[20] and R[21] are methyl) may be synthesized as shown in Synthetic Route E:

Synthetic Route E

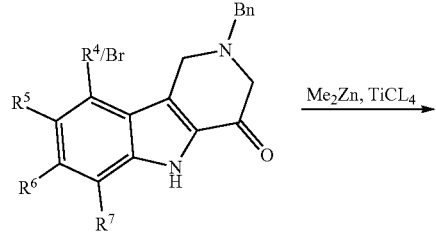

xxvii

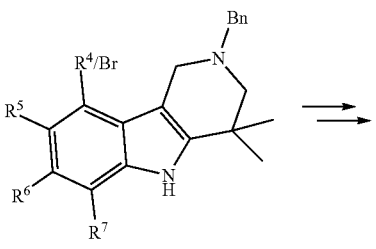

xxxvi

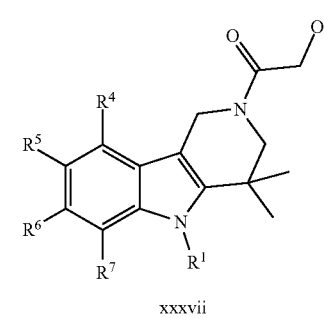

xxxvii

Synthetic Route F

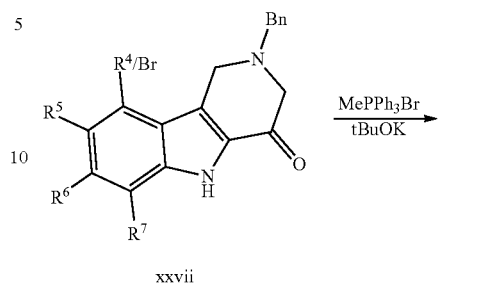

xxvii

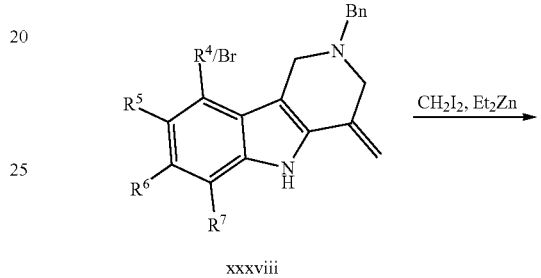

xxxviii

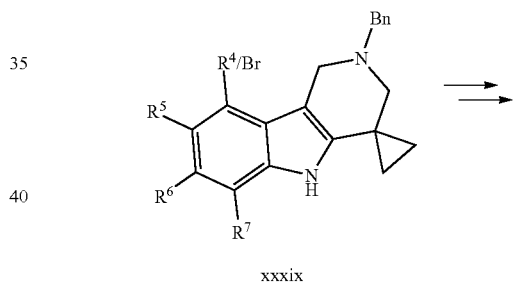

xxxix

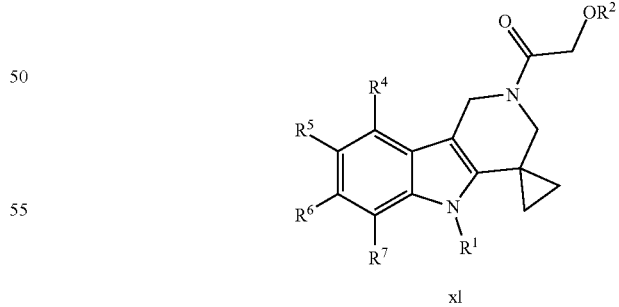

xl

Reaction of optionally substituted ketones xxvii with dimethylzinc and titanium tetrachloride according to a known procedure (*Bioorganic & Medicinal Chemistry Letters* 25 (2015) 3368-3372) may provide dimethyl derivative xxxvi. Dimethyl derivative xxxvi may be converted via methods described supra to compounds xxxvii wherein R[20] and R[21] are methyl. It should be noted that Et$_2$Zn, Pr$_2$Zn, and iPr$_2$Zn are also known. Thus, compounds such xxxvii where R[20] and R[21] are (C$_1$-C$_3$)alkyl may be accessed.

Some representative compounds of the invention in which R[20] and R[21], together with the carbon to which they are attached, form a cyclopropyl ring may be synthesized as shown in Synthetic Route F:

Wittig reaction of optionally substituted ketones xxvii may provide alkene xxxviii. Alkene xxxviii may be reacted with diiodomethane and diethylzinc to provide spirocyclopropyl intermediate xxxix, which may be converted via methods described supra to compounds xl wherein R[20] and R[21] form a cyclopropyl ring.

Spectroscopic data for representative compounds of the invention are shown in Table 1:

TABLE 1

Spectroscopic Data for Representative Compounds.

| Structure | ID # | Spectroscopic Data |
|---|---|---|
| 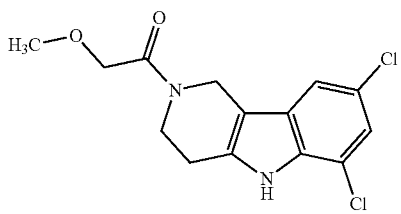 [SMILES: COCC(=O)N1CCc2[nH]c3c(Cl)cc(Cl)cc3c2C1] | TDI-004576 | 1H NMR (500 MHz, DMSO-d6) δ 11.52 (d, J = 9.9 Hz, 1H), 7.53 (dd, J = 21.2, 1.8 Hz, 1H), 7.31-6.88 (m, 1H), 4.60 (d, J = 19.7 Hz, 2H), 4.20 (d, J = 17.4 Hz, 2H), 3.90-3.67 (m, 2H), 3.3 (s, 3H), 2.92-2.76 m, 2H). LC-MS: m/z 313.2 [M + H]+ |
| 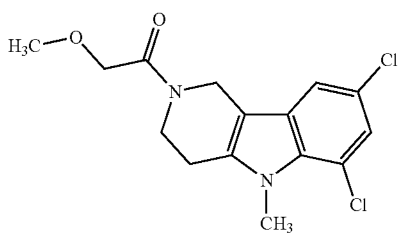 [SMILES: COCC(=O)N1CCc2c(c3cc(Cl)cc(Cl)c3n2C)C1] | TDI-004581 | 1H NMR (500 MHz, DMSO-d6) δ 7.68-7.35 (m, 1H), 7.27-7.05 (m, 1H), 4.59 (d, J = 18.7 Hz, 2H), 4.19 (d, J = 23.8 Hz, 2H), 3.92 (s, 3H), 3.88-3.68 (m, 2H), 3.29 (s, 3H), 2.95-2.72 (m, 2H). LC-MS: m/z 327.2 [M + H]+ |
| 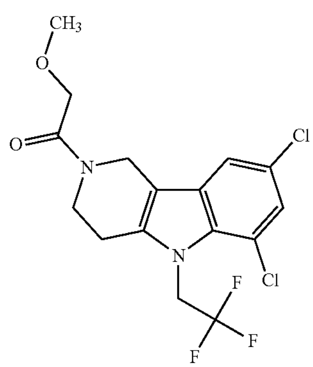 [SMILES: COCC(=O)N1CCc2c(c3cc(Cl)cc(Cl)c3n2CC(F)(F)F)C1] | TDI-005021 | 1H NMR (500 MHz, DMSO-d6) δ 7.65 (dd, J = 25.6, 2.0 Hz, 1H), 7.40-7.21 (m, 1H), 5.38 (q, J = 8.8 Hz, 2H), 4.61 (d, J = 14.5 Hz, 2H), 4.21 (d, J = 15.1 Hz, 2H), 3.86 (d, J = 5.8 Hz, 1H), 3.76 (t, J = 5.7 Hz, 1H), 3.32 (s, 3H), 2.91 (d, J = 5.8 Hz, 1H), 2.82 (d, J = 5.8 Hz, 1H). LC-MS: m/z 395.2 [M + H]+ |
| 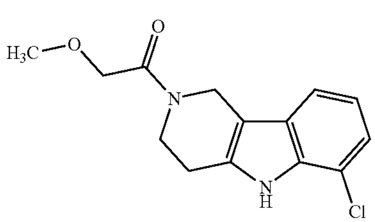 [SMILES: COCC(=O)N1CCc2[nH]c3c(Cl)cccc3c2C1] | TDI-005323 | 1H NMR (400 MHz, DMSO-d6) δ 11.03 (brs, 1H), 7.39 (d, J = 7.9 Hz, 1H), 7.11 (d, J = 7.5 Hz, 1H), 7.03-6.94 (m, 1H), 4.65 (s, 2H), 4.20 (s, 2H), 3.81 (brs, 2H), 3.34 (s, 3H), 2.88 (brs, 2H). LC-MS: m/z 279.1 [M + H]+ |
| 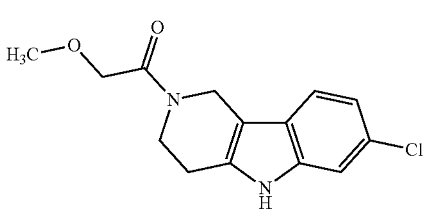 [SMILES: COCC(=O)N1CCc2[nH]c3cc(Cl)ccc3c2C1] | TDI-005324 | 1H NMR (400 MHz, DMSO-d6) δ 11.14-10.80 (m, 1H), 7.44-6.95 (m, 3H), 4.91 (s, 1H), 4.63 (s, 1H), 4.19 (s, 2H), 3.80 (brs, 2H), 3.34 (s, 3H), 2.84 (brs, 2H). LC-MS: m/z 278.9 [M + H]+ |
| 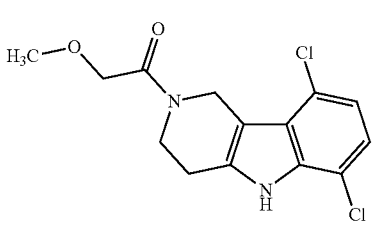 [SMILES: COCC(=O)N1CCc2[nH]c3c(Cl)ccc(Cl)c3c2C1] | TDI-005325 | 1H NMR (400 MHz, DMSO-d6) δ 11.42 (brs, 1H), 7.13-7.05 (m, 1H), 7.03-6.96 (m, 1H), 4.91 (s, 2H), 4.20 (s, 2H), 3.80 (brs, 2H), 3.34 (s, 3H), 2.88 (brs, 2H). LC-MS: m/z 312.9 [M + H]+ |

TABLE 1-continued

Spectroscopic Data for Representative Compounds.

| Structure | ID # | Spectroscopic Data |
|---|---|---|
| 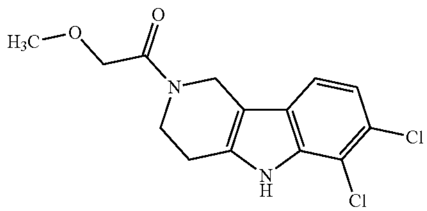 [SMILES: COCC(=O)N1CCc2[nH]c3c(Cl)c(Cl)ccc3c2C1] | TDI-005397 | 1H NMR (400 MHz, DMSO-d6) δ 11.42 (brs, 1H), 7.13-7.05 (m, 1H), 7.03-6.96 (m, 1H), 4.91 (s, 2H), 4.20 (s, 2H), 3.80 (brs, 2H), 3.34 (s, 3H), 2.88 (brs, 2H). LC-MS: m/z 313.0 [M + H]⁺ |
| 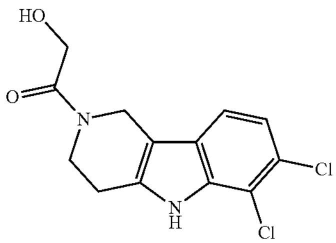 [SMILES: O=C(CO)N1CCc2[nH]c3c(Cl)c(Cl)ccc3c2C1] | TDI-005685 | 1H NMR (400 MHz, DMSO-d6) δ 11.51 (d, J = 12.3 Hz, 1H), 7.46 (dd, J = 25.9, 8.4 Hz, 1H), 7.19 (t, J = 8.6 Hz, 1H), 4.74-4.55 (m, 3H), 4.23 (dd, J = 19.5, 5.5 Hz, 2H), 3.80 (dt, J = 89.5, 5.7 Hz, 2H), 2.86 (dt, J = 40.1, 5.8 Hz, 2H). LC-MS: m/z 299.0 [M + H]⁺ |
| 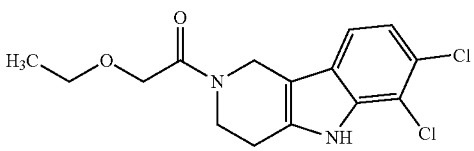 [SMILES: CCOCC(=O)N1CCc2[nH]c3c(Cl)c(Cl)ccc3c2C1] | TDI-005716 | LC-MS: m/z 327.1 [M + H]⁺ |
| 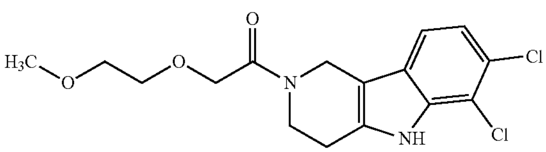 [SMILES: COCCOCC(=O)N1CCc2[nH]c3c(Cl)c(Cl)ccc3c2C1] | TDI-005719 | LC-MS: m/z 357.1 [M + H]⁺ |
| 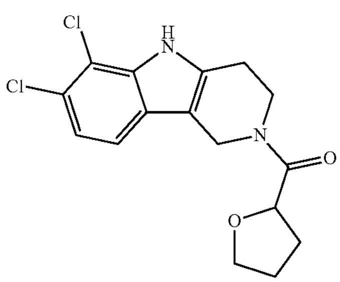 [SMILES: O=C(C1CCCO1)N1CCc2[nH]c3c(Cl)c(Cl)ccc3c2C1] | TDI-005745 | LC-MS: m/z 339.1 [M + H]⁺ |
| 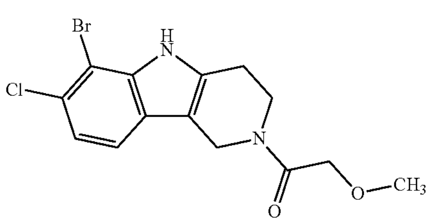 [SMILES: COCC(=O)N1CCc2[nH]c3c(Br)c(Cl)ccc3c2C1] | TDI-005776 | δ 7.36 (dd, J = 8.38, 3.31 Hz, 1H), 7.12 (d, J = 8.38 Hz, 1H), 4.75-4.63 (m, 2H), 4.28 (d, J = 4.19 Hz, 2H), 3.98 (t, J = 5.84 Hz, 1H), 3.84 (t, J = 5.73 Hz, 1H), 3.42 (d, J = 5.51 Hz, 3H), 2.99-2.85 (m, 2H). LC-MS: m/z 358.9 [M + H]⁺ |
| 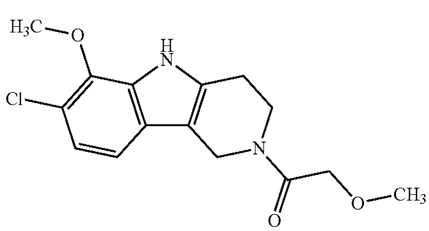 [SMILES: COCC(=O)N1CCc2[nH]c3c(OC)c(Cl)ccc3c2C1] | TDI-005777 | δ 7.19-7.07 (m, 1H), 7.03-6.91 (m, 1H), 4.75-4.59 (m, 2H), 4.28 (d, J = 4.63 Hz, 2H), 3.98 (brt, J = 5.84 Hz, 1H), 3.95 (s, 3H), 3.89-3.73 (m, 1H), 3.43 (d, J = 4.85 Hz, 3H), 2.97-2.83 (m, 2H). LC-MS: m/z 309.0 [M + H]⁺ |

TABLE 1-continued

Spectroscopic Data for Representative Compounds.

| Structure | ID # | Spectroscopic Data |
|---|---|---|
| 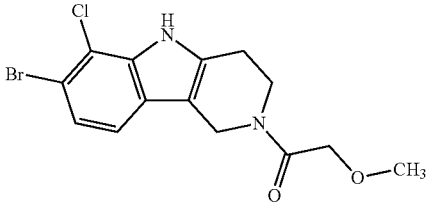 | TDI-005854 | δ 7.33-7.21 (m, 2H), 4.77-4.64 (m, 2H), 4.28 (d, J = 4.16 Hz, 2H), 3.99 (t, J = 5.81 Hz, 1H), 3.85 (t, J = 5.69 Hz, 1H), 3.42 (d, J = 5.62 Hz, 3H), 2.98-2.84 (m, 2H). LC-MS: m/z 359.0 [M + H]$^+$ |
| 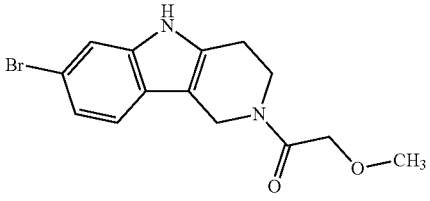 [SMILES: COCC(=O)N1CCc2[nH]c3cc(Br)ccc3c2C1] | TDI-005855 | 1H NMR (400 MHz, DMSO-d6) δ 11.11 (brd, J = 4.9 Hz, 1H), 7.47 (s, 1H), 7.42-7.34 (m, 1H), 7.13-7.05 (m, 1H), 4.66-4.54 (m, 2H), 4.24-4.13 (m, 2H), 3.86-3.67 (m, 2H), 3.31 (s, 3H), 2.88-2.71 (m, 2H). LC-MS: m/z 325.0 [M + H]$^+$ |
| 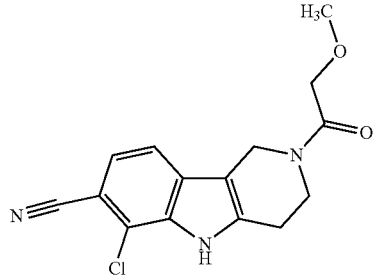 [SMILES: COCC(=O)N1CCc2[nH]c3c(Cl)c(C#N)ccc3c2C1] | TDI-006171 | δ 7.53 (d, J = 8.38 Hz, 1H), 7.35 (d, J = 8.16 Hz, 1H), 4.81-4.71 (m, 2H), 4.30 (d, J = 5.07 Hz, 2H), 4.01 (t, J = 5.73 Hz, 1H), 3.87 (t, J = 5.73 Hz, 1H), 3.43 (d, J = 6.62 Hz, 3H), 3.06-2.91 (m, 2H). |
| 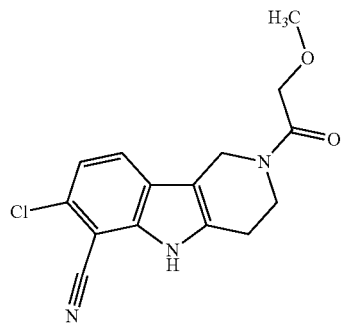 [SMILES: COCC(=O)N1CCc2[nH]c3c(C#N)c(Cl)ccc3c2C1] | TDI-006182 | δ 7.71 (d, J = 8.60 Hz, 1H), 7.21 (d, J = 8.38 Hz, 1H), 4.79-4.69 (m, 2H), 4.30 (d, J = 5.29 Hz, 2H), 4.00 (t, J = 5.84 Hz, 1H), 3.86 (t, J = 5.73 Hz, 1H), 3.43 (d, J = 6.17 Hz, 3H), 3.01-2.95 (m, 1H), 2.90 (brs, 1H). |
| 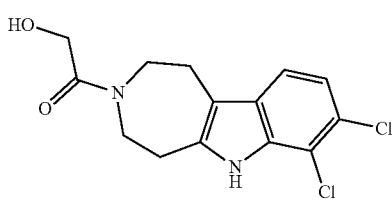 [SMILES: O=C(CO)N1CCc2[nH]c3c(Cl)c(Cl)ccc3c2CC1] | TDI-006183 | 1H NMR (500 MHz, DMSO-d6) δ 11.32 (d, J = 6.7 Hz, 1H), 7.42 (dd, J = 8.4, 4.3 HZ, 1H), 7.16 (dd, J = 8.4, 1.7 Hz, 1H), 4.57 (dt, J = 5.5, 2.8 Hz, 1H), 4.23 (dd, J = 5.6, 2.9 Hz, 2H), 3.74 (dt, J = 16.9, 5.3 Hz, 2H), 3.65 (dt, J = 11.8, 5.4 Hz, 2H), 3.09 (t, J = 5.5 Hz, 1H), 3.02 (t, J = 5.4 Hz, 1H), 2.93 (t, J = 5.5 Hz, 1H), 2.86 (t, J = 5.3 Hz, 1H). LC-MS: m/z 313.1 [M + H]$^+$ |
| 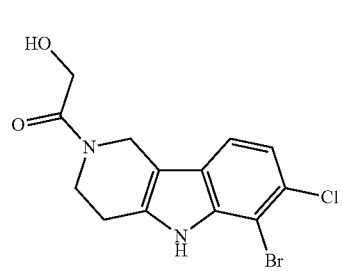 [SMILES: O=C(CO)N1CCc2[nH]c3c(Br)c(Cl)ccc3c2C1] | TDI-006261 | 1H NMR (500 MHz, DMSO-d6) δ 11.35 (d, J = 11.8 Hz, 1H), 7.48 (dd, J = 26.1, 8.3 Hz, 1H), 7.19 (t, J = 8.7 Hz, 1H), 4.73-4.54 (m, 3H), 4.23 (dd, J = 19.8, 5.6 Hz, 2H), 3.79 (dt, J = 88.7, 5.8 Hz, 2H), 2.93-2.78 (m, 2H). |

TABLE 1-continued

Spectroscopic Data for Representative Compounds.

| Structure | ID # | Spectroscopic Data |
|---|---|---|
| 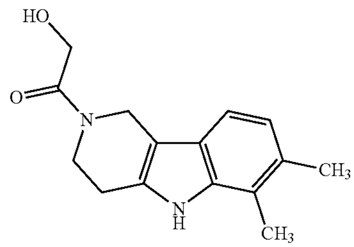 [SMILES: Cc1ccc2c3c([nH]c2c1C)CCN(C(=O)CO)C3] | TDI-006339 | 1H NMR (500 MHz, DMSO-d6) δ 10.66 (d, J = 12.4 Hz, 1H), 7.12 (dd, J = 10.0, 7.9 Hz, 1H), 6.80 (dd, J = 8.0, 2.4 Hz, 1H), 4.68-4.49 (m, 3H), 4.22 (dd, J = 19.8, 5.5 Hz, 2H), 3.79 (dt, J = 97.1, 5.8 Hz, 2H), 2.83 (dt, J = 37.2, 5.9 Hz, 2H), 2.35 (s, 3H), 2.31 (s, 3H). LC-MS: m/z 259.2 [M + H]+ |
| 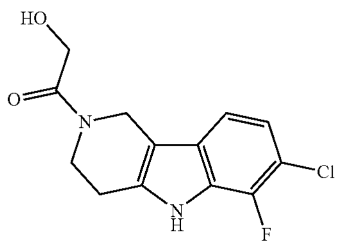 | TDI-006340 | 1H NMR (500 MHz, DMSO-d6) δ 11.68 (d, J = 13.2 Hz, 1H), 7.30 (dd, J = 24.4, 8.5 Hz, 1H), 7.08 (td, J = 8.5, 6.4 Hz, 1H), 4.73-4.53 (m, 3H), 4.23 (dd, J = 18.6, 5.6 Hz, 2H), 3.80 (dt, J = 89.1, 5.7 Hz, 2H), 2.85 (dt, J = 40.9, 6.0 Hz, 2H). LC-MS: m/z 283.1 [M + H]+ |
| 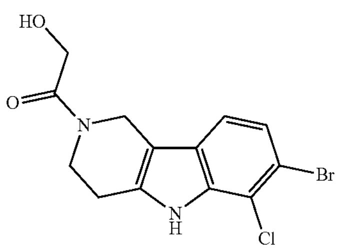 [SMILES: O=C(CO)N1CCc2[nH]c3c(Cl)c(Br)ccc3c2C1] | TDI-006354 | LC-MS: m/z 343.1 [M + H]+ |
| 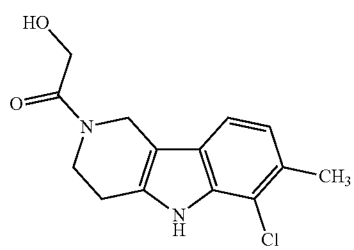 [SMILES: Cc1ccc2c3c([nH]c2c1Cl)CCN(C(=O)CO)C3] | TDI-006358 | 1H NMR (500 MHz, DMSO-d6) δ 11.09 (d, J = 13.6 Hz, 1H), 7.31 (dd, J = 17.7, 7.9 Hz, 1H), 6.96 (dd, J = 8.0, 4.2 Hz, 1H), 4.66 (d, J = 5.7 Hz, 2H), 4.57 (d, J = 19.5 Hz, 1H), 4.23 (dd, J = 18.2, 5.5 Hz, 2H), 3.79 (dt, J = 93.1, 5.8 Hz, 2H), 2.84 (dt, J = 38.3, 5.9 Hz, 2H), 2.42 (s, 3H). LC-MS: m/z 279.2 [M + H]+ |
| 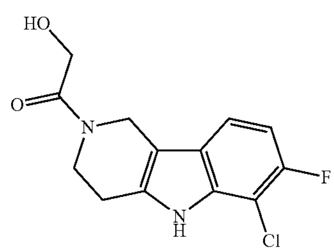 [SMILES: O=C(CO)N1CCc2[nH]c3c(Cl)c(F)ccc3c2C1] | TDI-006359 | 1H NMR (500 MHz, DMSO-d6) δ 11.47 (d, J = 13.5 Hz, 1H), 7.43 (ddd, J = 27.6, 8.6, 4.7 Hz, 1H), 7.04 (dt, J = 10.1, 8.2 Hz, 1H), 4.68 (d, J = 5.1 Hz, 2H), 4.58 (d, J = 15.6 Hz, 1H), 4.23 (dd, J = 18.7, 5.5 Hz, 3H), 3.79 (dt, J = 91.2, 5.7 Hz, 2H), 2.85 (dt, J = 39.2, 5.7 Hz, 2H). LC-MS: m/z 283.1 [M + H]+ |
| 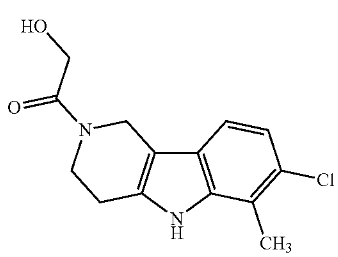 [SMILES: Cc1c(Cl)ccc2c3c([nH]c12)CCN(C(=O)CO)C3] | TDI-006360 | 1H NMR (500 MHz, DMSO-d6) δ 11.09 (d, J = 11.1 Hz, 1H), 7.28 (dd, J = 17.9, 8.4 Hz, 1H), 7.01 (dd, J = 8.4, 6.2 Hz, 1H), 4.72-4.62 (m, 2H), 4.57 (d, J = 14.3 Hz, 1H), 4.23 (dd, J = 20.7, 5.5 Hz, 2H), 3.80 (dt, J = 93.2 5.8 Hz, 2H), 2.85 (dt, J = 38.8, 5.7 Hz, 2H), 2.48 (s, 3H). LC-MS: m/z 279.2 [M + H]+ |

TABLE 1-continued

Spectroscopic Data for Representative Compounds.

| Structure | ID # | Spectroscopic Data |
| --- | --- | --- |
| 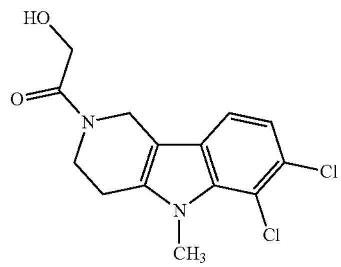 [SMILES: Cn1c2c(c3ccc(Cl)c(Cl)c31)CN(C(=O)CO)CC2] | TDI-006366 | 1H NMR (500 MHz, DMSO-d6) δ 7.47 (dd, J = 24.3, 8.4 Hz, 1H), 7.23 (dd, J = 9.8, 8.2 Hz, 1H), 4.61 (d, J = 45.7 Hz, 3H), 4.31-4.18 (m, 2H), 3.96 (s, 3H), 3.93-3.68 (m, 2H), 2.86 (dt, J = 38.8, 6.0 Hz, 2H). LC-MS: m/z 313.1 [M + H]+ |
| 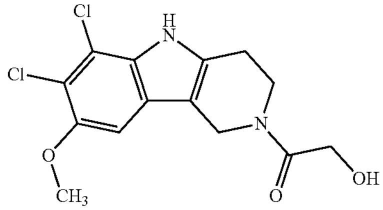 [SMILES: COc1cc2c3c([nH]c2c(Cl)c1Cl)CCN(C(=O)CO)C3] | TDI-006528 | $^1$H NMR (400 MHz, DMSO-d6) δ 7.18 (s, 1H), 4.63 (brs, 2H), 4.22 (s, 2H), 3.89 (s, 3H), 3.78 (brs, 2H), 2.86 (brs, 2H). LC-MS: m/z 329.0 [M + H]+ |
| 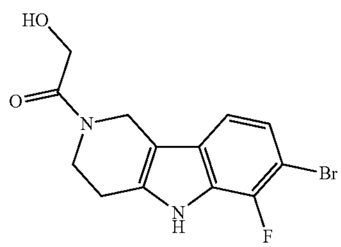 | TDI-006529 | $^1$H NMR (400 MHz, DMSO-d6) δ 11.66 & 11.64 (s, 1H), 7.26-7.14 (m, 2H), 4.65-4.55 (m, 3H), 4.23-4.19 (m, 2H), 3.87 (t, J = 5.2 Hz, 1H), 3.69 (t, J = 5.2 Hz, 1H), 2.86-2.77 (m, 2H). LC-MS: m/z 327.0 [M + H]+ |
| 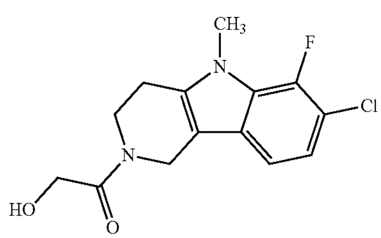 [SMILES: Cn1c2c(c3ccc(Cl)c(F)c31)CN(C(=O)CO)CC2] | TDI-006570 | $^1$H NMR (400 MHz, DMSO-d6) δ 7.32-7.26 (m, 1H), 7.10-7.05 (m, 1H), 4.73-4.55 (m, 2H), 4.23-4.18 (m, 2H), 3.88-3.73 (m, 5H), 2.88-2.80 (m, 2H). LC-MS: m/z 297.1 [M + H]+ |
| 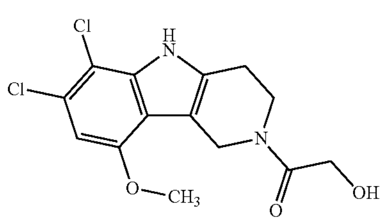 [SMILES: COc1cc(Cl)c(Cl)c2[nH]c3c(c12)CN(C(=O)CO)CC3] | TDI-006622 | $^1$H NMR (400 MHz, DMSO-d6) δ 11.17 (brs, 1H), 6.66 (s, 1H), 4.70 (brs, 2H), 4.37 (brs, 1H), 4.18 (d, J = 5.1 Hz, 2H), 3.87 (s, 3H), 3.72 (brs, 1H), 2.82 (brs, 2H). LC-MS: m/z 329.0 [M + H]+ |
| 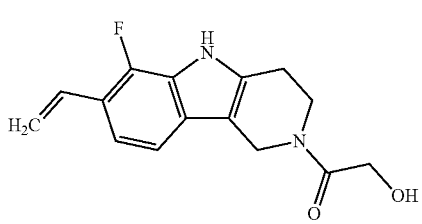 [SMILES: C=Cc1ccc2c3c([nH]c2c1F)CCN(C(=O)CO)C3] | TDI-006923 | $^1$H NMR (400 MHz, MeOD) δ 7.21-7.14 (m, 2H), 6.98 (dd, J$_1$ = 11.6 Hz, J$_2$ = 18.0 Hz, 1H), 5.77 (dd, J$_1$ =1.2 Hz, J$_2$ = 17.6 Hz, 1H), 5.24 (d, J = 8.8 Hz, 1H), 4.75 (s 1H) 4.59 (s, 1H), 4.35 (d, J = 8.8 Hz, 2H), 4.00 (t, J = 5.6 Hz, 1 H), 3.78 (t, J = 5.6 Hz, 1H), 2.93 (t, J = 5.6 Hz, 1H), 2.87 (t, J = 5.6 Hz, 1H). LC-MS: m/z 275.1 [M + H]+ |

TABLE 1-continued

Spectroscopic Data for Representative Compounds.

| Structure | ID # | Spectroscopic Data |
| --- | --- | --- |
| 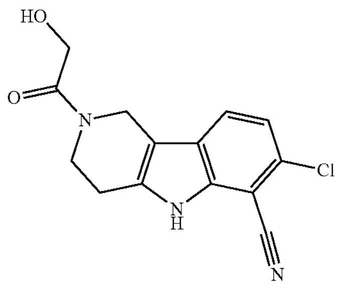 [SMILES: N#Cc1c(Cl)ccc2c3c([nH]c12)CCN(C(=O)CO)C3] | TDI-006931 | $^1$H NMR (500 MHz, DMSO-d$_6$) δ 12.08 (d, J = 8.5 Hz, 1H), 8.13-7.72 (m, 1H), 7.28 (dd, J = 11.0, 8.3 Hz, 1H), 4.78-4.55 (m, 2H), 4.23 (dd, J = 20.4, 5.6 Hz, 2H), 3.80 (dt, J = 87.6, 5.7 Hz, 2H), 2.97-2.80 (m, 2H). LC-MS: m/z 290.2 [M + H]$^+$ |
| 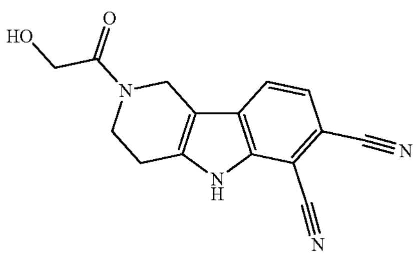 [SMILES: N#Cc1ccc2c3c([nH]c2c1C#N)CCN(C(=O)CO)C3] | TDI-006932 | $^1$H NMR (500 MHz, DMSO-d$_6$) δ 12.55 (s, 1H), 8.19-7.86 (m, 1H), 7.63 (t, J = 8.3 Hz, 1H), 4.74 (s, 2H), 4.24 (dd, J = 22.3, 5.4 Hz, 2H), 3.83 (dt, J = 83.9, 5.8 Hz, 2H), 3.06-2.86 (m, 2H). LC-MS: m/z 281.2 [M + H]$^+$ |
| 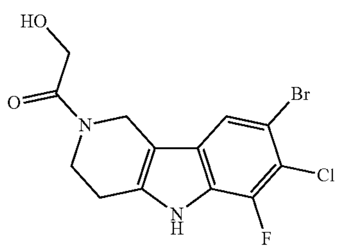 [SMILES: O=C(CO)N1CCc2[nH]c3c(F)c(Cl)c(Br)cc3c2C1] | TDI-007362 | $^1$H NMR (500 MHz, DMSO-d$_6$) δ 11.88 (d, J = 13.6 Hz, 1H), 7.78 (d, J = 31.3 Hz, 1H), 4.73-4.53 (m, 3H), 4.22 (dd, J = 24.8, 5.6 Hz, 2H), 3.79 (dt, J = 88.1, 5.8 Hz, 2H), 2.85 (dt, J = 41.3, 5.4 Hz, 2H). LC-MS: m/z 363.1 [M + H]$^+$ |
| 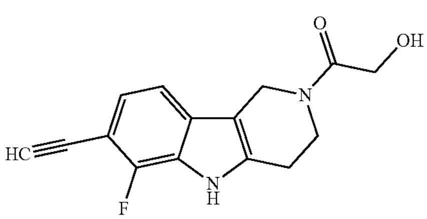 [SMILES: C#Cc1ccc2c3c([nH]c2c1F)CCN(C(=O)CO)C3] | TDI-007433 | $^1$H NMR (400 MHz, MeOD) δ 8.48-8.45 (m, 1H), 7.34 (s, 1H), 4.80 (s, 1H), 4.73 (s, 1H), 4.29 (s, 2H), 4.00 (t, J = 5.8 Hz, 1H), 3.86 (t, J = 5.7 Hz, 1H), 3.42 (d, J = 3.5 Hz, 3H), 2.95-2.86 (m, 2H). LC-MS: m/z 273.0 [M + H]$^+$ |
| 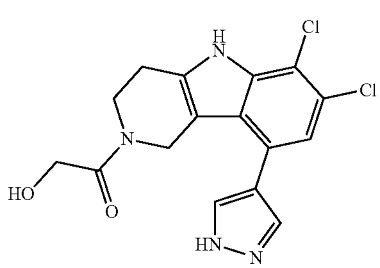 [SMILES: O=C(CO)N1CCc2[nH]c3c(Cl)c(Cl)cc(-c4cn[nH]c4)c3c2C1] | TDI-007445 | $^1$H NMR: (CD$_3$OD, 400 MHz) δ 7.84 (brs, 1H), 7.73 (brs, 1H), 7.02 (s, 1H), 4.46 (s, 1H), 4.31 (s, 1H), 4.19 (s, 1H), 4.06 (s, 1H), 3.94 (t, J = 5.6 Hz, 1H), 3.74 (t, J = 5.6 Hz, 1H), 2.89 (t, J = 5.6 Hz, 1H), 2.95 (t, J = 5.6 Hz, 1H). LCMS: m/z 365.0 [M + H]$^+$ |
| 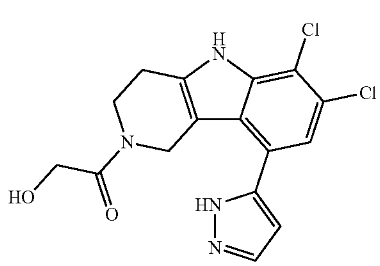 [SMILES: O=C(CO)N1CCc2[nH]c3c(Cl)c(Cl)cc(-c4ccn[nH]4)c3c2C1] | TDI-007457 | $^1$H NMR: (CD$_3$OD, 400 MHz) δ 7.77 (s, 1H), 7.20-7.18 (m, 1H), 6.53-6.51 (m, 1H), 4.50 (s, 1H), 4.39-4.30 (m, 2H), 4.15 (s, 1H), 3.94 (t, J = 6.0 Hz, 1H), 3.74 (t, J = 5.6 Hz, 1H), 2.97-2.90 (m, 2H). LC-MS: m/z 364.9 [M + H]$^+$ |

TABLE 1-continued

Spectroscopic Data for Representative Compounds.

| Structure | ID # | Spectroscopic Data |
|---|---|---|
| 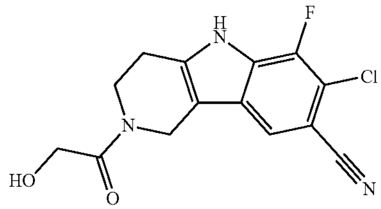 [SMILES: N#Cc1cc2c3c([nH]c2c(F)c1Cl)CCN(C(=O)CO)C3] | TDI-007542 | $^1$H NMR (400 MHz, DMSO-d$_6$, T = 80° C.) δ 12.10 (br.s, 1H), 7.99 (s, 1H), 4.67 (s, 2H), 4.39 (br.s, 1H), 4.22-4.21 (m, 2H), 3.82 (s, 2H), 2.90-2.89 (m, 2H). LC-MS: m/z 308.0 [M + H]$^+$ |
| 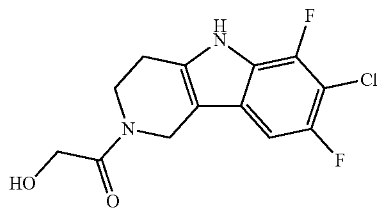 [SMILES: O=C(CO)N1CCc2[nH]c3c(F)c(Cl)c(F)cc3c2C1] | TDI-007544 | $^1$H NMR (400 MHz, CD$_3$OD): δ 7.15 (t, J = 8.0 Hz, 1H), 4.73 (s, 1H), 4.61-4.57 (m, 1H), 4.36 (d, J = 11.2 Hz, 2H), 4.00 (t, J = 6.0 Hz, 1H), 3.78 (t, J = 6.0 Hz, 1H), 2.95-2.87 (m, 2H). LC-MS: m/z 301.0 [M + H]$^+$ |
| 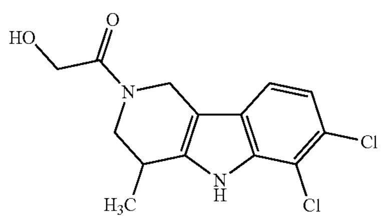 [SMILES: CC1CN(C(=O)CO)Cc2c1[nH]c1c(Cl)c(Cl)ccc21] | TDI-007553 | $^1$H NMR (400 MHz, CD$_3$OD) δ 7.34 (dd, J = 4.5, 8.4 Hz, 1H), 7.12 (d, J = 8.4 Hz, 1H), 4.82-4.68 (m, 1H), 4.59 (q, J = 15.2 Hz, 1H), 4.43-4.31 (m, 2H), 3.87 (brd, J = 4.8 Hz, 1H), 3.80 (dd, J = 4.5, 13.9 Hz, 0.5H), 3.46 (dd, J = 5.8, 13.6 Hz, 0.5H), 3.24-3.08 (m, 1H), 1.36 (dd, J = 7.0, 14.8 Hz, 3H). LC-MS: m/z 313.1 [M + H]$^+$ |
| 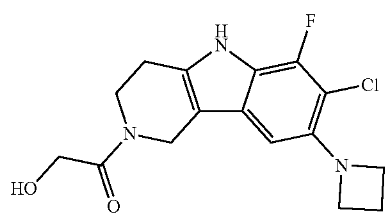 [SMILES: O=C(CO)N1CCc2[nH]c3c(F)c(Cl)c(N4CCC4)cc3c2C1] | TDI-007560 | $^1$H NMR (400 MHz, DMSO-d$_6$, T = 80° C.) δ 10.93 (br.s, 1H), 6.49 (s, 1H), 4.58 (s, 2H), 4.32 (s, 1H), 4.21 (t, J = 5.6 Hz, 2H), 3.94 (t, J = 6.8 Hz, 4H), 3.80 (s, 2H), 2.82 (t, J = 3.2 Hz, 2H), 2.27-2.20 (m, 2H). LC-MS: m/z 338.0 [MS + H]$^+$ |
| 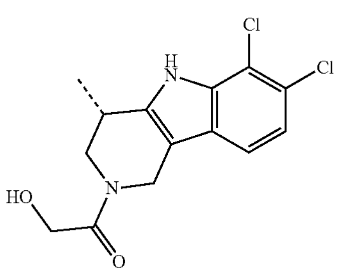 [SMILES: C[C@H]1CN(C(=O)CO)Cc2c1[nH]c1c(Cl)c(Cl)ccc21] | TDI-007575 | $^1$H NMR (400 MHz, CD$_3$OD) δ 7.34 (dd, J = 3.9, 8.3 Hz, 1H), 7.12 (d, J = 8.4 Hz, 1H), 4.71-4.68 (m, 1H), 4.67-4.51 (m, 1H), 4.37 (s, 2H), 3.86 (brd, J = 5.0 Hz, 1H), 3.80 (dd, J = 4.6, 13.9 Hz, 1H), 3.46 (dd, J = 5.6, 13.5 Hz, 1H), 3.23-3.11 (m, 1H), 1.36 (dd, J = 6.8, 14.5 Hz, 3H). LC-MS: m/z 313.1 [MS + H]$^+$ |
| 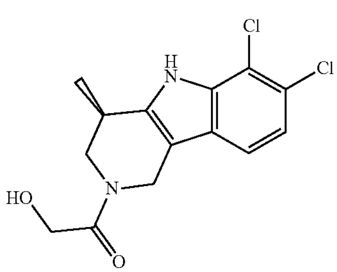 [SMILES: C[C@@H]1CN(C(=O)CO)Cc2c1[nH]c1c(Cl)c(Cl)ccc21] | TDI-007576 | $^1$H NMR (400 MHz, CD$_3$OD) δ 7.33 (dd, J = 4.1, 8.4 Hz, 1H), 7.11 (d, J = 8.4 Hz, 1H), 4.68-4.63 (m, 1H), 4.58 (brd, J = 14.9 Hz, 1H), 4.38-4.34 (m, 2H), 3.86 (dd, J = 2.9, 4.8 Hz, 1H), 3.79 (dd, J = 4.6, 13.9 Hz, 0.5H), 3.45 (dd, J = 5.9, 13.8 Hz, 0.5H), 3.17 (td, J = 6.3, 13.0 Hz, 1H), 1.35 (dd, J = 6.9, 14.5 Hz, 3H). LC-MS: m/z 313.1 [MS + H]$^+$ |

TABLE 1-continued

Spectroscopic Data for Representative Compounds.

| Structure | ID # | Spectroscopic Data |
|---|---|---|
| 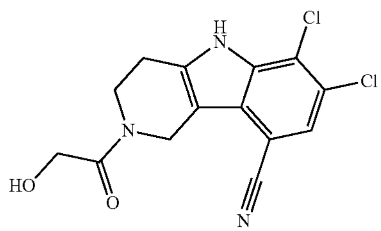 [SMILES: N#Cc1cc(Cl)c(Cl)c2[nH]c3c(c12)CN(C(=O)CO)CC3] | TDI-007586 | $^1$H NMR (DMSO-d$_6$, 400 MHz) δ 7.70 (s, 1H), 4.87 (s, 2H), 4.40 (br. s, 1H), 4.23 (s, 2H), 3.81 (t, J = 5.4 Hz, 2H), 2.96-2.94 (m, 2H). LC-MS: m/z 324.0 [MS + H]$^+$ |
| 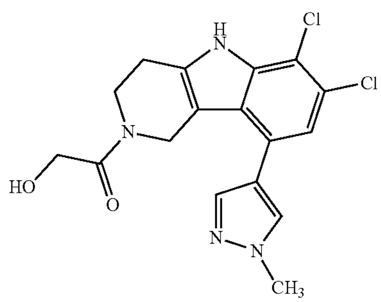 [SMILES: Cn1cc(-c2cc(Cl)c(Cl)c3[nH]c4c(c23)CN(C(=O)CO)CC4)cn1] | TDI-007635 | $^1$H NMR (DMSO-d$_6$, 400 MHz, T = 80) δ 11.23 (br. s, 1H), 7.84 (s, 1H), 7.56 (s, 1H), 7.01 (s, 1H), 4.34 (s, 2H), 4.10 (s, 2H), 3.93 (s, 3H), 3.76 (t, J = 5.2 Hz, 2H), 2.89 (t, J = 5.2 Hz, 2H). LC-MS: m/z 379.0, 381.0 [MS + H]$^+$ |
| 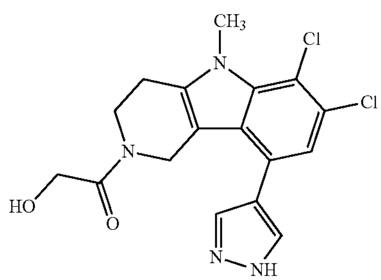 [SMILES: Cn1c2c(c3c(-c4cn[nH]c4)cc(Cl)c(Cl)c31)CN(C(=O)CO)CC2] | TDI-007945 | $^1$H NMR (DMSO-d$_6$, 400 MHz, T = 80) δ 7.73 (s, 2H), 7.03 (s, 1H), 4.19-4.05 (m, 4H), 3.98 (s, 3H), 3.76 (s, 2H), 2.86 (s, 2H). LC-MS: m/z 379.0, 381.0 [MS + H]$^+$ |
| 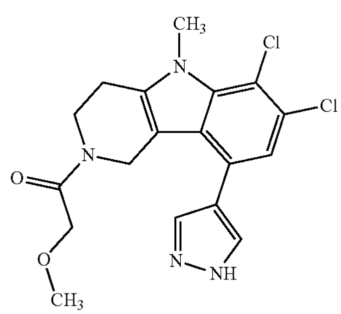 [SMILES: COCC(=O)N1CCc2c(c3c(-c4cn[nH]c4)cc(Cl)c(Cl)c3n2C)C1] | TDI-008026 | $^1$H NMR (DMSO-d$_6$, 400 MHz, T = 80) δ 7.74 (s, 2H), 7.03 (s, 1H), 4.22 (s, 2 H), 4.08-4.00 (m, 2H), 3.99 (s, 3H), 3.78 (t, J = 6.0 Hz, 2H), 3.25 (s, 3H), 2.86 (s, 2H). |
| 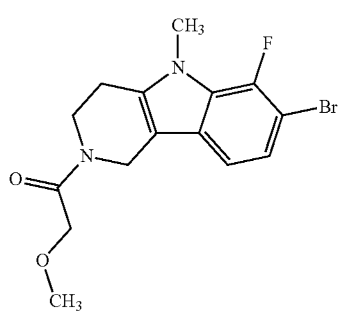 [SMILES: COCC(=O)N1CCc2c(c3ccc(Br)c(F)c3n2C)C1] | TDI-008034 | $^1$H NMR (400 MHz, CD$_3$OD) δ 7.13 (t, J = 2.9 Hz, 2H), 4.72 (s, 1H), 4.64 (s, 1H), 4.28 (d, J = 11.4 Hz, 2H), 4.01 (t, J = 5.7 Hz, 1H), 3.86 (t, J = 5.7 Hz, 1H), 3.83 (s, 3H), 3.42 (d, J = 8.8 Hz, 3H), 2.94-2.82 (m, 2H). |

TABLE 1-continued

Spectroscopic Data for Representative Compounds.

| Structure | ID # | Spectroscopic Data |
|---|---|---|
| 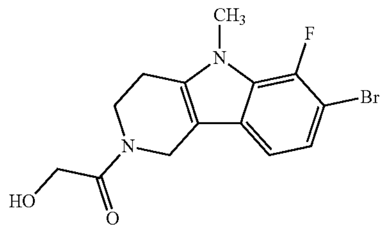 [SMILES: Cn1c2c(c3ccc(Br)c(F)c31)CN(C(=O)CO)CC2] | TDI-008061 | $^1$H NMR (DMSO-d$_6$, 400 MHz) δ 7.30-7.14 (m, 2H), 4.75-4.54 (m, 3H), 4.27-4.14 (m, 2H), 3.92-3.69 (m, 5H), 2.93-2.75 (m, 2H). LC-MS: m/z 341.0 [M + H]$^+$ |
| 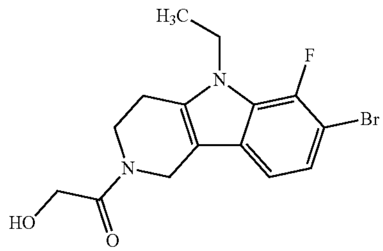 [SMILES: CCn1c2c(c3ccc(Br)c(F)c31)CN(C(=O)CO)CC2] | TDI-008062 | $^1$H NMR (DMSO-d$_6$, 400 MHz) δ 7.36-7.09 (m, 2H), 4.80-4.49 (m, 3H), 4.33-4.12 (m, 4H), 3.97-3.66 (m, 2H), 2.94-2.75 (m, 2H), 1.27 (t, J = 7.1 Hz, 3H). LC-MS: m/z 355.0 [M + H]$^+$ |
| 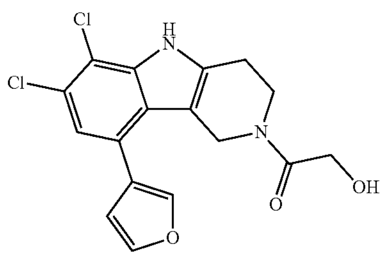 [SMILES: O=C(CO)N1CCc2[nH]c3c(Cl)c(Cl)cc(-c4ccoc4)c3c2C1] | TDI-008069 | LC-MS: m/z 365.1 [M + H]$^+$ |
| 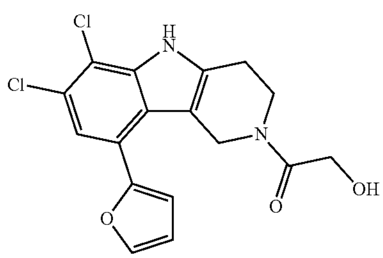 [SMILES: O=C(CO)N1CCc2[nH]c3c(Cl)c(Cl)cc(-c4ccco4)c3c2C1] | TD1-008070 | LC-MS: m/z 365.1 [M + H]$^+$ |
| 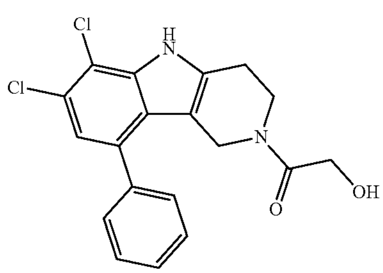 [SMILES: O=C(CO)N1CCc2[nH]c3c(Cl)c(Cl)cc(-c4ccccc4)c3c2C1] | TDI-008071 | LC-MS: m/z 375.1 [M + H]$^+$ |
| 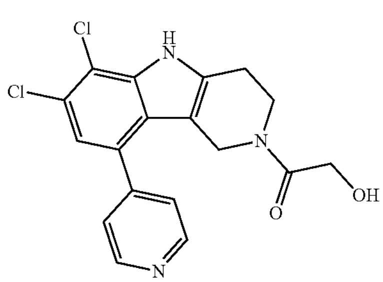 [SMILES: O=C(CO)N1CCc2[nH]c3c(Cl)c(Cl)cc(-c4ccncc4)c3c2C1] | TDI-008072 | LC-MS: m/z 376.1 [M + H]$^+$ |

TABLE 1-continued

Spectroscopic Data for Representative Compounds.

| Structure | ID # | Spectroscopic Data |
|---|---|---|
| 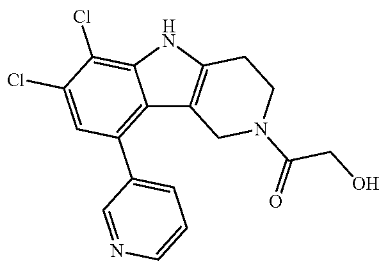 [SMILES: O=C(CO)N1CCc2[nH]c3c(Cl)c(Cl)cc(-c4cccnc4)c3c2C1] | TDI-008073 | LC-MS: m/z 376.1 [M + H]+ |
| 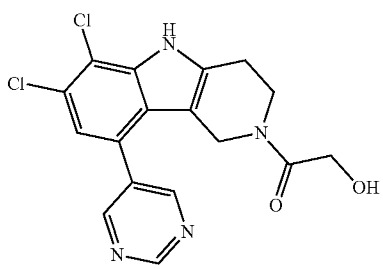 [SMILES: O=C(CO)N1CCc2[nH]c3c(Cl)c(Cl)cc(-c4cncnc4)c3c2C1] | TDI-008074 | LC-MS: m/z 377.1 [M + H]+ |
| 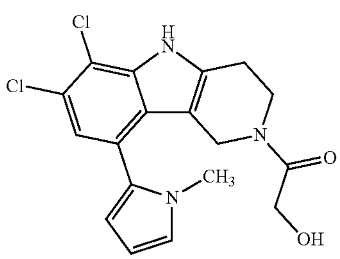 [SMILES: Cn1cccc1-c1cc(Cl)c(Cl)c2[nH]c3c(c12)CN(C(=O)CO)CC3] | TDI-008075 | LC-MS: m/z 378.1 [M + H]+ |
| 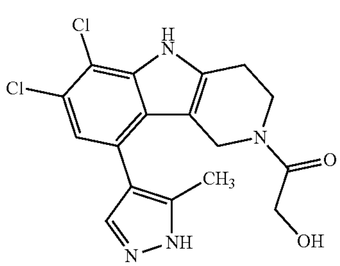 [SMILES: Cc1[nH]ncc1-c1cc(Cl)c(Cl)c2[nH]c3c(c12)CN(C(=O)CO)CC3] | TDI-008076 | LC-MS: m/z 379.1 [M + H]+ |
| 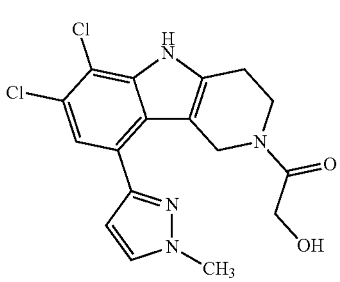 [SMILES: Cn1ccc(-c2cc(Cl)c(Cl)c3[nH]c4c(c23)CN(C(=O)CO)CC4)n1] | TDI-008077 | $^1$H NMR (DMSO-d$_6$, 400 MHz) δ 11.33 (brs, 1H), 7.73 (d, J = 2.2 Hz, 1H), 7.22 (s, 1H), 6.52 (brs, 1H), 4.57 (s, 2H), 4.32-4.26 (m, 1H), 4.13 (brs, 2H), 3.94 (s, 3H), 3.76 (brs, 2H), 2.88 (brs, 2H). LC-MS: m/z 379.0 [M + H]+ |

TABLE 1-continued

Spectroscopic Data for Representative Compounds.

| Structure | ID # | Spectroscopic Data |
|---|---|---|
| 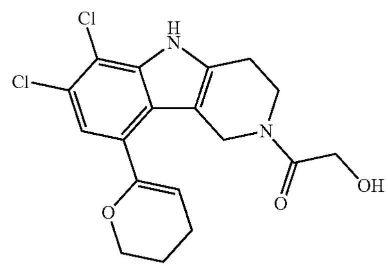 [SMILES: O=C(CO)N1CCc2[nH]c3c(Cl)c(Cl)cc(C4=CCCCO4)c3c2C1] | TDI-008078 | LC-MS: m/z 381.1 [M + H]+ |
| 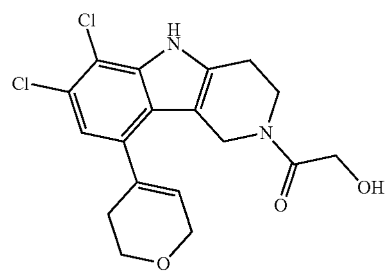 [SMILES: O=C(CO)N1CCc2[nH]c3c(Cl)c(Cl)cc(C4=CCOCC4)c3c2C1] | TDI-008079 | LC-MS: m/z 381.1 [M + H]+ |
| 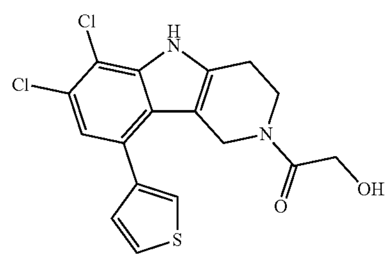 | TDI-008080 | LC-MS: m/z 381.0 [M + H]+ |
| 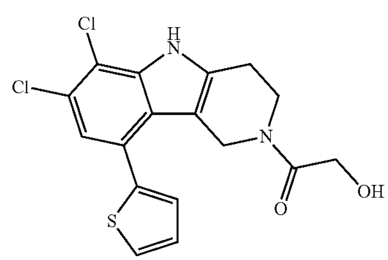 | TDI-008081 | LC-MS: m/z 381.1 [M + H]+ |
| 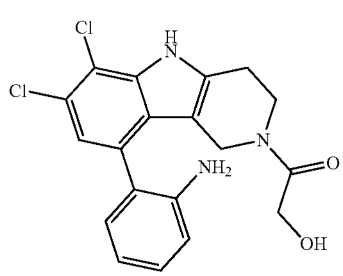 [SMILES: Nc1ccccc1-c1cc(Cl)c(Cl)c2[nH]c3c(c12)CN(C(=O)CO)CC3] | TDI-008082 | LC-MS: m/z 390.1 [M + H]+ |

TABLE 1-continued

Spectroscopic Data for Representative Compounds.

| Structure | ID # | Spectroscopic Data |
|---|---|---|
| 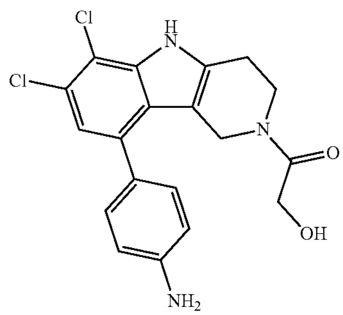 [SMILES: Nc1ccc(-c2cc(Cl)c(Cl)c3[nH]c4c(c23)CN(C(=O)CO)CC4)cc1] | TDI-008083 | LC-MS: m/z 390.1 [M + H]+ |
| 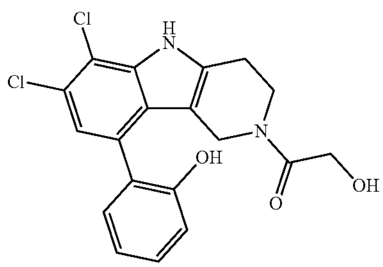 [SMILES: O=C(CO)N1CCc2[nH]c3c(Cl)c(Cl)cc(-c4ccccc4O)c3c2C1] | TDI-008084 | LC-MS: m/z 391.1 [M + H]+ |
| 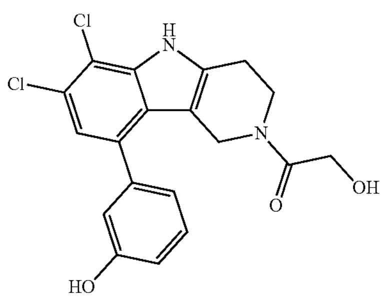 [SMILES: O=C(CO)N1CCc2[nH]c3c(Cl)c(Cl)cc(-c4cccc(O)c4)c3c2C1] | TDI-008085 | LC-MS: m/z 391.1 [M + H]+ |
| 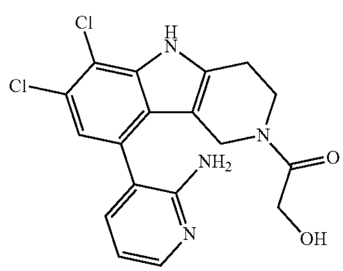 [SMILES: Nc1ncccc1-c1cc(Cl)c(Cl)c2[nH]c3c(c12)CN(C(=O)CO)CC3] | TDI-008086 | LC-MS: m/z 391.1 [M + H]+ |
| 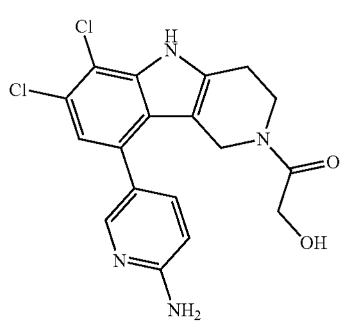 [SMILES: Nc1ccc(-c2cc(Cl)c(Cl)c3[nH]c4c(c23)CN(C(=O)CO)CC4)cn1] | TDI-008087 | LC-MS: m/z 391.1 [M + H]+ |

TABLE 1-continued

Spectroscopic Data for Representative Compounds.

| Structure | ID # | Spectroscopic Data |
|---|---|---|
| 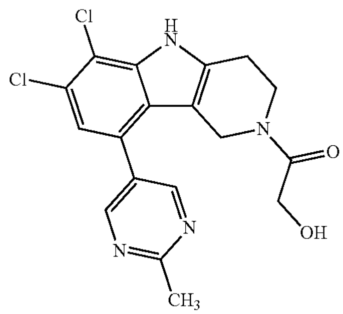 [SMILES: Cc1ncc(-c2cc(Cl)c(Cl)c3[nH]c4c(c23)CN(C(=O)CO)CC4)cn1] | TDI-008088 | LC-MS: m/z 391.1 [M + H]$^+$ |
| 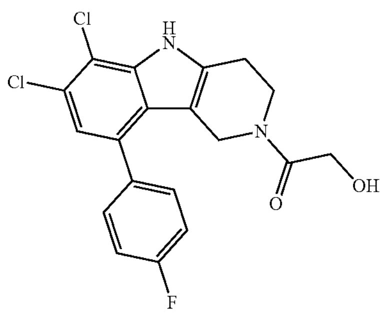 [SMILES: O=C(CO)N1CCc2[nH]c3c(Cl)c(Cl)cc(-c4ccc(F)cc4)c3c2C1] | TDI-008089 | LC-MS: m/z 393.0 [M + H]$^+$ |
| 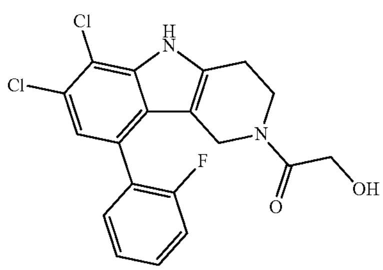 [SMILES: O=C(CO)N1CCc2[nH]c3c(Cl)c(Cl)cc(-c4ccccc4F)c3c2C1] | TDI-008090 | LC-MS: m/z 393.1 [M + H]$^+$ |
| 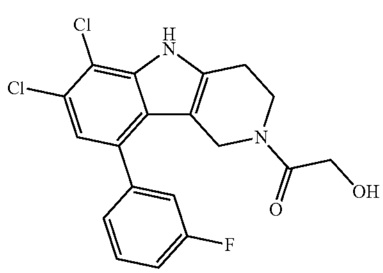 [SMILES: O=C(CO)N1CCc2[nH]c3c(Cl)c(Cl)cc(-c4cccc(F)c4)c3c2C1] | TDI-008091 | LC-MS: m/z 393.0 [M + H]$^+$ |
| 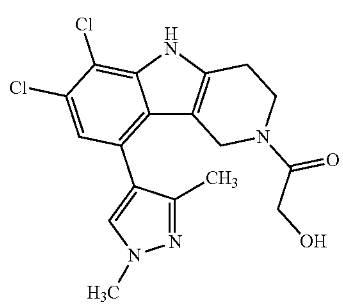 [SMILES: Cc1nn(C)cc1-c1cc(Cl)c(Cl)c2[nH]c3c(c12)CN(C(=O)CO)CC3] | TDI-008092 | LC-MS: m/z 393.1 [M + H]$^+$ |

TABLE 1-continued

Spectroscopic Data for Representative Compounds.

| Structure | ID # | Spectroscopic Data |
|---|---|---|
| 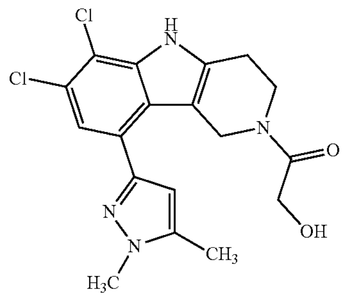 [SMILES: Cc1cc(-c2cc(Cl)c(Cl)c3[nH]c4c(c23)CN(C(=O)CO)CC4)nn1C] | TDI-008093 | LC-MS: m/z 393.1 [M + H]+ |
| 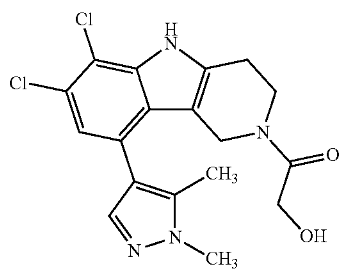 [SMILES: Cc1c(-c2cc(Cl)c(Cl)c3[nH]c4c(c23)CN(C(=O)CO)CC4)cnn1C] | TDI-008094 | LC-MS: m/z 393.1 [M + H]+ |
| 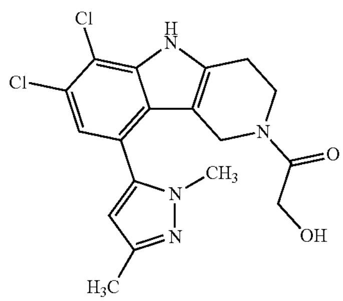 [SMILES: Cc1cc(-c2cc(Cl)c(Cl)c3[nH]c4c(c23)CN(C(=O)CO)CC4)n(C)n1] | TDI-008095 | LC-MS: m/z 393.1 [M + H]+ |
| 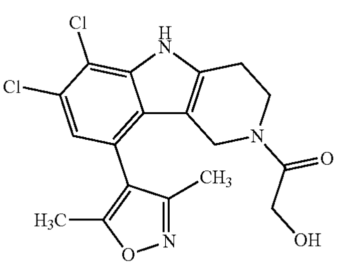 [SMILES: Cc1noc(C)c1-c1cc(Cl)c(Cl)c2[nH]c3c(c12)CN(C(=O)CO)CC3] | TDI-008096 | LC-MS: m/z 394.1 [M + H]+ |
| 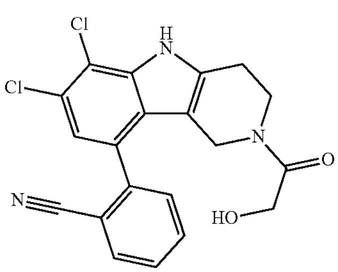 [SMILES: N#Cc1ccccc1-c1cc(Cl)c(Cl)c2[nH]c3c(c12)CN(C(=O)CO)CC3] | TDI-008097 | LC-MS: m/z 400.0 [M + H]+ |

TABLE 1-continued

Spectroscopic Data for Representative Compounds.

| Structure | ID # | Spectroscopic Data |
| --- | --- | --- |
| 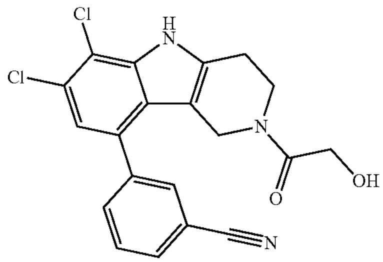 [SMILES: N#Cc1cccc(-c2cc(Cl)c(Cl)c3[nH]c4c(c23)CN(C(=O)CO)CC4)c1] | TDI-008098 | LC-MS: m/z 400.0 [M + H]+ |
| 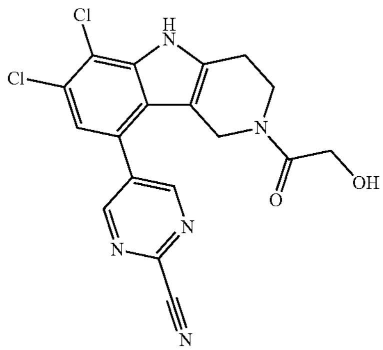 [SMILES: N#Cc1ncc(-c2cc(Cl)c(Cl)c3[nH]c4c(c23)CN(C(=O)CO)CC4)cn1] | TDI-008100 | LC-MS: m/z 402.0 [M + H]+ |
| 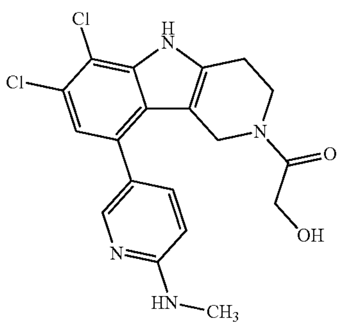 [SMILES: CNc1ccc(-c2cc(Cl)c(Cl)c3[nH]c4c(c23)CN(C(=O)CO)CC4)cn1] | TDI-008101 | LC-MS: m/z 405.1 [M + H]+ |
| 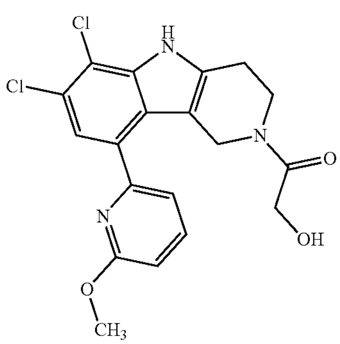 [SMILES: COc1cccc(-c2cc(Cl)c(Cl)c3[nH]c4c(c23)CN(C(=O)CO)CC4)n1] | TDI-008102 | LC-MS: m/z 406.1 [M + H]+ |
| 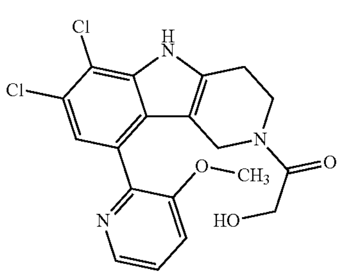 [SMILES: COc1cccnc1-c1cc(Cl)c(Cl)c2[nH]c3c(c12)CN(C(=O)CO)CC3] | TDI-008103 | LC-MS: m/z 406.1 [M + H]+ |

TABLE 1-continued

Spectroscopic Data for Representative Compounds.

| Structure | ID # | Spectroscopic Data |
|---|---|---|
| 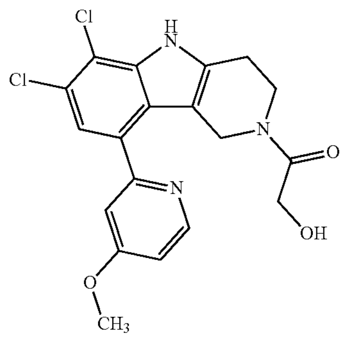 [SMILES: COc1ccnc(-c2cc(Cl)c(Cl)c3[nH]c4c(c23)CN(C(=O)CO)CC4)c1] | TDI-008104 | LC-MS: m/z 406.0 [M + H]+ |
| 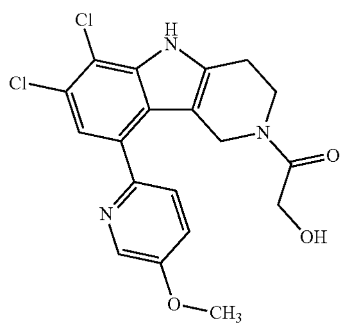 [SMILES: COc1ccc(-c2cc(Cl)c(Cl)c3[nH]c4c(c23)CN(C(=O)CO)CC4)nc1] | TDI-008105 | LC-MS: m/z 406.1 [M + H]+ |
| 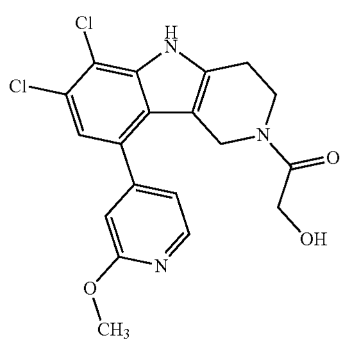 [SMILES: COc1cc(-c2cc(Cl)c(Cl)c3[nH]c4c(c23)CN(C(=O)CO)CC4)ccn1] | TDI-008106 | LC-MS: m/z 406.0 [M + H]+ |
| 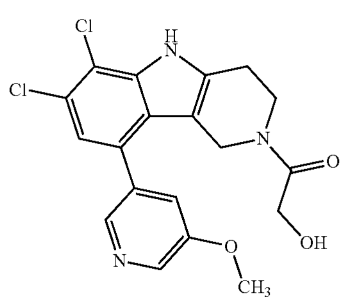 [SMILES: COc1cncc(-c2cc(Cl)c(Cl)c3[nH]c4c(c23)CN(C(=O)CO)CC4)c1] | TDI-008107 | LC-MS: m/z 406.1 [M + H]+ |

TABLE 1-continued

Spectroscopic Data for Representative Compounds.

| Structure | ID # | Spectroscopic Data |
|---|---|---|
| 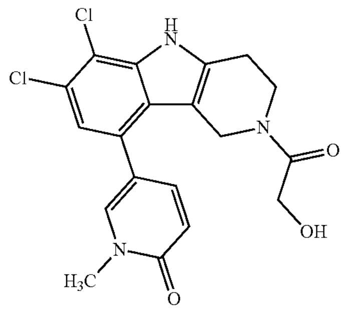 [SMILES: Cn1cc(-c2cc(Cl)c(Cl)c3[nH]c4c(c23)CN(C(=O)CO)CC4)ccc1=O] | TDI-008108 | LC-MS: m/z 406.1 [M + H]$^+$ |
| 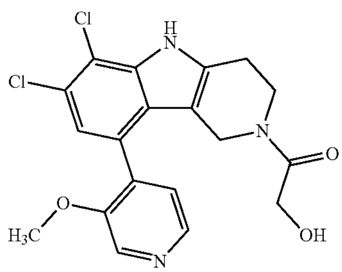 [SMILES: COc1cnccc1-c1cc(Cl)c(Cl)c2[nH]c3c(c12)CN(C(=O)CO)CC3] | TDI-008109 | LC-MS: m/z 406.0 [M + H]$^+$ |
| 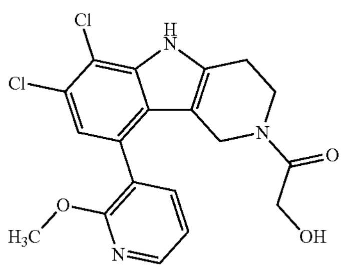 [SMILES: COc1ncccc1-c1cc(Cl)c(Cl)c2[nH]c3c(c12)CN(C(=O)CO)CC3] | TDI-008110 | LC-MS: m/z 406.0 [M + H]$^+$ |
| 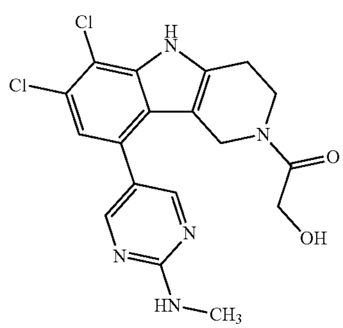 [SMILES: CNc1ncc(-c2cc(Cl)c(Cl)c3[nH]c4c(c23)CN(C(=O)CO)CC4)cn1] | TDI-008111 | LC-MS: m/z 406.1 [M + H]$^+$ |
| 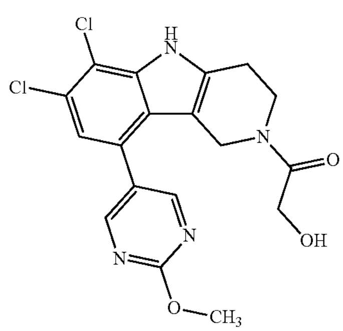 [SMILES: COc1ncc(-c2cc(Cl)c(Cl)c3[nH]c4c(c23)CN(C(=O)CO)CC4)cn1] | TDI-008112 | LC-MS: m/z 407.1 [M + H]$^+$ |

TABLE 1-continued

Spectroscopic Data for Representative Compounds.

| Structure | ID # | Spectroscopic Data |
|---|---|---|
| 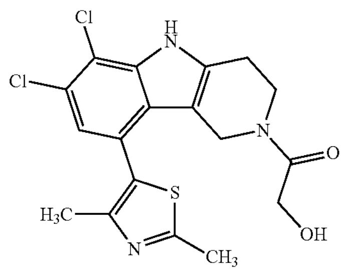 [SMILES: Cc1nc(C)c(-c2cc(Cl)c(Cl)c3[nH]c4c(c23)CN(C(=O)CO)CC4)s1] | TDI-008113 | LC-MS: m/z 409.9 [M + H]+ |
| 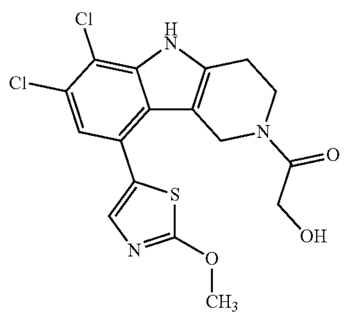 [SMILES: COc1ncc(-c2cc(Cl)c(Cl)c3[nH]c4c(c23)CN(C(=O)CO)CC4)s1] | TDI-008114 | LC-MS: m/z 412.0 [M + H]+ |
| 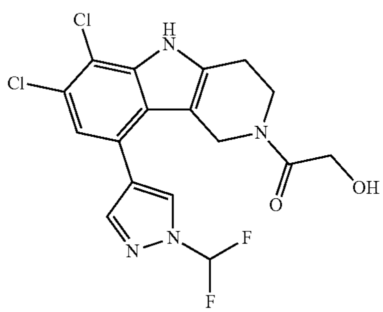 [SMILES: O=C(CO)N1CCc2[nH]c3c(Cl)c(Cl)cc(-c4cnn(C(F)F)c4)c3c2C1] | TDI-008115 | LC-MS: m/z 415.0 [M + H]+ |
| 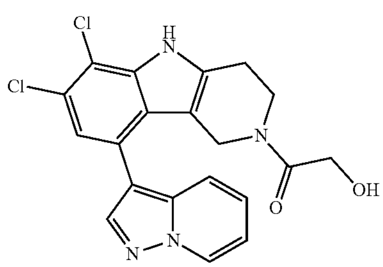 [SMILES: O=C(CO)N1CCc2[nH]c3c(Cl)c(Cl)cc(-c4cnn5ccccc45)c3c2C1] | TDI-008116 | LC-MS: m/z 415.0 [M + H]+ |
| 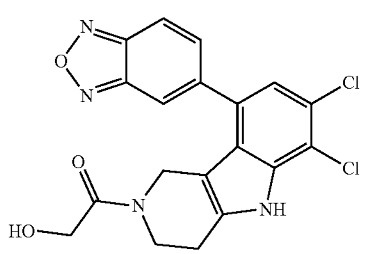 [SMILES: O=C(CO)N1CCc2[nH]c3c(Cl)c(Cl)cc(-c4ccc5nonc5c4)c3c2C1] | TDI-008117 | LC-MS: m/z 417.0 [M + H]+ |

TABLE 1-continued

Spectroscopic Data for Representative Compounds.

| Structure | ID # | Spectroscopic Data |
|---|---|---|
| 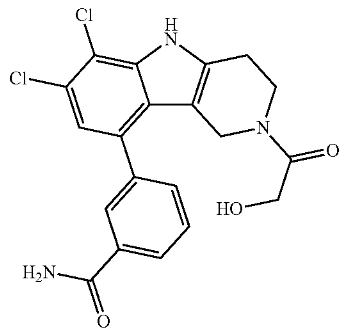 [SMILES: NC(=O)c1cccc(-c2cc(Cl)c(Cl)c3[nH]c4c(c23)CN(C(=O)CO)CC4)c1] | TDI-008118 | LC-MS: m/z 418.1 [M + H]+ |
| 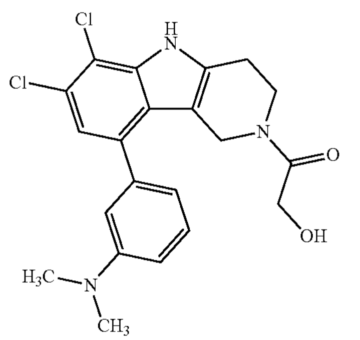 [SMILES: CN(C)c1cccc(-c2cc(Cl)c(Cl)c3[nH]c4c(c23)CN(C(=O)CO)CC4)c1] | TDI-008120 | LC-MS: m/z 418.1 [M + H]+ |
| 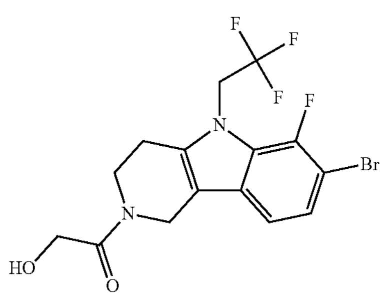 [SMILES: O=C(CO)N1CCc2c(c3ccc(Br)c(F)c3n2CC(F)(F)F)C1] | TDI-008130 | $^1$H NMR (DMSO-d$_6$, 400 MHz) δ 7.39-7.26 (m, 2H), 5.14 (q, J = 9.2 Hz, 2H), 4.81-4.56 (m, 3H), 4.26-4.17 (m, 2H), 3.92-3.70 (m, 2H), 2.93-2.78 (m, 2H). LC-MS: m/z 411.0 [M + H]+ |
| 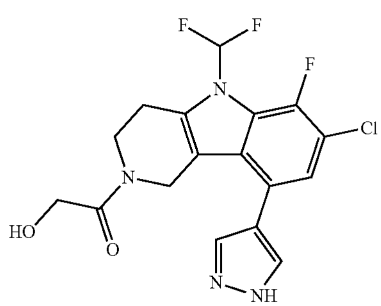 [SMILES: O=C(CO)N1CCc2c(c3c(-c4cn[nH]c4)cc(Cl)c(F)c3n2C(F)F)C1] | TDI-008136 | $^1$H NMR (DMSO-d$_6$, 400 MHz) δ 13.11 (brs, 1H), 8.11-7.62 (m, 3H), 7.19 (d, J = 6.4 Hz, 1H), 4.72-4.59 (m, 1H), 4.26 (brs, 1H), 4.16 (brd, J = 5.3 Hz, 1H), 4.11-3.86 (m, 1H), 3.84-3.65 (m, 2H), 3.09-2.88 (m, 2H). LC-MS: m/z 399.1 [M + H]+ |
| 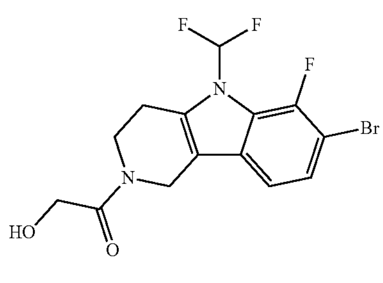 [SMILES: O=C(CO)N1CCc2c(c3ccc(Br)c(F)c3n2C(F)F)C1] | TDI-008179 | $^1$H NMR (DMSO-d$_6$, 400 MHz) δ 7.84-7.46 (m, 1H), 7.39-7.29 (m, 1H), 7.09 (brdd, J = 8.1, 16.4 Hz, 1H), 4.82 (brs, 1H), 4.43 (brs, 1H), 4.30 (brd, J = 11.8 Hz, 2H), 4.08 (brt, J = 5.5 Hz, 1H), 3.69-3.59 (m, 2H), 3.09 (brd, J = 5.7 Hz, 2H). LC-MS: m/z 377.0 [M + H]+ |

TABLE 1-continued

Spectroscopic Data for Representative Compounds.

| Structure | ID # | Spectroscopic Data |
|---|---|---|
| 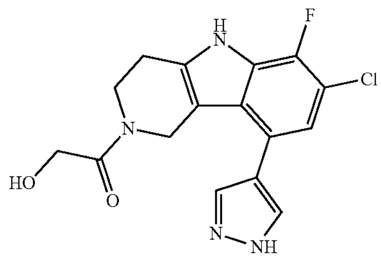 [SMILES: O=C(CO)N1CCc2[nH]c3c(F)c(Cl)cc(-c4cn[nH]c4)c3c2C1] | TDI-008185 | $^1$H NMR (DMSO-d$_6$, 400 MHz) δ 13.02 (brs, 1H), 11.81-11.72 (m, 1H), 8.01-7.89 (m, 1H), 7.64 (brs, 1H), 6.89 (d, J = 6.1 Hz, 1H), 4.60-4.51 (m, 1H), 4.36 (s, 1H), 4.16 (brd, J = 5.3 Hz, 2H), 3.98-3.76 (m, 1H), 3.66 (brs, 1H), 2.90-2.75 (m, 2H). LC-MS: m/z 349.0 [M + H]$^+$ |
| 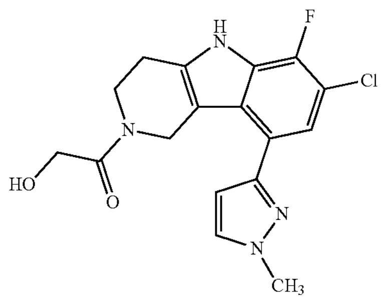 | TDI-008246 | $^1$H NMR: (DMSO-d$_6$, 400 MHz) δ 11.82-11.77 (m, 1H), 7.77 (s, 1H), 7.15-7.09 (m, 1H), 6.57-6.52 (m, 1H), 4.58-4.55 (m, 3H), 4.18-4.17 (m, 1H), 4.11-4.10 (m, 1H), 3.95-3.92 (m, 3H), 3.83-3.82 (m, 1H), 3.67-3.64 (m, 1H), 2.88-2.82 (m, 2H). LC-MS: m/z 363.0 [M + H]$^+$ |
| 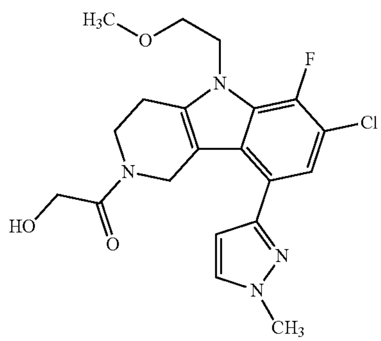 [SMILES: COCCn1c2c(c3c(-c4ccn(C)n4)cc(Cl)c(F)c31)CN(C(=O)CO)CC2] | TDI-008292 | $^1$H NMR (DMSO-d$_6$, 400 MHz) δ 7.79 (d, J = 2.1 Hz, 1H), 7.11 (dd, J = 6.4, 14.0 Hz, 1H), 6.51 (dd, J = 1.9, 15.0 Hz, 1H), 4.46 (brs, 2H), 4.36 (brs, 2H), 4.16 (s, 1H), 4.05 (s, 1H), 3.96-3.90 (m, 3H), 3.83 (brt, J = 5.5 Hz, 1H), 3.70-3.58 (m, 4H), 3.23-3.16 (m, 3H), 2.94-2.81 (m, 2H). LC-MS: m/z 421.1 [M + H]$^+$ |
| 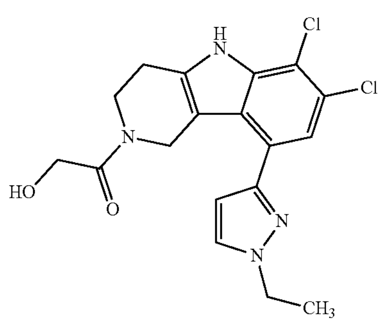 [SMILES: CCn1ccc(-c2cc(Cl)c(Cl)c3[nH]c4c(c23)CN(C(=O)CO)CC4)n1] | TDI-008371 | $^1$H NMR (400 MHz, CD$_3$OD) δ 7.74 (dd, J = 2.1, 9.5 Hz, 1H), 7.21 (d, J = 9.2 Hz, 1H), 6.50 (dd, J = 2.1, 12.7 Hz, 1H), 4.60 (s, 1H), 4.47 (s, 1H), 4.37-4.26 (m, 3H), 4.18 (s, 1H), 3.97 (t, J = 5.9 Hz, 1H), 3.76 (t, J = 5.7 Hz, 1H), 2.95 (td, J = 5.6, 19.8 Hz, 2H), 1.57 (t, J = 7.3 Hz, 3H). LC-MS: m/z 393.0 [M + H]$^+$ |
| 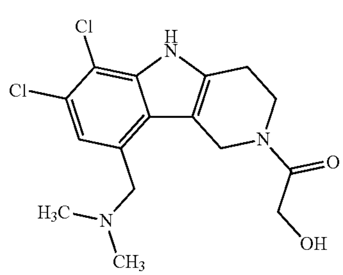 [SMILES: CN(C)Cc1cc(Cl)c(Cl)c2[nH]c3c(c12)CN(C(=O)CO)CC3] | TDI-008437 | LC-MS: m/z 356.0 [M + H]$^+$ |

TABLE 1-continued

Spectroscopic Data for Representative Compounds.

| Structure | ID # | Spectroscopic Data |
|---|---|---|
| 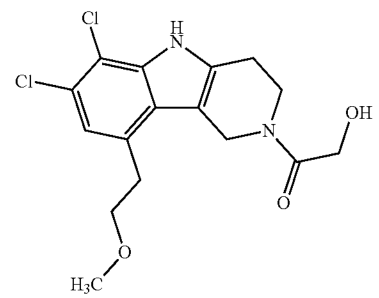 [SMILES: COCCc1cc(Cl)c(Cl)c2[nH]c3c(c12)CN(C(=O)CO)CC3] | TDI-008438 | LC-MS: m/z 357.1 [M + H]$^+$ |
| 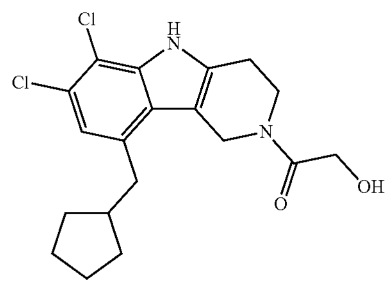 [SMILES: O=C(CO)N1CCc2[nH]c3c(Cl)c(Cl)cc(CC4CCCC4)c3c2C1] | TDI-008439 | LC-MS: m/z 381.1 [M + H]$^+$ |
| 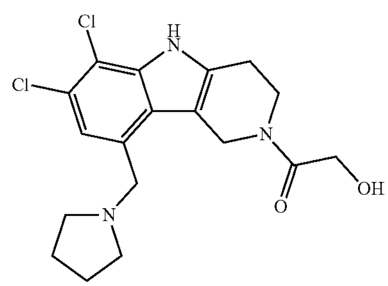 [SMILES: O=C(CO)N1CCc2[nH]c3c(Cl)c(Cl)cc(CN4CCCC4)c3c2C1] | TDI-008440 | LC-MS: m/z 382.1 [M + H]$^+$ |
| 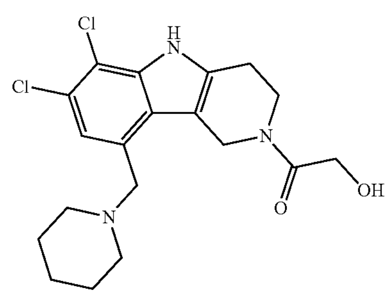 [SMILES: O=C(CO)N1CCc2[nH]c3c(Cl)c(Cl)cc(CN4CCCCC4)c3c2C1] | TDI-008441 | LC-MS: m/z 396.1 [M + H]$^+$ |
| 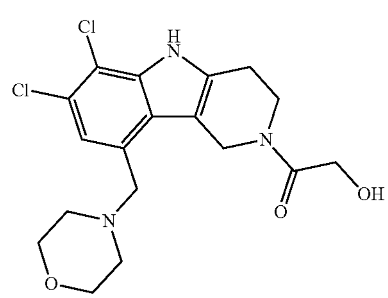 [SMILES: O=C(CO)N1CCc2[nH]c3c(Cl)c(Cl)cc(CN4CCOCC4)c3c2C1] | TDI-008442 | LC-MS: m/z 398.1 [M + H]$^+$ |

TABLE 1-continued

Spectroscopic Data for Representative Compounds.

| Structure | ID # | Spectroscopic Data |
|---|---|---|
| 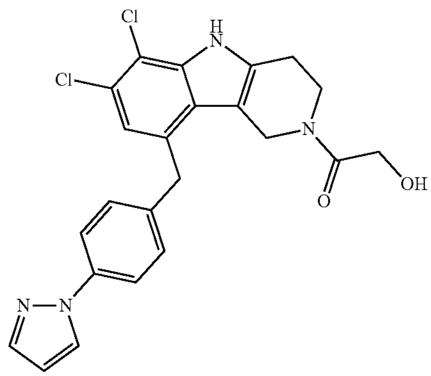 [SMILES: O=C(CO)N1CCc2[nH]c3c(Cl)c(Cl)cc(Cc4ccc(-n5cccn5)cc4)c3c2C1] | TDI-008443 | LC-MS: m/z 455.1 [M + H]+ |
| 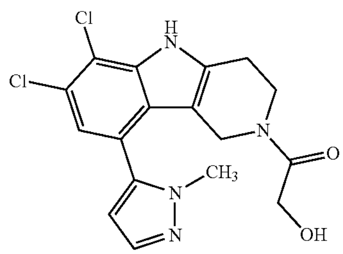 [SMILES: Cn1nccc1-c1cc(Cl)c(Cl)c2[nH]c3c(c12)CN(C(=O)CO)CC3] | TDI-008444 | LC-MS: m/z 379.1 [M + H]+ |
| 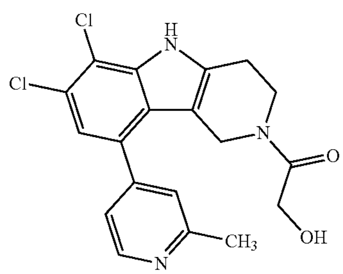 [SMILES: Cc1cc(-c2cc(Cl)c(Cl)c3[nH]c4c(c23)CN(C(=O)CO)CC4)ccn1] | TDI-008445 | LC-MS: m/z 390.1 [M + H]+ |
| 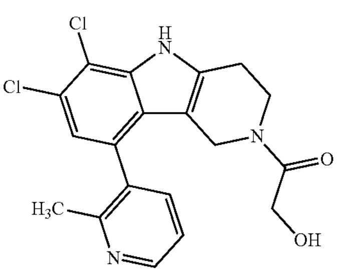 [SMILES: Cc1ncccc1-c1cc(Cl)c(Cl)c2[nH]c3c(c12)CN(C(=O)CO)CC3] | TDI-008446 | LC-MS: m/z 390.0 [M + H]+ |
| 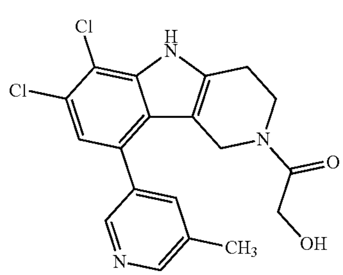 [SMILES: Cc1cncc(-c2cc(Cl)c(Cl)c3[nH]c4c(c23)CN(C(=O)CO)CC4)c1] | TDI-008447 | LC-MS: m/z 390.1 [M + H]+ |

TABLE 1-continued
Spectroscopic Data for Representative Compounds.
| Structure | ID # | Spectroscopic Data |
|---|---|---|
| 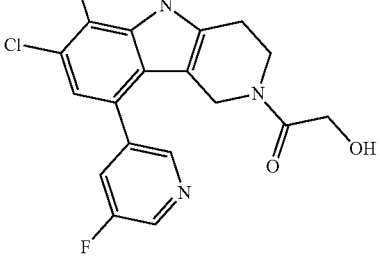 | TDI-008448 | LC-MS: m/z 394.0 [M + H]$^+$ |
| 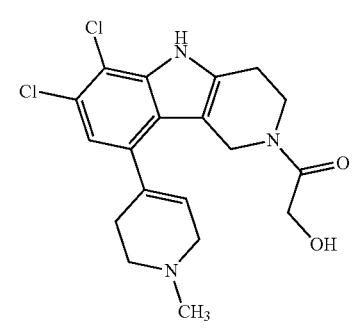 [SMILES: CN1CC=C(c2cc(Cl)c(Cl)c3[nH]c4c(c23)CN(C(=O)CO)CC4)CC1] | TDI-008449 | LC-MS: m/z 394.1 [M + H]$^+$ |
| 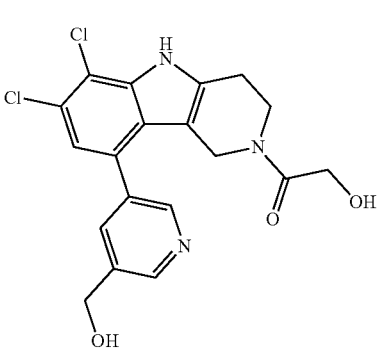 [SMILES: O=C(CO)N1CCc2[nH]c3c(Cl)c(Cl)cc(-c4cncc(CO)c4)c3c2C1] | TDI-008450 | LC-MS: m/z 406.1 [M + H]$^+$ |
| 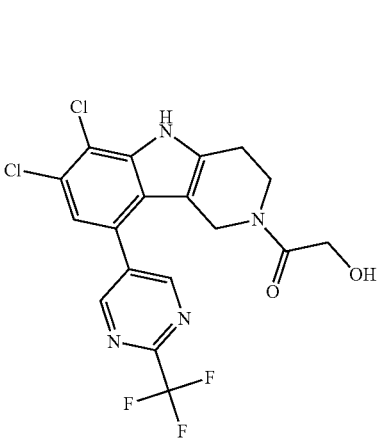 [SMILES: O=C(CO)N1CCc2[nH]c3c(Cl)c(Cl)cc(-c4cnc(C(F)(F)F)nc4)c3c2C1] | TDI-008451 | LC-MS: m/z 445.1 [M + H]$^+$ |

TABLE 1-continued

Spectroscopic Data for Representative Compounds.

| Structure | ID # | Spectroscopic Data |
|---|---|---|
| 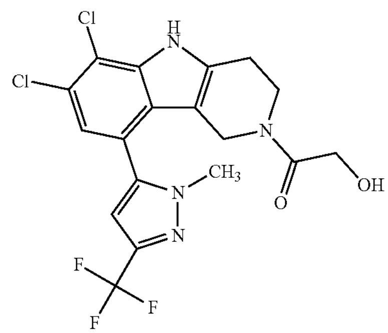 [SMILES: Cn1nc(C(F)(F)F)cc1-c1cc(Cl)c(Cl)c2[nH]c3c(c12)CN(C(=O)CO)CC3] | TDI-008452 | LC-MS: m/z 447.1 [M + H]$^+$ |
| 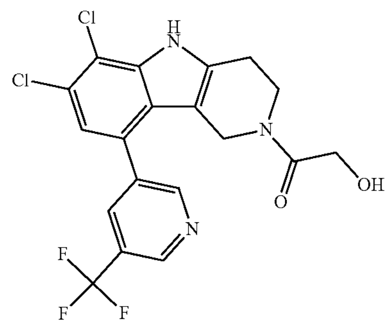 [SMILES: O=C(CO)N1CCc2[nH]c3c(Cl)c(Cl)cc(-c4cncc(C(F)(F)F)c4)c3c2C1] | TDI-008455 | LC-MS: m/z 444.0 [M + H]$^+$ |
| 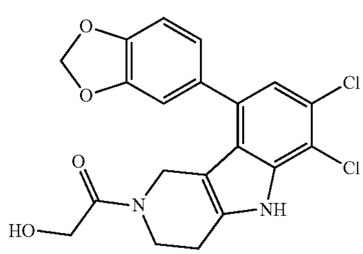 [SMILES: O=C(CO)N1CCc2[nH]c3c(Cl)c(Cl)cc(-c4ccc5c(c4)OCO5)c3c2C1] | TDI-008457 | LC-MS: m/z 419.1 [M + H]$^+$ |
| 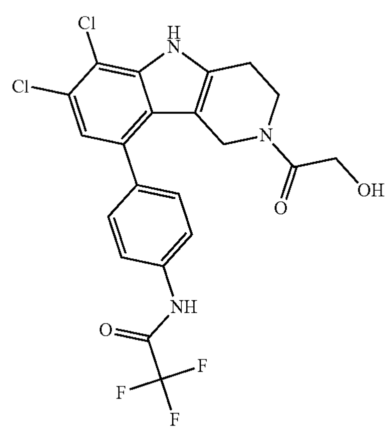 [SMILES: O=C(CO)N1CCc2[nH]c3c(Cl)c(Cl)cc(-c4ccc(NC(=O)C(F)(F)F)cc4)c3c2C1] | TDI-008458 | LC-MS: m/z 487.1 [M + H]$^+$ |

TABLE 1-continued

Spectroscopic Data for Representative Compounds.

| Structure | ID # | Spectroscopic Data |
|---|---|---|
| 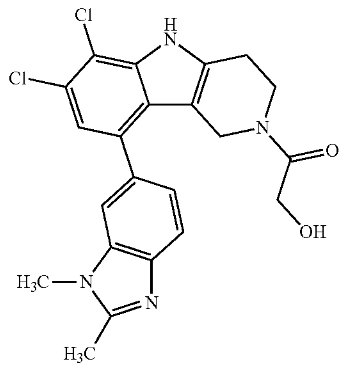 [SMILES: Cc1nc2ccc(-c3cc(Cl)c(Cl)c4[nH]c5c(c34)CN(C(=O)CO)CC5)cc2n1C] | TDI-008460 | LC-MS: m/z 443.1 [M + H]+ |
| 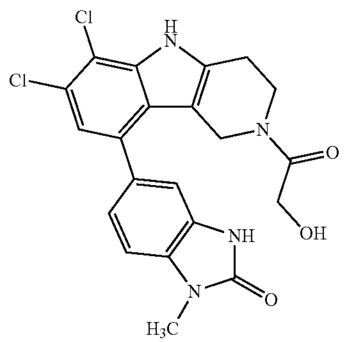 [SMILES: Cn1c(=O)[nH]c2cc(-c3cc(Cl)c(Cl)c4[nH]c5c(c34)CN(C(=O)CO)CC5)ccc21] | TDI-008461 | LC-MS: m/z 445.1 [M + H]+ |
| 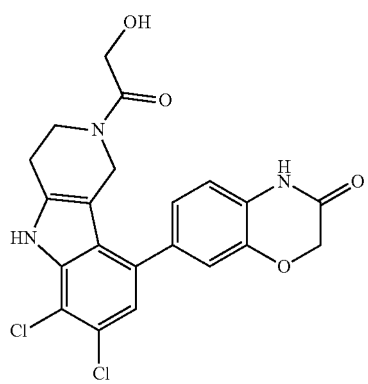 [SMILES: O=C1COc2cc(-c3cc(Cl)c(Cl)c4[nH]c5c(c34)CN(C(=O)CO)CC5)ccc2N1] | TDI-008462 | LC-MS: m/z 446.1 [M + H]+ |
| 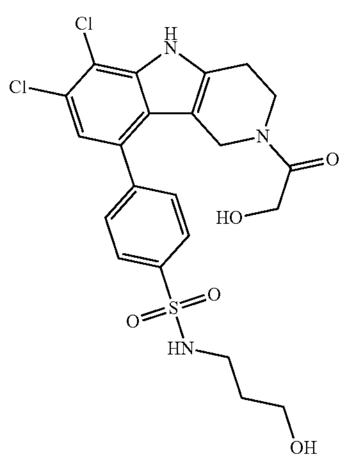 [SMILES: O=C(CO)N1CCc2[nH]c3c(Cl)c(Cl)cc(-c4ccc(S(=O)(=O)NCCCO)cc4)c3c2C1] | TDI-008464 | LC-MS: m/z 512.1 [M + H]+ |

TABLE 1-continued

Spectroscopic Data for Representative Compounds.

| Structure | ID # | Spectroscopic Data |
|---|---|---|
| 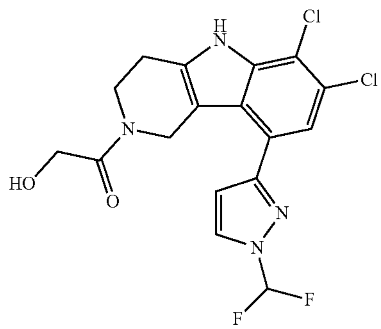 [SMILES: O=C(CO)N1CCc2[nH]c3c(Cl)c(Cl)cc(-c4ccn(C(F)F)n4)c3c2C1] | TDI-008474 | $^1$H NMR (DMSO-$d_6$, 400 MHz) δ 11.71 (d, J = 18.4 Hz, 1H), 8.35 (t, J = 3.5 Hz, 1H), 8.09-7.98 (m, 1H), 7.93-7.83 (m, 1H), 7.77-7.69 (m, 1H), 8.08-7.68 (m, 1H), 7.43-7.31 (m, 1H), 6.99-6.89 (m, 1H), 4.53 (s, 1H), 4.48 (t, J = 5.3 Hz, 1H), 4.55 (brs, 1H), 4.16 (d, J = 5.3 Hz, 1H), 4.03 (d, J = 5.7 Hz, 1H), 3.83 (t, J = 5.9 Hz, 1H), 3.69-3.62 (m, 1H), 2.93-2.80 (m, 2H). LC-MS: m/z 415.0 [M + H]$^+$ |
| 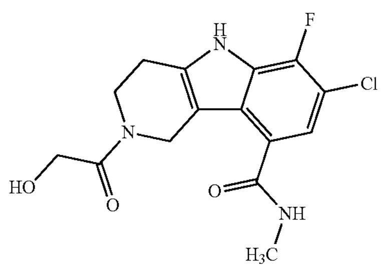 [SMILES: CNC(=O)c1cc(Cl)c(F)c2[nH]c3c(c12)CN(C(=O)CO)CC3] | TDI-008520 | $^1$H NMR (DMSO-$d_6$, 400 MHz) δ 12.00-11.88 (m, 1H), 8.39 (brd, J = 4.5 Hz, 1H), 7.29-7.22 (m, 1H), 4.67-4.49 (m, 2H), 4.24-4.09 (m, 2H), 3.89-3.61 (m, 2H), 2.93-2.76 (m, 5H). LC-MS: m/z 340.0 [M + H]$^+$ |
| 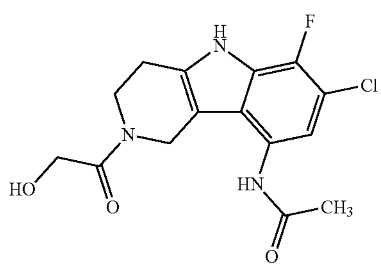 [SMILES: CC(=O)Nc1cc(Cl)c(F)c2[nH]c3c(c12)CN(C(=O)CO)CC3] | TDI-008522 | $^1$H NMR (400 MHz, CD$_3$OD) δ 6.90-6.84 (m, 1H), 4.80-4.77 (m, 1H), 4.66 (brs, 1H), 4.33 (brd, J = 18.8 Hz, 2H), 4.01-3.91 (m, 1H), 3.75 (brs, 1H), 2.98-2.83 (m, 2H), 2.21 (s, 3H). LC-MS: m/z 340.0 [M + H]$^+$ |
| 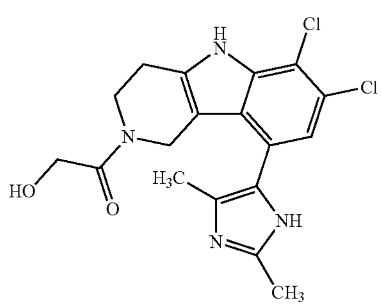 [SMILES: Cc1nc(C)c(-c2cc(Cl)c(Cl)c3[nH]c4c(c23)CN(C(=O)CO)CC4)[nH]1] | TDI-008605 | $^1$H NMR (DMSO-$d_6$, 400 MHz) δ 6.98 (d, J = 6.1 Hz, 1H), 4.36 (s, 1H), 4.29 (s, 1H), 4.19 (brs, 1H), 4.13 (s, 1H), 3.91 (t, J = 5.8 Hz, 1H), 3.71 (t, J = 5.7 Hz, 1H), 2.96-2.84 (m, 2H), 2.39 (d, J = 13.6 Hz, 3H), 2.15 (d, J = 5.4 Hz, 3H). LC-MS: m/z 393.0 [M + H]$^+$ |
| 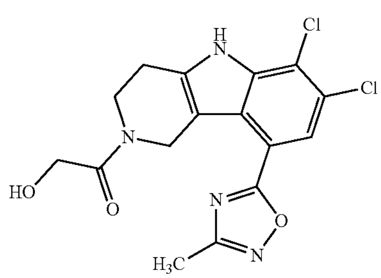 [SMILES: Cc1noc(-c2cc(Cl)c(Cl)c3[nH]c4c(c23)CN(C(=O)CO)CC4)n1] | TDI-008768 | $^1$H NMR (DMSO-$d_6$, 400 MHz) δ 12.11 (s, 1H), 7.79-7.85 (m, 1H), 4.79-4.89 (m, 2H), 4.53-4.67 (m, 1H), 4.13-4.24 (m, 2H), 3.87 (s, 1H), 3.64-3.75 (m, 1H), 2.85-3.00 (m, 2H), 2.45-2.48 (m, 3H). LC-MS: m/z 381.0 [M + H]$^+$ |

TABLE 1-continued

Spectroscopic Data for Representative Compounds.

| Structure | ID # | Spectroscopic Data |
| --- | --- | --- |
| 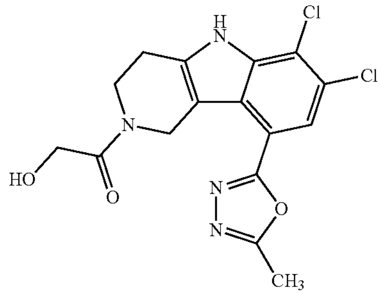 [SMILES: Cc1nnc(-c2cc(Cl)c(Cl)c3[nH]c4c(c23)CN(C(=O)CO)CC4)o1] | TDI-008777 | $^1$H NMR (DMSO-$d_6$, 400 MHz) δ 12.00 (brs, 1H), 7.66-7.74 (m, 1H), 4.74-4.90 (m, 2H), 4.62 (d, J = 4.63 Hz, 1H), 4.11-4.25 (m, 2H), 3.86 (s, 1H), 3.69 (s, 1H), 2.85-3.00 (m, 2H), 2.62 (s, 3H). LC-MS: m/z 381.1 [M + H]$^+$ |
| 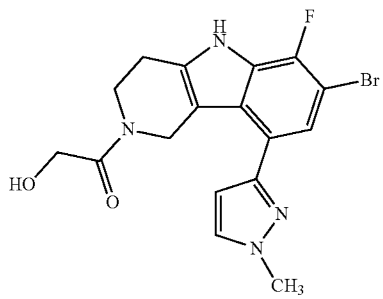 [SMILES: Cn1ccc(-c2cc(Br)c(F)c3[nH]c4c(c23)CN(C(=O)CO)CC4)n1] | TDI-008783 | $^1$H NMR (DMSO-$d_6$, 400 MHz) δ 11.77 (brd, J = 19.0 Hz, 1H), 7.76 (s, 1H), 7.19 (dd, J = 6.0, 17.2 Hz, 1H), 6.52 (dd, J = 2.0, 19.0 Hz, 1H), 4.59-4.49 (m, 3H), 4.19-4.04 (m, 2H), 3.92 (d, J = 13.5 Hz, 3H), 3.81 (brt, J = 5.5 Hz, 1H), 3.64 (brt, J = 5.5 Hz, 1H), 2.90 - 2.74 (m, 2H). LC-MS: m/z 407.0, 409.0 [M + H]$^+$ |
| 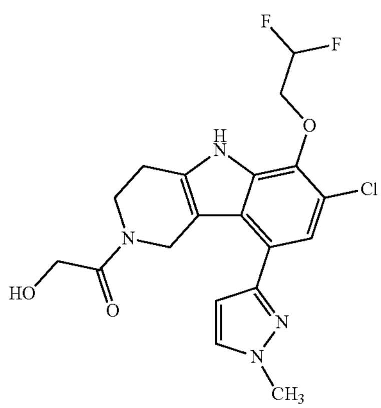 [SMILES: Cn1ccc(-c2cc(Cl)c(OCC(F)F)c3[nH]c4c(c23)CN(C(=O)CO)CC4)n1] | TDI-008796 | $^1$H NMR (DMSO-$d_6$, 400 MHz) δ 11.10 (brs, 1H), 7.72 (d, J = 2.08 Hz, 1H), 7.07 (s, 1H), 6.60-6.25 (m, 2H), 4.56 (s, 2H), 4.39 (td, J = 14.34, 3.85 Hz, 2H), 4.30-4.23 (m, 1H), 4.14 (brs, 2H), 3.94 (s, 3H), 3.77 (brs, 2H), 2.89 (brs, 2H). LC-MS: m/z 425.1 [M + H]$^+$ |
| 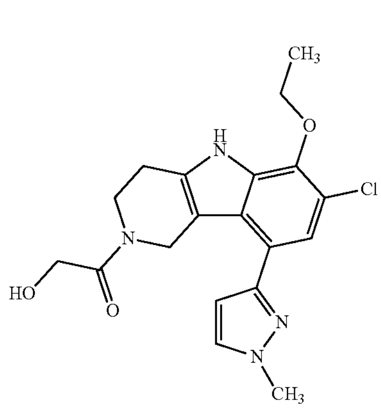 [SMILES: CCOc1c(Cl)cc(-c2ccn(C)n2)c2c3c([nH]c12)CCN(C(=O)CO)C3] | TDI-008797 | $^1$H NMR (DMSO-$d_6$, 400 MHz) δ 7.71 (s, 1H), 7.04 (s, 1H), 6.46 (brs, 1H), 4.56 (s, 2H), 4.28-4.09 (m, 4H), 3.94 (s, 3H), 3.76 (brs, 2H), 3.12 (brs, 24H), 2.99-2.79 (m, 2H), 2.50 (brd, J = 1.32 Hz, 8H), 1.41 (t, J = 6.95 Hz, 3H). LC-MS: m/z 389.0 [M + H]$^+$ |

TABLE 1-continued

Spectroscopic Data for Representative Compounds.

| Structure | ID # | Spectroscopic Data |
|---|---|---|
| 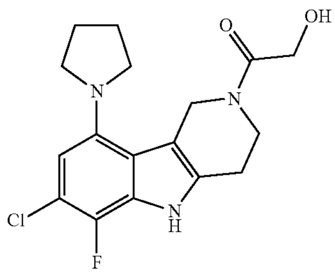 [SMILES: O=C(CO)N1CCc2[nH]c3c(F)c(Cl)cc(N4CCCC4)c3c2C1] | TDI-008860 | LC-MS: m/z 352.1 [M + H]+ |
| 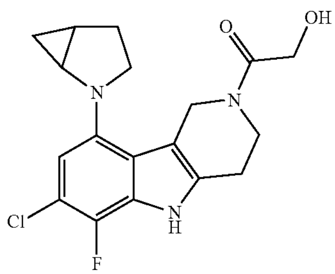 [SMILES: O=C(CO)N1CCc2[nH]c3c(F)c(Cl)cc(N4CCC5CC54)c3c2C1] | TDI-008861 | LC-MS: m/z 364.1 [M + H]+ |
| 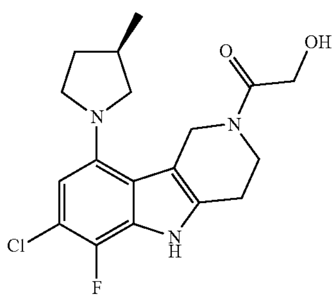 [SMILES: C[C@@H]1CCN(c2cc(Cl)c(F)c3[nH]c4c(c23)CN(C(=O)CO)CC4)C1] | TDI-008862 | LC-MS: m/z 366.1 [M + H]+ |
| 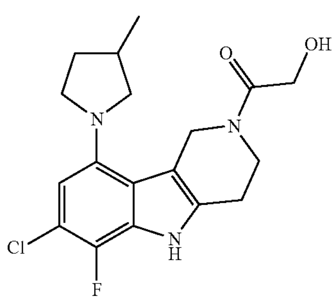 [SMILES: CC1CCN(c2cc(Cl)c(F)c3[nH]c4c(c23)CN(C(=O)CO)CC4)C1] | TDI-008863 | LC-MS: m/z 366.1 [M + H]+ |
| 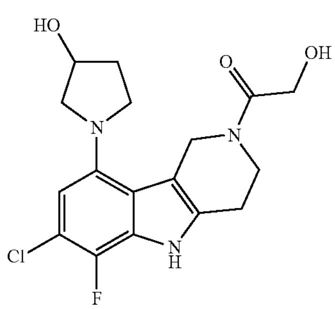 [SMILES: O=C(CO)N1CCc2[nH]c3c(F)c(Cl)cc(N4CCC(O)C4)c3c2C1] | TDI-008864 | LC-MS: m/z 368.1 [M + H]+ |

TABLE 1-continued

Spectroscopic Data for Representative Compounds.

| Structure | ID # | Spectroscopic Data |
|---|---|---|
| 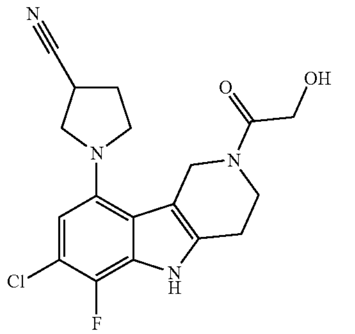 [SMILES: N#CC1CCN(c2cc(Cl)c(F)c3[nH]c4c(c23)CN(C(=O)CO)CC4)C1] | TDI-008865 | LC-MS: m/z 377.1 [M + H]+ |
| 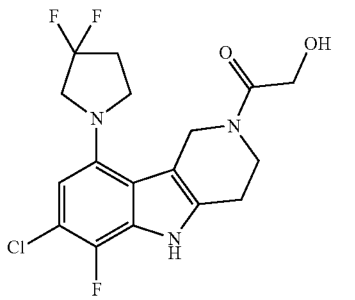 [SMILES: O=C(CO)N1CCc2[nH]c3c(F)c(Cl)cc(N4CCC(F)(F)C4)c3c2C1] | TDI-008866 | LC-MS: m/z 388.1 [M + H]+ |
| 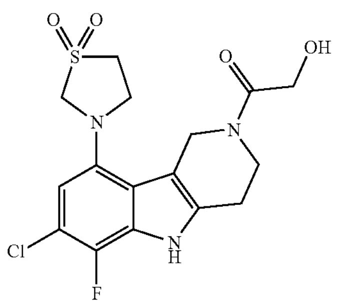 [SMILES: O=C(CO)N1CCc2[nH]c3c(F)c(Cl)cc(N4CCS(=O)(=O)C4)c3c2C1] | TDI-008867 | LC-MS: m/z 403.0 [M + H]+ |
| 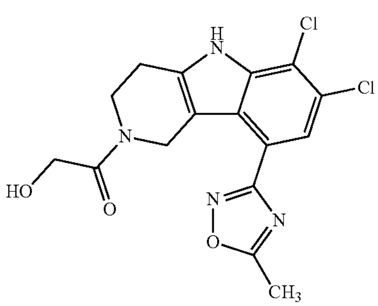 [SMILES: Cc1nc(-c2cc(Cl)c(Cl)c3[nH]c4c(c23)CN(C(=O)CO)CC4)no1] | TDI-008937 | $^1$H NMR (DMSO-d$_6$, 400 MHz) δ 7.68 (s, 1H), 4.87-4.67 (m, 2H), 4.60 (brs, 1H), 4.29-4.11 (m, 3H), 3.86 (brs, 1H), 3.69 (brs, 1H), 3.00-2.85 (m, 2H), 2.71 (s, 3H). LC-MS: m/z 381.0 [M + H]+ |
| 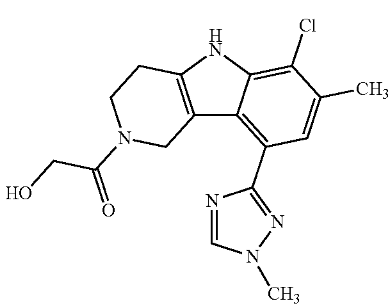 | TDI-008989 | $^1$H NMR (400 MHz, CD$_3$OD) δ 9.26-8.96 (m, 1H), 7.66-7.52 (m, 1H), 4.77 (brs, 3H), 4.42-7.25 (m, 2H), 4.15 (d, J = 5.99 Hz, 2H), 4.04-3.70 (m, 2H), 3.05-2.89 (m, 2H). LC-MS: m/z 380.0 [M + H]+ |

TABLE 1-continued

Spectroscopic Data for Representative Compounds.

| Structure | ID # | Spectroscopic Data |
|---|---|---|
| 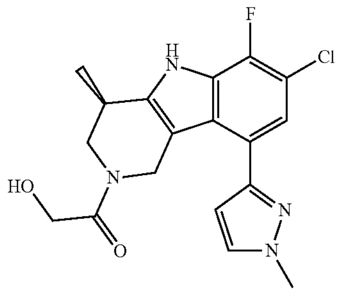 [SMILES: C[C@@H]1CN(C(=O)CO)Cc2c1[nH]c1c(F)c(Cl)cc(-c3ccn(C)n3)c21] | TDI-009000 | $^1$H NMR (400 MHz, CD$_3$OD) δ 7.67-7.65 (m, 1H), 7.07-7.03 (m, 1H), 6.45-6.42 (m, 1H), 4.58-4.34 (m, 2H), 4.30 (s, 1H), 4.21-4.19 (m, 1H), 4.00-3.99 (d, 3H), 3.94-3.91 (m, 0.5H), 3.78-3.75 (m, 0.5H), 3.68-3.66 (m 0.5H) 3.36-3.33 (m, 0.5H), 3.22-3.09 (m, 1H), 1.34 (q, 3H). LC-MS: m/z 377.0 [M + H]$^+$ |
| 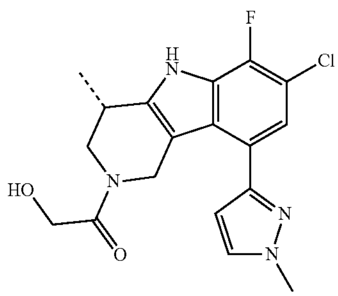 [SMILES: C[C@H]1CN(C(=O)CO)Cc2c1[nH]c1c(F)c(Cl)cc(-c3ccn(C)n3)c21] | TDI-009001 | $^1$H NMR (400 MHz, CD$_3$OD) δ 7.70-7.68 (m, 1H), 7.10-7.06 (m, 1H), 6.48-6.45 (m, 1H), 4.56-4.34 (m, 2H), 4.33 (s, 1H), 4.23-4.22 (m, 1H), 4.03-4.01 (d, 3H), 3.95-3.94 (m, 0.5H), 3.85-3.80 (m, 0.5H), 3.70-3.65 (m 0.5H) 3.41-3.36 (m, 0.5H), 3.24-3.13 (m, 1H), 1.39-1.35 (q, 3H). LC-MS: m/z 377.0 [M + H]$^+$ |
| 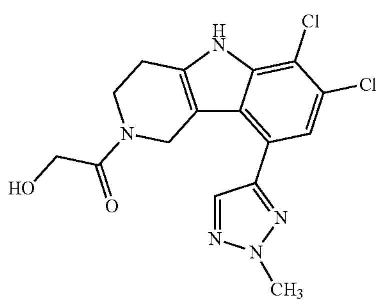 [SMILES: Cn1ncc(-c2cc(Cl)c(Cl)c3[nH]c4c(c23)CN(C(=O)CO)CC4)n1] | TDI-009007 | $^1$H NMR (DMSO-d$_6$, 400 MHz) δ 11.54 (brs, 1H), 8.11 (s, 1H), 7.40 (s, 1H), 4.61 (s, 2H), 4.31 (s, 3H), 4.21 (brs, 2H), 3.83 (brs, 2H), 2.96 (brs, 2H). LC-MS: m/z 380.0 [M + H]$^+$ |
| 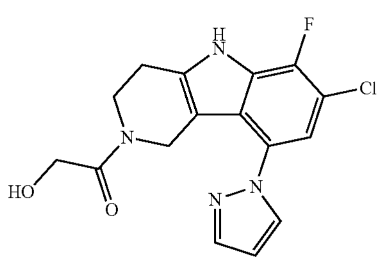 [SMILES: O=C(CO)N1CCc2[nH]c3c(F)c(Cl)cc(-n4cccn4)c3c2C1] | TDI-009013 | $^1$H NMR (400 MHz, CD$_3$OD) δ 8.02-7.95 (m, 1H), 7.83 (brd, J = 15.7 Hz, 1H), 7.15 (dd, J = 5.7, 13.3 Hz, 1H), 6.64-6.58 (m, 1H), 4.59 (s, 2H), 4.31 (brd, J = 6.8 Hz, 2H), 4.07 (d, J = 13.6 Hz, 2H), 3.95 (t, J = 5.8 Hz, 1H), 3.74 (t, J = 5.3 Hz, 1H), 3.50 (brs, 2H), 3.06-2.88 (m, 2H). LC-MS: m/z 349.0 [M + H]$^+$ |
| 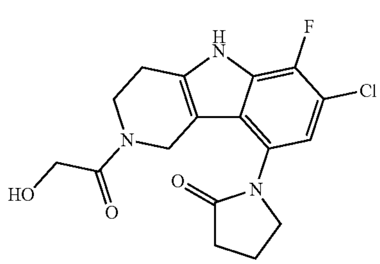 [SMILES: O=C(CO)N1CCc2[nH]c3c(F)c(Cl)cc(N4CCCC4=O)c3c2C1] | TDI-009072 | $^1$H NMR (400 MHz, CD$_3$OD) δ 7.00 (t, J = 6.0 Hz, 1H), 4.65-4.58 (m, 2H), 4.38 (s, 1H), 4.32 (s, 1H), 3.89 (s, 3H), 3.78 (s, 1H), 2.96 (s, 2H), 2.67 (t, J = 8.1 Hz, 2H), 2.34 (brd, J = 7.9 Hz, 2H). LC-MS: m/z 366.0 [M + H]$^+$ |

TABLE 1-continued

Spectroscopic Data for Representative Compounds.

| Structure | ID # | Spectroscopic Data |
|---|---|---|
| (structure) | TDI-009186 | $^1$H NMR (DMSO-d$_6$, 400 MHz) δ 11.70 (brs, 1H), 8.01 (s, 1H), 7.22 (brd, J = 6.5 Hz, 1H), 4.54 (s, 2H), 4.25 (s, 3H), 4.15 (brs, 2H), 3.77 (brs, 2H), 2.89 (brs, 2H). LC-MS: m/z 364.1 [M + H]$^+$ |
| (structure) | TDI-009208 | $^1$H NMR (DMSO-d$_6$, 400 MHz) δ 7.81 (brd, J = 4.6 Hz, 1H), 7.18 (brs, 1H), 6.66 (brd, J = 11.9 Hz, 1H), 4.64 (s, 2H), 4.20-4.14 (m, 1H), 4.10 (s, 1H), 3.99-3.92 (m, 3H), 3.86-3.77 (m, 1H), 3.65 (brt, J = 5.4 Hz, 1H), 2.93-2.77 (m, 2H). LC-MS: m/z 370.1 [M + H]$^+$ |

Biological Assays

Biochemical Assay:

Compounds were resuspended in 10 mM stock concentration using DMSO and tested to determine their IC$_{50}$ values against h-cGAS in 384-well polypropylene plates using RapidFire 365 mass spectrometry (RF-MS). The final concentration of full-length h-cGAS, dsDNA, ATP, and GTP were 100 nM, 25 nM, 100 μM, and 100 μM, respectively. The reaction buffer was composed of 20 mM Tris-HCl, pH 7.4, 150 mM NaCl, 5 mM MgCl$_2$, 1 μM ZnCl$_2$ and 0.01% Tween-20. Reaction solutions of 20 μl were incubated for 7 h at room temperature (RT) and stopped by addition of 60 μl of 0.5% (v/v) formic acid per well followed by RF-MS analysis. An aqueous solvent of 5 mM ammonium acetate, pH 10 was used for loading/washing process. An organic solvent comprising 5 mM ammonium acetate, pH 10 in 50% water, 25% acetone, and 25% acetonitrile was used for elution of the analytes. About 35 μl of each sample was aspirated from a 384-well plate and separated using a Graphitic carbon Type D cartridge. The sample loaded onto cartridge was then washed for 4 s at 1.5 ml min$^{-1}$ using the aqueous solvent. ATP, GTP, and cGAMP were eluted for 5 s using the organic solvent at a flow rate of 1.5 ml min$^{-1}$ followed by re-equilibration with the aqueous solvent for 5 s at a flow rate of 1.5 ml min$^{-1}$. The samples were analysed using a negative ionization mode in the mass spectrometer, with a gas temperature of 350° C., nebulizer pressure of 35 psi, and gas flow rate of 15 L min$^{-1}$. The acquisition range was between 300 and 800 m/z for all the chromatograms and the molecular masses of the detected peaks were: ATP: 505.9835, GTP: 521.9854, and cGAMP: 673.0906. The area under the curve (AUC) of the extracted ion counts for each analyte was calculated using the Agilent RapidFire Integrator software. Percent product formation for cGAMP was calculated as: product formation (%)=[(AUC$_{cGAMP}$×100)/ (AUC$_{cGAMP}$+½AUC$_{ATP}$+½AUC$_{GTP}$)]. Percent product formation from each sample at a given inhibitor concentration was used to determine percent inhibition by normalization against the positive control (no dsDNA) and negative control (no inhibitor). The % inhibition was calculated as follows: % inhibition=100×[(sample−average negative control)/(average positive control−average negative control)].

Representative compounds of the invention were tested in the foregoing biochemical assay with the results shown in Table 2.

TABLE 2 cGAS Biochemical Assay IC$_{50}$s.

| ID # | IC$_{50}$ h-cGAS RF-MS (μM) | ID # | IC$_{50}$ h-cGAS RF-MS (μM) | ID # | IC$_{50}$ h-cGAS RF-MS (μM) |
|---|---|---|---|---|---|
| TD1-004576 | 3.08 | TD1-008062 | 1.03 | TD1-008118 | 0.0768 |
| TD1-004581 | 2.41 | TD1-008069 | 0.0848 | TD1-008120 | 0.438 |
| TD1-005021 | 13.9 | TD1-008070 | 0.0228 | TD1-008130 | 1.12 |
| TD1-005323 | 5.86 | TD1-008071 | 0.0393 | TD1-008136 | 0.416 |
| TD1-005324 | 4.02 | TD1-008072 | 0.0975 | TD1-008179 | 0.506 |
| TD1-005325 | 3.23 | TD1-008073 | 0.0204 | TD1-008185 | 0.0322 |
| TD1-005397 | 0.352 | TD1-008074 | 0.0194 | TD1-008246 | 0.023 |
| TD1-005685 | 0.106 | TD1-008075 | 0.469 | TD1-008292 | 0.402 |
| TD1-005716 | 1.51 | TD1-008076 | 11.4 | TD1-008371 | 0.0232 |
| TD1-005719 | 3.29 | TD1-008077 | 0.0146 | TD1-008437 | 0.35 |
| TD1-005745 | 3.08 | TD1-008078 | 0.0318 | TD1-008438 | 0.112 |
| TD1-005776 | 0.203 | TD1-008079 | 0.890 | TD1-008439 | 0.663 |
| TD1-005777 | 24.7 | TD1-008080 | 0.0668 | TD1-008440 | 2.23 |
| TD1-005854 | 0.198 | TD1-008081 | 0.0479 | TD1-008441 | 5.22 |
| TD1-005855 | 1.74 | TD1-008082 | 0.322 | TD1-008442 | 0.706 |
| TD1-006171 | 7.69 | TD1-008083 | 0.0203 | TD1-008443 | 0.586 |
| TD1-006182 | 0.57 | TD1-008084 | 0.258 | TD1-008444 | 3.24 |
| TD1-006183 | 0.469 | TD1-008085 | 0.0309 | TD1-008445 | 0.035 |

TABLE 2-continued cGAS Biochemical Assay IC$_{50}$s.

| ID # | IC$_{50}$ h-cGAS RF-MS (μM) | ID # | IC$_{50}$ h-cGAS RF-MS (μM) | ID # | IC$_{50}$ h-cGAS RF-MS (μM) |
|---|---|---|---|---|---|
| TD1-006261 | 0.14 | TD1-008086 | 2.05 | TD1-008446 | 0.901 |
| TD1-006339 | 7.63 | TD1-008087 | 0.0102 | TD1-008447 | 0.0249 |
| TD1-006340 | 0.129 | TD1-008088 | 0.0569 | TD1-008448 | 0.0259 |
| TD1-006354 | 0.043 | TD1-008089 | 0.0644 | TD1-008449 | 0.42 |
| TD1-006358 | 0.597 | TD1-008090 | 0.0267 | TD1-008450 | 0.0545 |
| TD1-006359 | 0.44 | TD1-008091 | 0.031 | TD1-008451 | 9.78 |
| TD1-006360 | 0.327 | TD1-008092 | 1.84 | TD1-008452 | 2.91 |
| TD1-006366 | 0.201 | TDI-008093 | 0.330 | TD1-008455 | 0.154 |
| TD1-006528 | 0.031 | TDI-008094 | 0.371 | TD1-008457 | 0.0446 |
| TDI-006529 | 0.039 | TDI-008095 | 0.929 | TDI-008458 | 0.629 |
| TDI-006570 | 0.138 | TDI-008096 | 5.95 | TDI-008460 | 0.83 |
| TDI-006622 | 0.049 | TDI-008097 | 0.0422 | TDI-008461 | 0.344 |
| TDI-006923 | 19.3 | TDI-008098 | 0.0853 | TDI-008462 | 1.2 |
| TDI-006931 | 0.402 | TDI-008100 | 5.27 | TDI-008464 | 3.91 |
| TDI-006932 | >25 | TDI-008101 | 0.105 | TDI-008474 | 0.018 |
| TDI-007362 | 0.591 | TDI-008102 | 0.0402 | TDI-008520 | 1.04 |
| TDI-007433 | 1.45 | TDI-008103 | 0.0441 | TDI-008522 | 0.365 |
| TDI-007445 | 0.0275 | TDI-008104 | 0.0952 | TDI-008605 | 0.568 |
| TDI-007457 | 0.0541 | TDI-008105 | 0.107 | TDI-008768 | 0.0226 |
| TDI-007542 | 1.23 | TDI-008106 | 0.0493 | TDI-008777 | 0.0305 |
| TDI-007544 | 0.166 | TDI-008110 | 2.97 | TDI-009001 | 0.0327 |
| TDI-007553 | 0.3 | TDI-008111 | 0.268 | TDI-009007 | 0.0233 |
| TDI-007560 | 6.74 | TDI-008112 | 0.201 | TDI-009013 | 0.583 |
| TDI-007575 | 0.174 | TDI-008113 | 0.962 | TDI-009186 | 0.0176 |
| TDI-007576 | 0.323 | TDI-008114 | 0.0622 | TDI-009208 | 0.0392 |
| TDI-007586 | 0.352 | TDI-008115 | 0.0451 | TDI-008860 | 0.350 |
| TDI-007635 | 0.0428 | TDI-008116 | 0.0252 | TDI-008861 | 0.480 |
| TDI-007945 | 0.125 | TDI-008117 | 0.0182 | TDI-008862 | 0.478 |
| TDI-008026 | 0.203 | TDI-008783 | 0.0172 | TDI-008863 | 0.147 |
| TDI-008034 | 0.401 | TDI-008796 | 0.984 | TDI-008864 | 0.455 |
| TDI-008061 | 0.131 | TDI-008797 | 0.351 | TDI-008865 | 1.58 |
| TDI-008107 | 0.0524 | TDI-008937 | 0.0776 | TDI-008866 | 0.452 |
| TDI-008108 | 0.552 | TDI-008989 | 0.0459 | TDI-008867 | 6.93 |
| TDI-008109 | 2.33 | TDI-009000 | 0.0245 | TDI-009072 | 18.6 |

Cellular Assays:

Cell-based Lucia Luciferase Assay in THP1-Dual Cells.

Potency of select inhibitors is determined using human THP1-Dual cells carrying a secreted luciferase reporting interferon-induced gene expression. THP1-Dual cells were pre-incubated in 24-well plates (2.5×10$^5$ cells/well, 500 μl per well) over an indicated concentration range of inhibitors for 1 h. DMSO was added as negative control. Cells were transfected with 0.5 μg ml$^{-1}$ of 100-bp dsDNA ligands in complex with Lipofectamine 2000 (Invitrogen) for 24 h. Transfection complex was prepared by combining 0.25 μg of dsDNA in 25 μl Opti-MEM (Gibco) with 0.25 μl of Lipofectamine 2000 in 25 μl Opti-MEM and adding the 50 μl combined volume for each well containing cells. Luciferase luminescence was measured for each sample using QUANTI-Luc luciferase reagent (InvivoGen) following the manufacturer's protocol. Shortly, 20 μl of cell culture supernatant per well was transferred into a 96-well white opaque plate and luminescence was recorded using a Biotek Synergy Neo plate reader (BioTek, Winooski, Vt.) with the following parameters: 50 μl of luciferase reagent injection, end-point measurement with 4 s start time and 0.1 s reading time. Relative luciferase activity for each compound-treated sample was calculated using Lipofectamine 2000 treated sample as negative control and Lipofectamine 2000:dsDNA complex treated sample without compound as positive control, i.e., relative luciferase activity=(RLU$_{sample}$-RLU$_{negative\ control}$)/(RLU$_{positive\ control}$-RLU$_{negative\ control}$) where RLU indicates raw luciferase unit.

Representative compounds of the invention were tested in the foregoing cellular assay with the results shown in Table 3.

TABLE 3

Cell-based Lucia luciferase assay IC$_{50}$s.

| ID # | THP1-Dual, Lucia luciferase IC$_{50}$ (μM) | ID # | THP1-Dual, Lucia luciferase IC50 (μM) | ID # | THP1-Dual, Lucia luciferase IC$_{50}$ (μM) |
|---|---|---|---|---|---|
| TDI-6570 | >40 | TDI-8179 | 34 | TDI-8865 | >10.0 |
| TDI-7445 | 5.26 | TDI-8185 | 9.9 | TDI-8866 | >10.0 |
| TDI-7635 | 8.14 | TDI-8246 | 1.7 | TDI-8867 | >10.0 |
| TDI-8070 | 4.95 | TDI-8292 | >40.0 | TDI-8937 | 16.1 |
| TDI-8071 | 9 | TDI-8371 | 6.52 | TDI-8989 | 6.71 |
| TDI-8073 | 6.23 | TDI-8768 | 5.8 | TDI-9000 | 2.89 |
| TDI-8074 | 6.85 | TDI-8777 | 12.9 | TDI-9001 | 3.18 |
| TDI-8077 | 3.32 | TDI-8783 | 3.41 | TDI-9007 | 1.15 |
| TDI-8087 | 1.97 | TDI-8796 | >40.0 | TDI-9013 | >40.0 |
| TDI-8116 | 6.43 | TDI-8860 | >10.0 | TDI-9072 | >40.0 |
| TDI-8117 | 6.19 | TDI-8861 | >10.0 | TDI-9186 | 0.72 |
| TDI-8130 | 25.78 | TDI-8863 | >10.0 | TDI-9208 | 4.4 |
| TDI-8136 | 15.86 | TDI-8864 | >10.0 | | |

IFNB1 mRNA Expression in Cells.

Cellular activation of cGAS enzyme leads to IFNB1 mRNA expression in THP1 cells, primary human macrophage cells, and human PBMCs. IFNB1 mRNA expression was quantified using qRT-PCR. Total RNA was isolated from 5×10$^5$ THP1 cells per well of a 12-well plate, which were pre-incubated with inhibitors for 1 h. Human primary macrophages were used at 3×10$^5$ cells per well of a 12-well plate. Human PBMCs were used at 1×10$^6$ cells per well of a 12-well plate. Cells were transfected using 100 μl of Opti-MEM transfection solution comprising 2 μg of 100-bp dsDNA complexed with 2 μl of Lipofectamine 2000. Cells were harvested 4 hours post-transfection, and RNA was extracted using 500 μl of Trizol (Ambion). 800 ng of total RNA was reverse-transcribed for cDNA synthesis in 20 μl final reaction volume using oligo(dT)$_{20}$ primer at 2.5 μM and 10 U/μl Superscript III (Thermo-Fisher) for 50 min at 50° C. Quantitative PCR was performed on a Mx3000P qPCR System (Agilent Technologies) using $\frac{1}{20}^{th}$ volume of reverse transcription material as an input for each qPCR reaction. Expression levels of IFNB1 and TUBA1B mRNAs were measured in technical triplicate for each sample. Threshold cycle ($C_T$) values obtained for IFNB1 mRNAs were normalized to TUBA1B $C_T$ values and used to calculate $\Delta C_T$. Relative mRNA expression levels of IFNB1 were calculated using the $\Delta \Delta C_T$ method ($2^{\Delta \Delta C_T}$). The extent of cGAS inhibition was determined by normalizing the IFNB1 mRNA expression level for each sample relative to DMSO only control.

Representative compounds of the invention were tested in the foregoing cellular assays with the results shown in Table 4.

TABLE 4

| ID # | THP1, qRT-PCR IC$_{50}$ (μM) | Human Macrophage, qRT-PCR IC$_{50}$ (μM) | Fresh human PBMCs, qRT-PCR IC$_{50}$ (μM) | Freeze-thawed human PBMCs, qRT-PCR IC$_{50}$ (μM) |
|---|---|---|---|---|
| TDI-7445 | 1.44 | 1.2 | n.d. | n.d. |
| TDI-7635 | 2.14 | n.d. | n.d. | n.d. |

TABLE 4-continued

| ID # | THP1, qRT-PCR IC$_{50}$ (μM) | Human Macrophage, qRT-PCR IC$_{50}$ (μM) | Fresh human PBMCs, qRT-PCR IC$_{50}$ (μM) | Freeze-thawed human PBMCs, qRT-PCR IC$_{50}$ (μM) |
|---|---|---|---|---|
| TDI-8077 | 0.93 | 0.86 | 1.15 | n.d. |
| TDI-8087 | 0.95 | 0.62 | n.d. | n.d. |
| TDI-8246 | 1.09 | 0.6 | 1.12 | 1.16 | n.d. not determined

Early experiments in vivo suggest that compounds described herein penetrate the blood-brain barrier. They would therefore be useful in treating autoimmune disorders within the CNS.

The invention claimed is:

1. A compound of formula (I):

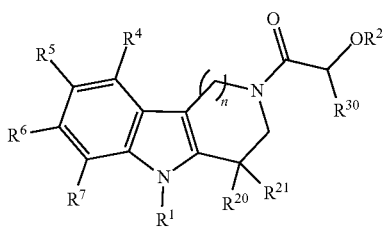

(I)

or a pharmaceutically acceptable salt or stereoisomer thereof, wherein:

$R^1$ is H, (C$_1$-C$_3$) alkyl, (C$_1$-C$_3$) fluoroalkyl, or CH$_2$CH$_2$OR$^3$;

$R^2$ is H, (C$_1$-C$_3$) alkyl, or CH$_2$CH$_2$OR$^3$;

$R^3$ is H or (C$_1$-C$_3$) alkyl;

$R^4$ is H, halogen, CN, (C$_1$-C$_6$) hydrocarbyl, (C$_1$-C$_3$) alkylene-NH$_2$, (C$_1$-C$_3$) alkylene-NH(C$_1$-C$_3$) alkyl, (C$_1$-C$_3$) alkylene-N[(C$_1$-C$_3$) alkyl]$_2$, (C$_1$-C$_3$) alkylene-O(C$_1$-C$_3$) alkyl, (C$_1$-C$_3$) alkylene-heterocyclyl, benzyl, benzyl-heterocyclyl, C(O)NH(C$_1$-C$_3$) alkyl, NH(C$_1$-C$_3$) acyl, O(C$_1$-C$_3$) alkyl, phenyl, monocyclic heterocyclyl, or bicyclic heterocyclyl;

wherein the phenyl is optionally substituted with one or more substituents independently selected from the group consisting of halogen, CN, C(O)NH$_2$, NH$_2$, NH(C$_1$-C$_3$) alkyl, N[(C$_1$-C$_3$) alkyl]$_2$, NH(C$_1$-C$_3$) acyl, NH(C$_1$-C$_3$) fluoroacyl, OH, O(C$_1$-C$_3$) alkyl, —OCH$_2$O—, —OCH$_2$CH$_2$O—, and S(O)$_2$NH(C$_1$-C$_3$) hydroxyalkyl;

wherein the monocyclic heterocyclyl is optionally substituted with one or more substituents independently selected from the group consisting of halogen, CN, (C$_1$-C$_3$) alkyl, (C$_1$-C$_3$) fluoroalkyl, (C$_1$-C$_3$) hydroxyalkyl, NH$_2$, NH(C$_1$-C$_3$) alkyl, OH, O(C$_1$-C$_3$) alkyl, and =O; and wherein the bicyclic heterocyclyl is optionally substituted with one or more substituents independently selected from the group consisting of (C$_1$-C$_3$) alkyl, OH, and =O;

$R^5$ is H, halogen, CN, (C$_1$-C$_3$) alkyl, (C$_1$-C$_3$) fluoroalkyl, O(C$_1$-C$_3$) alkyl, O(C$_1$-C$_3$) fluoroalkyl, or azetidin-1-yl;

$R^6$ is H, halogen, CN, CH$_3$, CF$_3$, CH=CH$_2$, or C≡CH;

$R^7$ is H, halogen, CN, (C$_1$-C$_3$) alkyl, (C$_1$-C$_3$) fluoroalkyl, O(C$_1$-C$_3$) alkyl, or O(C$_1$-C$_3$) fluoroalkyl;

$R^{20}$ is H or (C$_1$-C$_3$) alkyl;

$R^{21}$ is H or (C$_1$-C$_3$) alkyl;

$R^{30}$ is H; or $R^2$ and $R^{30}$, taken together with the atoms to which they are attached, form a 4- to 6-membered aliphatic heterocyclyl; and n is 1 or 2;

with the provisos that:

(1) if $R^1$ is H, $R^2$ is CH$_3$, and $R^5$ is halogen, then $R^7$ is not H or Cl;

(2) if $R^2$ is (C$_1$-C$_3$) alkyl, then $R^4$, $R^5$, $R^6$, and $R^7$ are not simultaneously H; and (3) if $R^2$ is (C$_1$-C$_3$) alkyl and $R^5$ is OCH$_3$, then $R^7$ is not H.

2. The compound according to claim 1, or a pharmaceutically acceptable salt or stereoisomer thereof, wherein:

$R^{20}$ is H or (C$_1$-C$_3$) alkyl;

$R^{21}$ is H; and n is 1.

3. The compound according to claim 2, or a pharmaceutically acceptable salt or stereoisomer thereof, wherein $R^1$ is H.

4. The compound according to claim 2, or a pharmaceutically acceptable salt or stereoisomer thereof, wherein $R^2$ is H.

5. The compound according to claim 2, or a pharmaceutically acceptable salt or stereoisomer thereof, wherein $R^6$ is halogen.

6. The compound according to claim 5, or a pharmaceutically acceptable salt or stereoisomer thereof, wherein $R^7$ is F.

7. The compound according to claim 6, or a pharmaceutically acceptable salt or stereoisomer thereof, wherein $R^5$ is H.

8. The compound according to claim 7, or a pharmaceutically acceptable salt or stereoisomer thereof, wherein:

$R^2$ is H;

$R^4$ is 1-methylpyrazol-3-yl; and $R^{20}$ is H or CH$_3$.

9. The compound according to claim 2, or a pharmaceutically acceptable salt or stereoisomer thereof, wherein $R^4$ is a monocyclic heteroaryl, wherein the monocyclic heteroaryl is optionally substituted with one substituent selected from the group consisting of halogen, CN, CH$_3$, CHF$_2$, NH$_2$, and OCH$_3$.

10. The compound according to claim 9, or a pharmaceutically acceptable salt or stereoisomer thereof, wherein the monocyclic heteroaryl is pyrrolyl, furanyl, thiophenyl, pyrazolyl, imidazolyl, isoxazolyl, oxazolyl, isothiazolyl, thiazolyl, triazolyl, oxadiazolyl, pyridinyl, pyridazinyl, pyrimidinyl, or pyrazinyl, wherein the pyrrolyl, furanyl, thiophenyl, pyrazolyl, imidazolyl, isoxazolyl, oxazolyl, isothiazolyl, thiazolyl, triazolyl, oxadiazolyl, pyridinyl, pyridazinyl, pyrimidinyl, or pyrazinyl is optionally substituted with one substituent selected from the group consisting of halogen, CN, CH$_3$, CHF$_2$, NH$_2$, and OCH$_3$.

11. The compound according to claim 10, or a pharmaceutically acceptable salt or stereoisomer thereof, wherein the monocyclic heteroaryl is pyrazolyl, imidazolyl, isoxazolyl, oxazolyl, triazolyl, or oxadiazolyl, wherein the pyrazolyl, imidazolyl, isoxazolyl, oxazolyl, triazolyl, or oxadiazolyl is optionally substituted with one substituent selected from the group consisting of halogen, CN, CH$_3$, CHF$_2$, NH$_2$, and OCH$_3$.

12. The compound according to claim 11, or a pharmaceutically acceptable salt or stereoisomer thereof, wherein the monocyclic heteroaryl is pyrazolyl or triazolyl, wherein the pyrazolyl or triazolyl is optionally substituted with one substituent selected from the group consisting of halogen, CN, CH$_3$, CHF$_2$, NH$_2$, and OCH$_3$.

13. The compound according to claim 12, or a pharmaceutically acceptable salt or stereoisomer thereof, wherein the pyrazolyl or triazolyl is optionally substituted with one CH$_3$ substituent.

14. The compound according to claim 2, or a pharmaceutically acceptable salt or stereoisomer thereof, wherein R$^7$ is F or Cl.

15. The compound according to claim 2, or a pharmaceutically acceptable salt or stereoisomer thereof, wherein R$^7$ is F.

16. The compound according to claim 2, or a pharmaceutically acceptable salt or stereoisomer thereof, wherein R$^{20}$ is H or CH$_3$.

17. A pharmaceutical formulation comprising a pharmaceutically acceptable carrier and a compound according to claim 1, or a pharmaceutically acceptable salt or stereoisomer thereof.

18. A method for inhibiting an inflammatory response in a patient, wherein the method comprises administering to the patient in need thereof a therapeutically effective amount of a compound of formula (II):

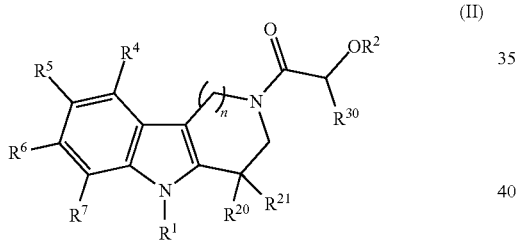

(II)

or a pharmaceutically acceptable salt or stereoisomer thereof,
wherein:
R$^1$ is H, (C$_1$-C$_3$) alkyl, (C$_1$-C$_3$) fluoroalkyl, or CH$_2$CH$_2$OR$^3$;
R$^2$ is H, (C$_1$-C$_3$) alkyl, or CH$_2$CH$_2$OR$^3$;
R$^3$ is H or (C$_1$-C$_3$) alkyl;
R$^4$ is H, halogen, CN, (C$_1$-C$_6$) hydrocarbyl, (C$_1$-C$_3$) alkylene-NH$_2$, (C$_1$-C$_3$) alkylene-NH(C$_1$-C$_3$) alkyl, (C$_1$-C$_3$) alkylene-N[(C$_1$-C$_3$) alkyl]$_2$, (C$_1$-C$_3$) alkylene-O (C$_1$-C$_3$) alkyl, (C$_1$-C$_3$) alkylene-heterocyclyl, benzyl, benzyl-heterocyclyl, C(O)NH(C$_1$-C$_3$) alkyl, NH(C$_1$-C$_3$) acyl, O(C$_1$-C$_3$) alkyl, phenyl, monocyclic heterocyclyl, or bicyclic heterocyclyl;
wherein the phenyl is optionally substituted with one or more substituents independently selected from the group consisting of halogen, CN, C(O)NH$_2$, NH$_2$, NH(C$_1$-C$_3$) alkyl, N[(C$_1$-C$_3$) alkyl]$_2$, NH(C$_1$-C$_3$) acyl, NH(C$_1$-C$_3$) fluoroacyl, OH, O(C$_1$-C$_3$) alkyl, —OCH$_2$O—, —OCH$_2$CH$_2$O—, and S(O)$_2$NH(C$_1$-C$_3$) hydroxyalkyl;
wherein the monocyclic heterocyclyl is optionally substituted with one or more substituents independently selected from the group consisting of halogen, CN, (C$_1$-C$_3$) alkyl, (C$_1$-C$_3$) fluoroalkyl, (C$_1$-C$_3$) hydroxyalkyl, NH$_2$, NH(C$_1$-C$_3$) alkyl, OH, O(C$_1$-C$_3$) alkyl, and =O; and
wherein the bicyclic heterocyclyl is optionally substituted with one or more substituents independently selected from the group consisting of (C$_1$-C$_3$) alkyl, OH, and =O;
R$^5$ is H, halogen, CN, (C$_1$-C$_3$) alkyl, (C$_1$-C$_3$) fluoroalkyl, O(C$_1$-C$_3$) alkyl, O(C$_1$-C$_3$) fluoroalkyl, or azetidin-1-yl;
R$^6$ is H, halogen, CN, CH$_3$, CF$_3$, CH=CH$_2$, or C≡CH;
R$^7$ is H, halogen, CN, (C$_1$-C$_3$) alkyl, (C$_1$-C$_3$) fluoroalkyl, O(C$_1$-C$_3$) alkyl, or O(C$_1$-C$_3$) fluoroalkyl;
R$^{20}$ is H or (C$_1$-C$_3$) alkyl;
R$^{21}$ is H or (C$_1$-C$_3$) alkyl;
R$^{30}$ is H; or
R$^2$ and R$^{30}$, taken together with the atoms to which they are attached, form a 4- to 6-membered aliphatic heterocyclyl; and
n is 1 or 2.

19. A method for treating cancer metastasis in a patient, wherein the method comprises administering to the patient in need thereof a therapeutically effective amount of a compound of formula (II):

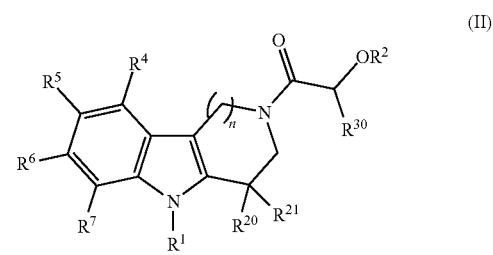

(II)

or a pharmaceutically acceptable salt or stereoisomer thereof,
wherein:
R$^1$ is H, (C$_1$-C$_3$) alkyl, (C$_1$-C$_3$) fluoroalkyl, or CH$_2$CH$_2$OR$^3$;
R$^2$ is H, (C$_1$-C$_3$) alkyl, or CH$_2$CH$_2$OR$^3$;
R$^3$ is H or (C$_1$-C$_3$) alkyl;
R$^4$ is H, halogen, CN, (C$_1$-C$_6$) hydrocarbyl, (C$_1$-C$_3$) alkylene-NH$_2$, (C$_1$-C$_3$) alkylene-NH(C$_1$-C$_3$) alkyl, (C$_1$-C$_3$) alkylene-N[(C$_1$-C$_3$) alkyl]$_2$, (C$_1$-C$_3$) alkylene-O(C$_1$-C$_3$) alkyl, (C$_1$-C$_3$) alkylene-heterocyclyl, benzyl, benzyl-heterocyclyl, C(O)NH(C$_1$-C$_3$) alkyl, NH(C$_1$-C$_3$) acyl, O(C$_1$-C$_3$) alkyl, phenyl, monocyclic heterocyclyl, or bicyclic heterocyclyl;
wherein the phenyl is optionally substituted with one or more substituents independently selected from the group consisting of halogen, CN, C(O)NH$_2$, NH$_2$, NH(C$_1$-C$_3$) alkyl, N[(C$_1$-C$_3$)alkyl]$_2$, NH(C$_1$-C$_3$) acyl, NH(C$_1$-C$_3$) fluoroacyl, OH, O(C$_1$-C$_3$) alkyl, —OCH$_2$O—, —OCH$_2$CH$_2$O—, and S(O)$_2$NH(C$_1$-C$_3$) hydroxyalkyl;
wherein the monocyclic heterocyclyl is optionally substituted with one or more substituents independently selected from the group consisting of halogen, CN, (C$_1$-C$_3$) alkyl, (C$_1$-C$_3$) fluoroalkyl, (C$_1$-C$_3$) hydroxyalkyl, NH$_2$, NH(C$_1$-C$_3$) alkyl, OH, O(C$_1$-C$_3$) alkyl, and =O; and wherein the bicyclic heterocyclyl is optionally substituted with one or more substituents independently selected from the group consisting of $(C_1$-$C_3)$ alkyl, OH, and $=O$;

$R^5$ is H, halogen, CN, $(C_1$-$C_3)$ alkyl, $(C_1$-$C_3)$ fluoroalkyl, $O(C_1$-$C_3)$ alkyl, $O(C_1$-$C_3)$ fluoroalkyl, or azetidin-1-yl;

$R^6$ is H, halogen, CN, $CH_3$, $CF_3$, $CH=CH_2$, or $C\equiv CH$;

$R^7$ is H, halogen, CN, $(C_1$-$C_3)$ alkyl, $(C_1$-$C_3)$ fluoroalkyl, $O(C_1$-$C_3)$ alkyl, or $O(C_1$-$C_3)$ fluoroalkyl;

$R^{20}$ is H or $(C_1$-$C_3)$ alkyl;

$R^{21}$ is H or $(C_1$-$C_3)$ alkyl;

$R^{30}$ is H; or $R^2$ and $R^{30}$, taken together with the atoms to which they are attached, form a 4- to 6-membered aliphatic heterocyclyl; and n is 1 or 2.

\* \* \* \* \*